US010954218B2

(12) United States Patent
Bae et al.

(10) Patent No.: US 10,954,218 B2
(45) Date of Patent: Mar. 23, 2021

(54) CARBAZOLE DERIVATIVE AND ORGANIC LIGHT EMITTING DEVICE USING SAME

(71) Applicant: LG Chem, Ltd., Seoul (KR)

(72) Inventors: Jaesoon Bae, Daejeon (KR); Jinseck Kim, Daejeon (KR); Sungkyoung Kang, Daejeon (KR); Jaechol Lee, Daejeon (KR); Seokhee Yoon, Daejeon (KR); Donggu Lee, Daejeon (KR); Chung Whan Lee, Daejeon (KR)

(73) Assignee: LG Chem, Ltd.

( * ) Notice: Subject to any disclaimer, the term of this patent is extended or adjusted under 35 U.S.C. 154(b) by 272 days.

(21) Appl. No.: 15/777,457

(22) PCT Filed: Nov. 30, 2016

(86) PCT No.: PCT/KR2016/013968
§ 371 (c)(1),
(2) Date: May 18, 2018

(87) PCT Pub. No.: WO2017/095141
PCT Pub. Date: Jun. 8, 2017

(65) Prior Publication Data
US 2018/0354933 A1  Dec. 13, 2018

(30) Foreign Application Priority Data

Nov. 30, 2015  (KR) .................. 10-2015-0169384
Nov. 16, 2016  (KR) .................. 10-2016-0152866

(51) Int. Cl.
*C07D 403/12* (2006.01)
*C07D 403/14* (2006.01)
(Continued)

(52) U.S. Cl.
CPC ......... *C07D 403/12* (2013.01); *C07D 209/82* (2013.01); *C07D 209/88* (2013.01);
(Continued)

(58) Field of Classification Search
CPC .. C07D 403/12; C07D 403/10; C07D 403/14; C07D 209/82; C07D 487/14;
(Continued)

(56) References Cited

U.S. PATENT DOCUMENTS

2006/0115680 A1 * 6/2006 Hwang ............... C07D 209/88
428/690
2013/0175508 A1 7/2013 Kwon et al.

FOREIGN PATENT DOCUMENTS

EP      3431467 A1    1/2019
JP      2010222355 A  10/2010
(Continued)

OTHER PUBLICATIONS

Search report from International Application No. PCT/KR2016/013968, dated Mar. 10, 2017.
Degutyte, R., et al., "Synthesis of a bifunctional 1,2,3,4-tetrahydroquinoline derivative: 1,8-bix(9-ethyl-9H-carbazol-3-yl)-1,2,3,4,5,6,7,8-octahydro-quino[5,6-f]quinoline-3,6-diol." ARKIVOC (Archive for Organic Chemistry), vol. 11, 2009, pp. 115-122.
Lengvinaite, S., et al., "Cross-linkable aromatic amines as materials for insoluble hole-transporting layers in light-emitting devices." Synthetic Materials, vol. 158, No. 6, (accepted Jan. 10, 2008; available online Mar. 4, 2008), pp. 213-218.
(Continued)

Primary Examiner — Jayne L Mershon
(74) Attorney, Agent, or Firm — Lerner, David, Littenberg, Krumholz & Mentlik, LLP

(57) ABSTRACT

The present specification relates to a carbazole derivative, a coating composition comprising the carbazole derivative, an organic light emitting device using the same, and a method for manufacturing the same.

19 Claims, 12 Drawing Sheets

| 701 |
|-----|
| 601 |
| 501 |
| 401 |
| 301 |
| 201 |
| 101 |

(51) Int. Cl.
  *H01L 51/00* (2006.01)
  *H01L 51/50* (2006.01)
  *C09K 11/06* (2006.01)
  *C07D 209/82* (2006.01)
  *C07D 403/10* (2006.01)
  *C07D 487/14* (2006.01)
  *C07D 209/88* (2006.01)

(52) U.S. Cl.
  CPC ......... *C07D 403/10* (2013.01); *C07D 403/14* (2013.01); *C07D 487/14* (2013.01); *C09K 11/06* (2013.01); *H01L 51/00* (2013.01); *H01L 51/0005* (2013.01); *H01L 51/006* (2013.01); *H01L 51/0061* (2013.01); *H01L 51/0072* (2013.01); *H01L 51/50* (2013.01); *H01L 51/5024* (2013.01); *H01L 51/5056* (2013.01); *H01L 51/5088* (2013.01)

(58) Field of Classification Search
  CPC ..... C09K 11/06; H01L 51/00; H01L 51/0005; H01L 51/006; H01L 51/0061; H01L 51/0072; H01L 51/50; H01L 51/5024
  See application file for complete search history.

(56) References Cited

FOREIGN PATENT DOCUMENTS

| | | | |
|---|---|---|---|
| KR | 20100008947 | A | 1/2010 |
| KR | 20110111967 | A | 10/2011 |
| KR | 20120112277 | A | 10/2012 |
| KR | 20130080643 | A | 7/2013 |
| KR | 20150093995 | A | 8/2015 |
| KR | 20160041124 | * | 4/2016 |
| KR | 20160041124 | | 4/2016 |
| TW | 201330345 | A | 7/2013 |

OTHER PUBLICATIONS

Lengvinaite, S., et al., "Carbazol-3-yl Substituted Aromatic Amnes Containing Crosslinkable Groups as Materials for Multilayer Light Emitting Diodes." Mol., Cryst. Liq., vol. 497, 2008, pp. 164/[496]-172/[504].

Examination Report for Application No. EP 16871037.4 dated Sep. 5, 2019, 4 pages.

Taiwanese Search Report for TW Application No. 105139513, dated Oct. 18, 2018.

* cited by examiner

[FIG. 1]

| |
|---|
| 701 |
| 601 |
| 501 |
| 401 |
| 301 |
| 201 |
| 101 |

[FIG. 2]
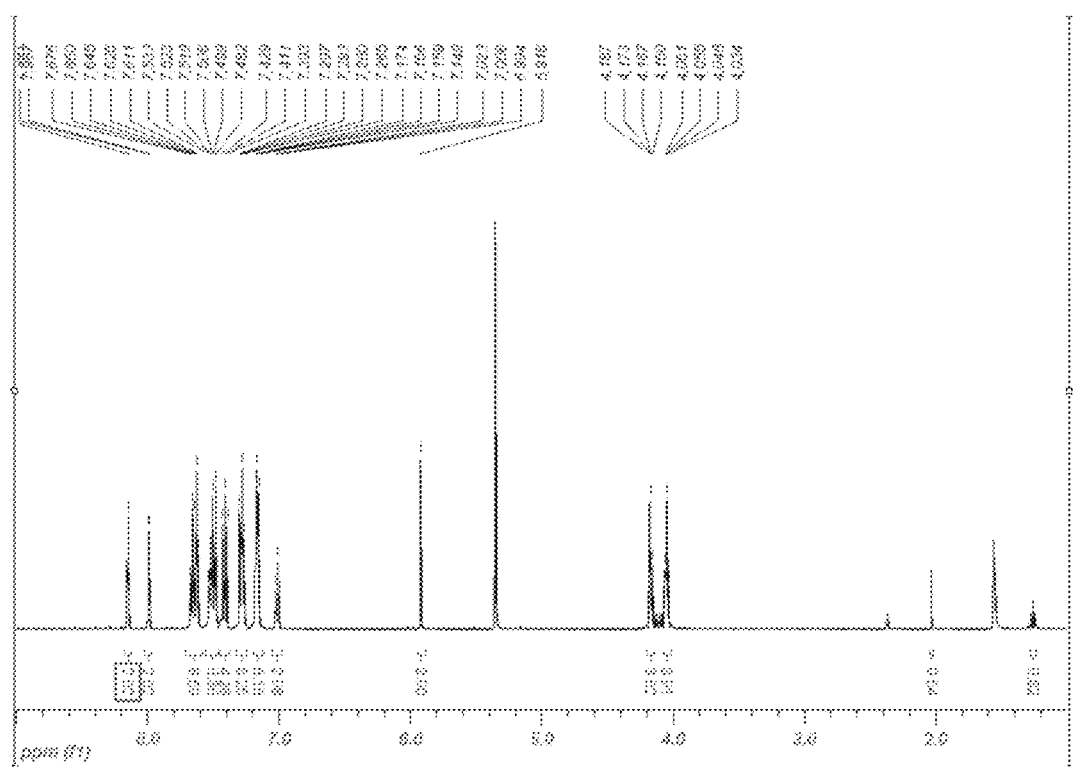

[FIG. 3]
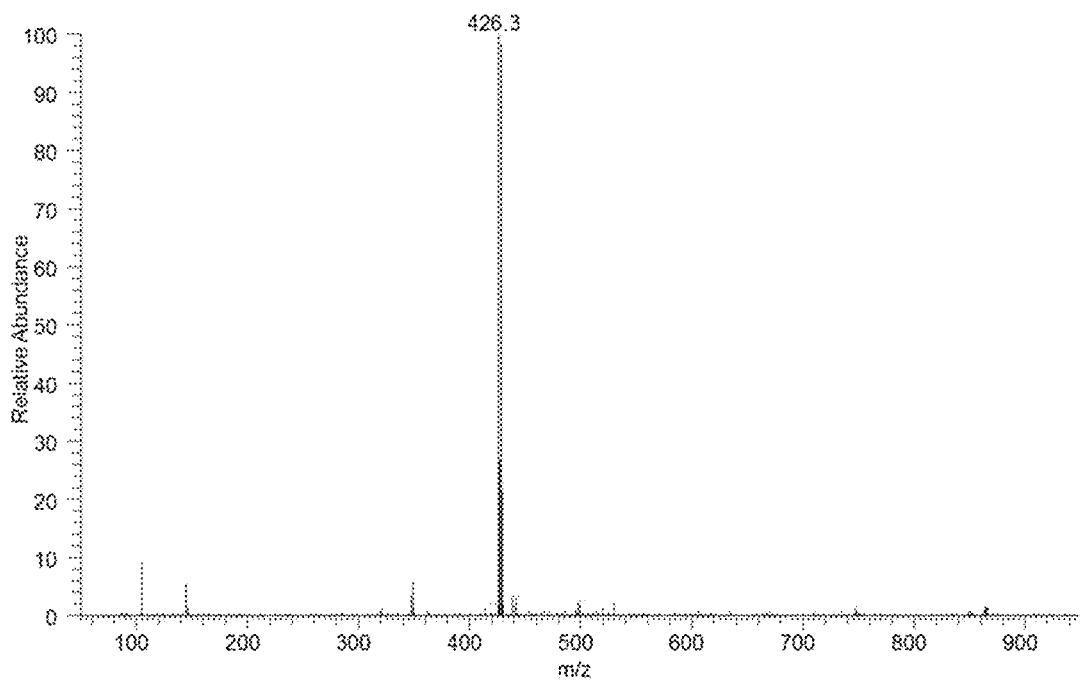

[FIG. 4]
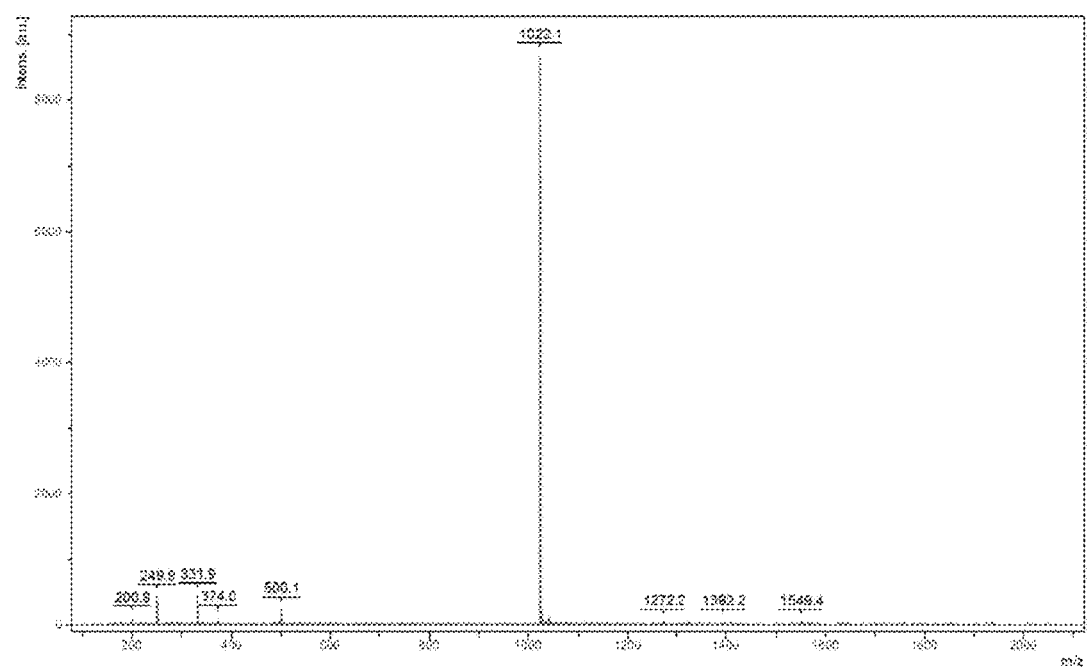

[FIG. 5]
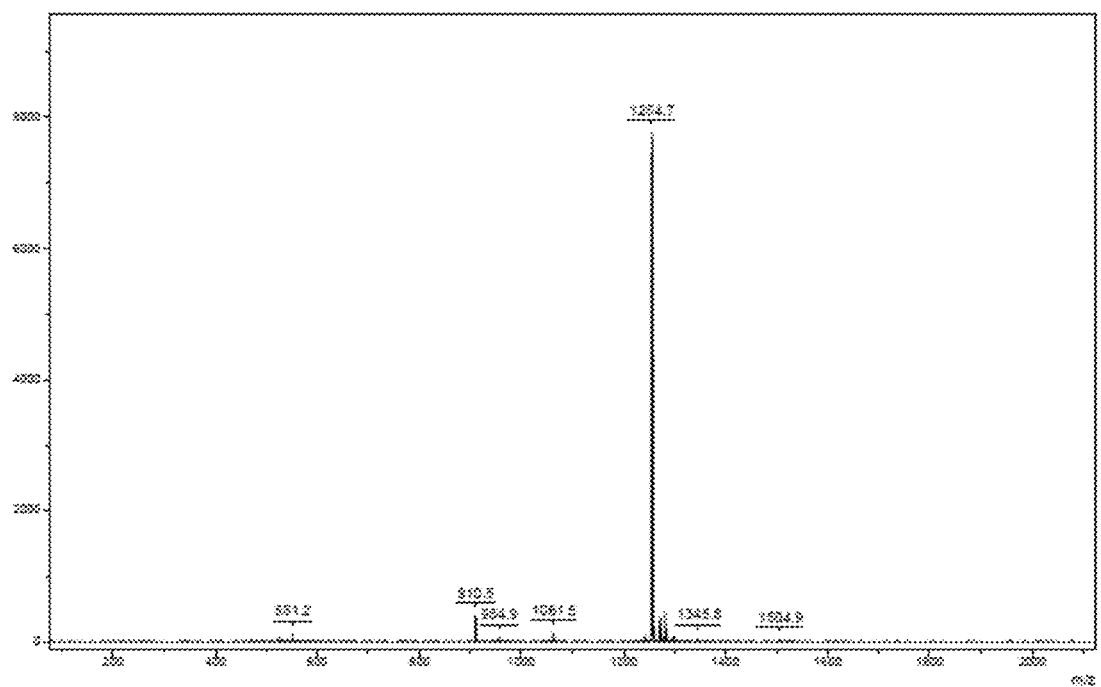

[FIG. 6]
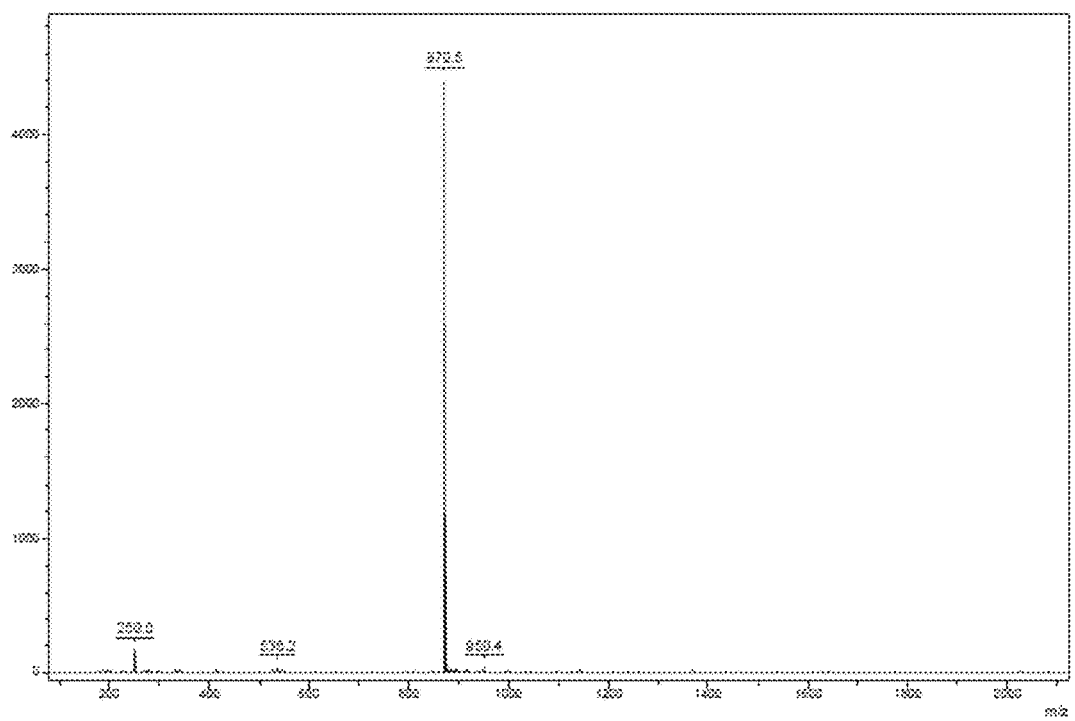

[FIG. 7]
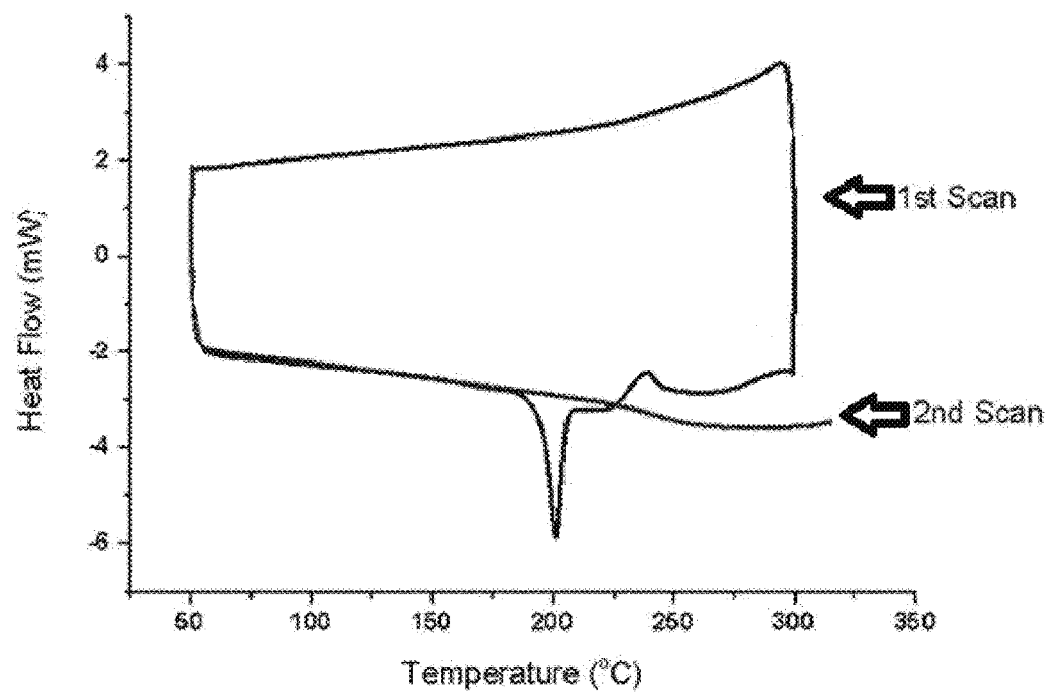

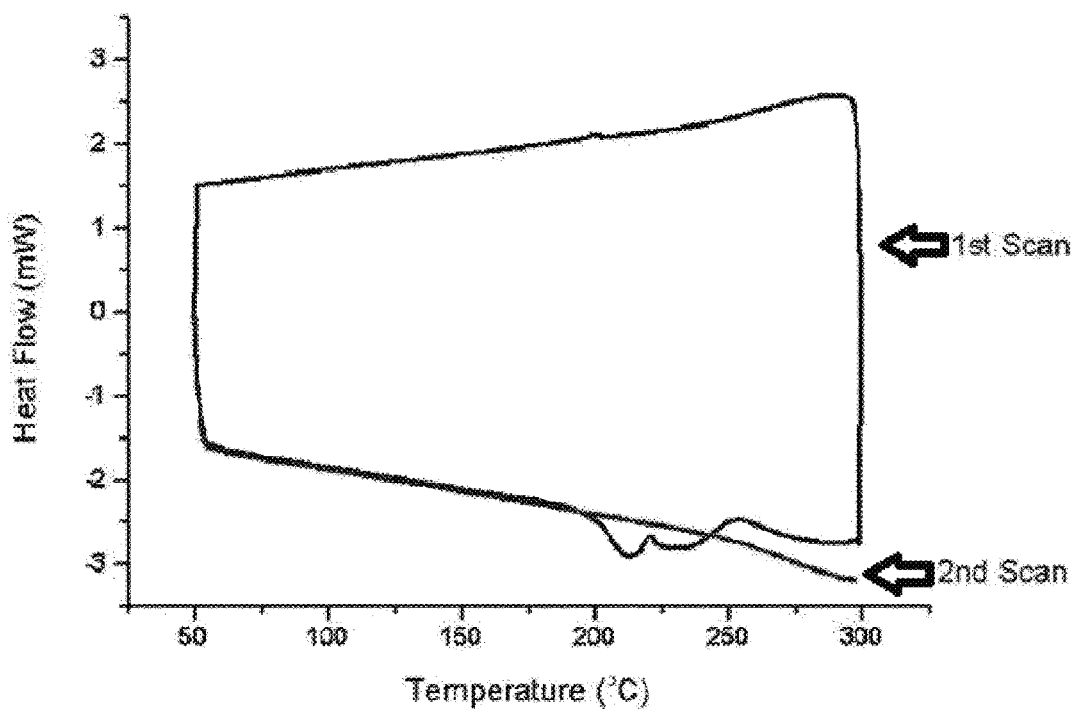
[FIG. 8]

【FIG. 9】
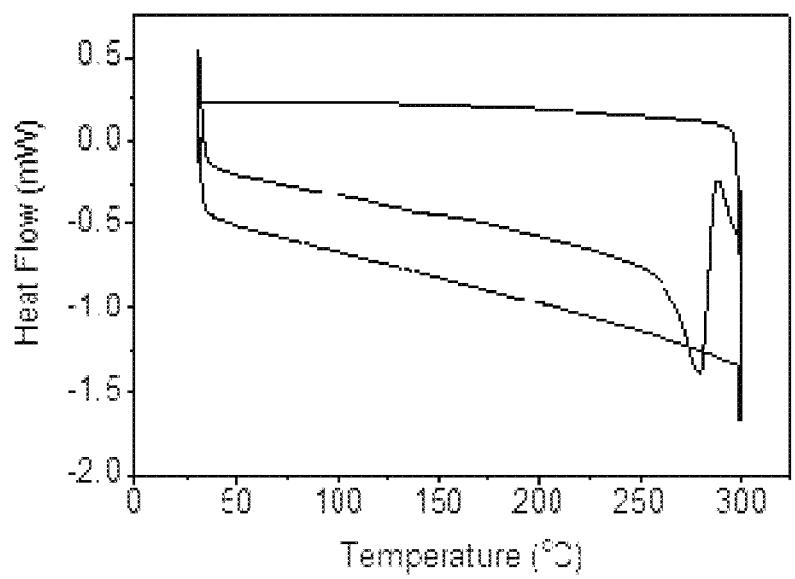
【FIG. 10】
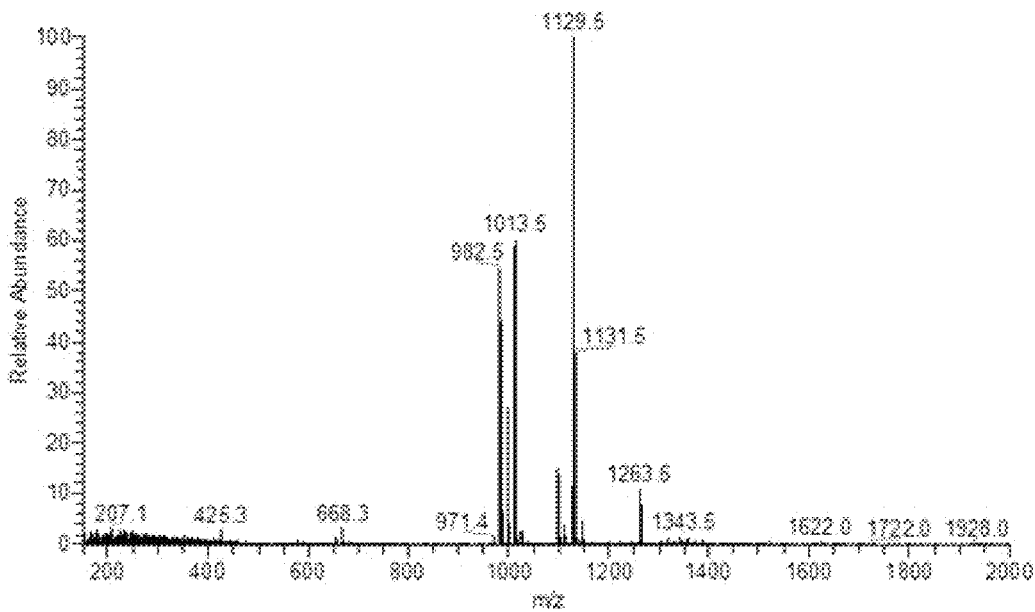

[FIG. 11]
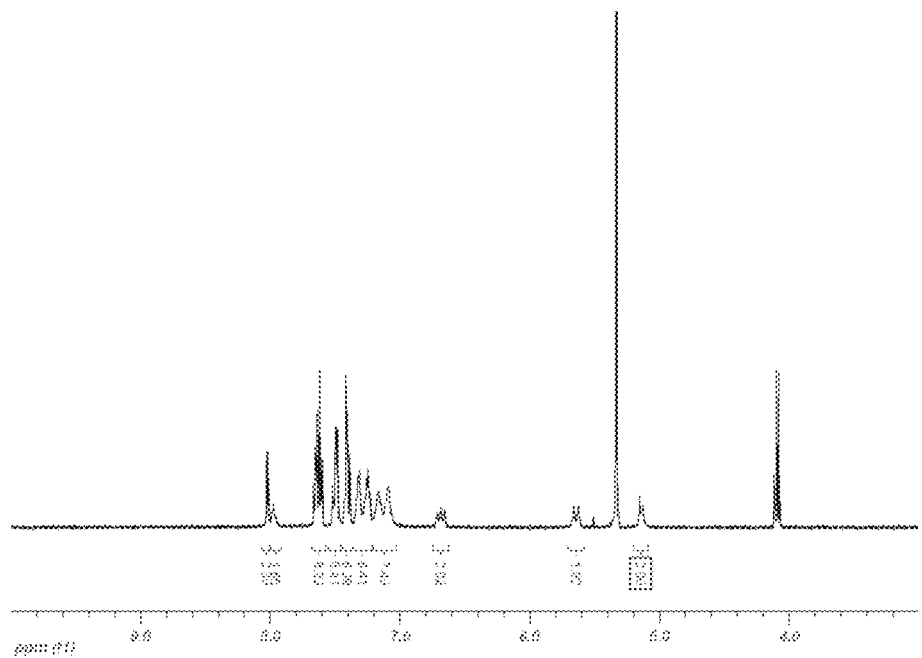

[FIG. 12]
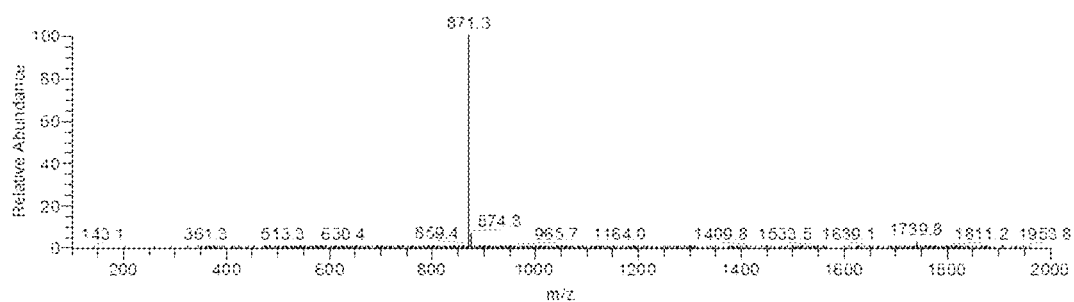
[FIG. 13]
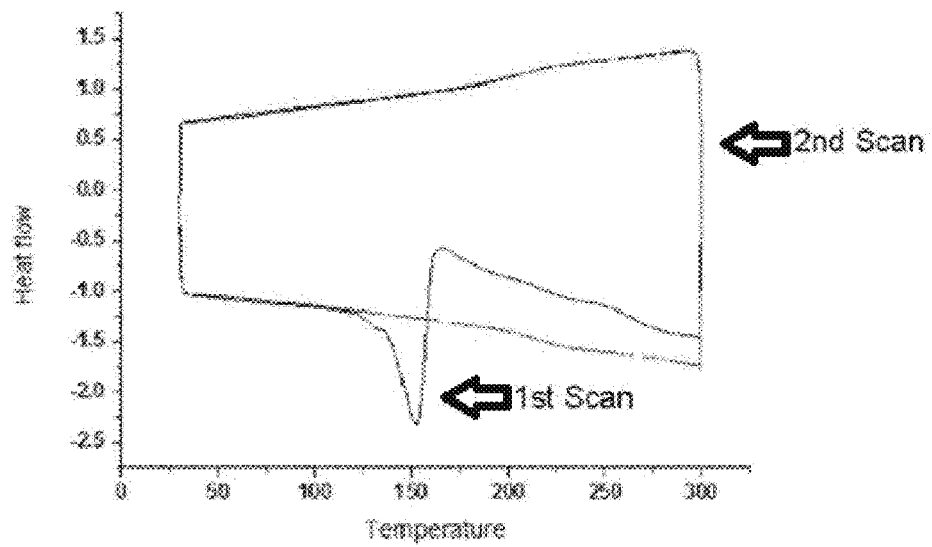

[FIG. 14]
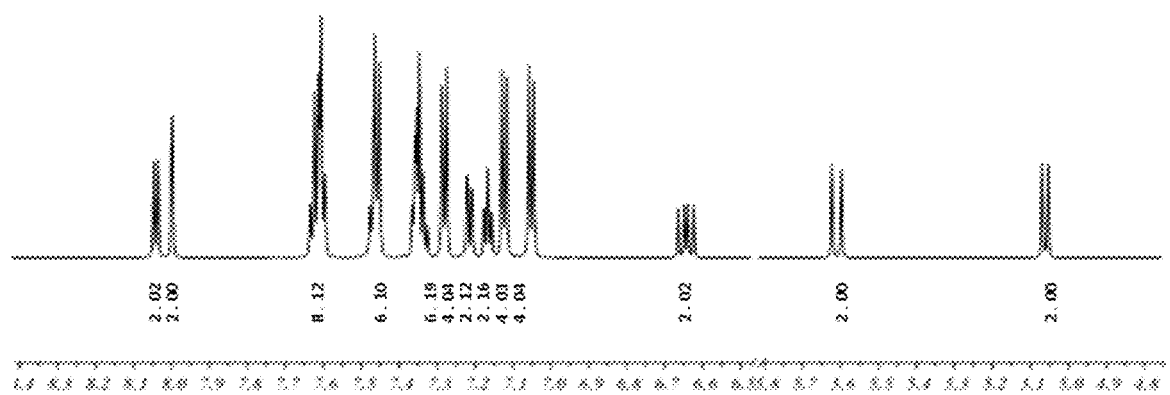
[FIG. 15]
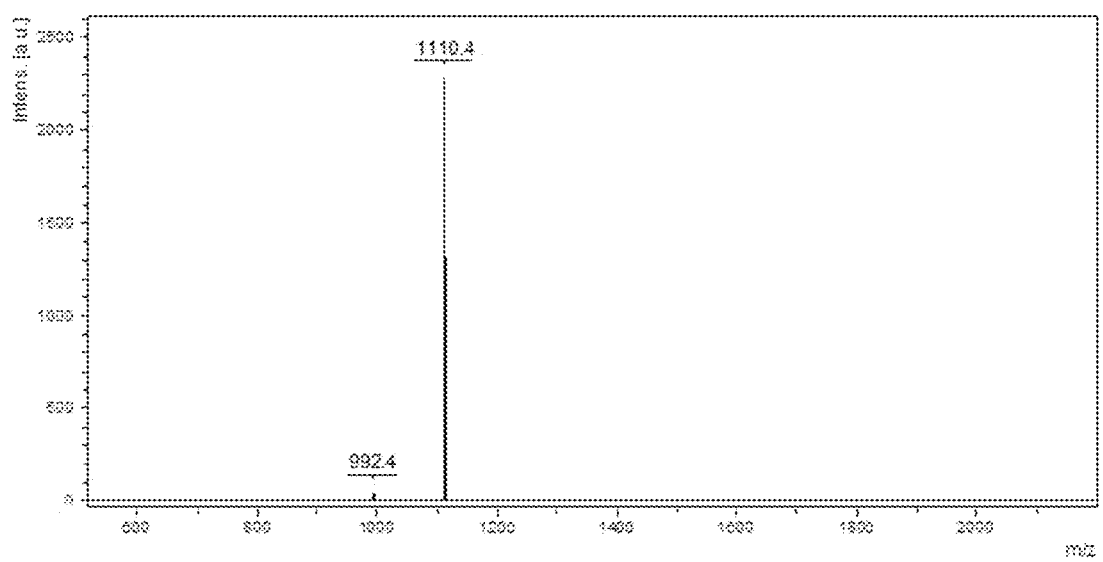

CARBAZOLE DERIVATIVE AND ORGANIC LIGHT EMITTING DEVICE USING SAME

CROSS-REFERENCE TO RELATED APPLICATIONS

The present application is a national phase entry under § 371 of International Application No. PCT/KR2016/013968 filed Nov. 30, 2016, which claims priority from Korean Patent Application No. 10-2015-0169384, filed with the Korean Intellectual Property Office on Nov. 30, 2015, and Korean Patent Application No. 10-2016-0152866, filed with the Korean Intellectual Property Office on Nov. 16, 2016, the entire contents of which are incorporated herein by reference.

TECHNICAL FIELD

The present specification relates to a carbazole derivative, a coating composition comprising the carbazole derivative, an organic light emitting device formed using the coating composition, and a method for manufacturing the same.

BACKGROUND ART

An organic light emission phenomenon is one of examples converting current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively, and the holes and the electrons injected to the organic material layer recombine to form excitons, and light emits when these excitons fall back to the ground state. An organic light emitting device using such a principle is generally formed with a cathode, an anode, and an organic material layer placed therebetween, for example, an organic material layer including a hole injection layer, a hole transfer layer, a light emitting layer and an electron transfer layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferable that materials used in an organic light emitting device additionally have properties as follows.

First, materials used in an organic light emitting device preferably have excellent thermal stability. This is due to joule heating produced by charge transfer in the organic light emitting device. NPB normally used as a hole transfer layer material currently has a glass transition temperature of 100° C. or lower, and is difficult to be used in organic light emitting devices requiring high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifespan.

In addition thereto, materials used in an organic light emitting device need to have excellent chemical stability, degree of charge transfer, and interface properties with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials need to improve an interface with electrodes including metals or metal oxides.

Accordingly, development of organic materials satisfying such requirements has been required in the art.

DISCLOSURE

Technical Problem

The present specification is directed to providing a carbazole derivative capable of being used in an organic light emitting device and satisfying conditions described above, and an organic light emitting device comprising the same.

Technical Solution

One embodiment of the present specification provides a carbazole derivative represented by the following Chemical Formula 1.

[Chemical Formula 1]

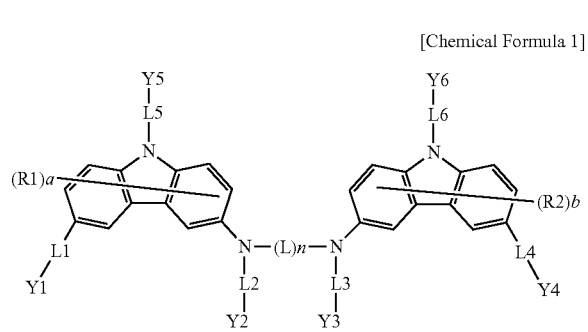

In Chemical Formula 1,

L is a substituted or unsubstituted arylene group; a substituted or unsubstituted divalent heterocyclic group; or -L7-NR'-L8-, L7 and L8 are the same as or different from each other, and each independently a substituted or unsubstituted arylene group, R' is a substituted or unsubstituted aryl group; or a substituted or unsubstituted heterocyclic group, L1 and L4 are the same as or different from each other, and each independently a direct bond; a substituted or unsubstituted arylene group; or a substituted or unsubstituted divalent heterocyclic group, L2 and L3 are the same as or different from each other, and each independently a direct bond; a substituted or unsubstituted alkylene group having 1 to 30 carbon atoms; a substituted or unsubstituted alkenylene group having 1 to 30 carbon atoms; a substituted or unsubstituted arylene group having 6 to 30 carbon atoms; or a substituted or unsubstituted divalent heterocyclic group having 2 to 30 carbon atoms, L5 and L6 are the same as or different from each other, and each independently a substituted or unsubstituted alkylene group having 1 to 30 carbon atoms; a substituted or unsubstituted alkenylene group having 1 to 30 carbon atoms; a substituted or unsubstituted arylene group having 6 to 30 carbon atoms; or a substituted or unsubstituted divalent heterocyclic group having 2 to 30 carbon atoms, a and b are each an integer of 1 to 6, when a and b are each 2 or greater, structures in the parentheses are the same as or different from each other, R1 and R2 are the same as or different from each other, and each independently hydrogen; deuterium; a substituted or unsubstituted alkyl group having 1 to 30 carbon atoms; a substituted or unsubstituted alkoxy group having 1 to 30 carbon atoms; a substituted or unsubstituted aryl group having 6 to 30 carbon atoms; a substituted or unsubstituted arylamine group; or a substituted or unsubstituted heterocyclic group having 2 to 30 carbon atoms, or adjacent substituents bond to each other to form a substituted or unsubstituted hydrocarbon ring; or a substituted or unsubstituted heterocyclic group, n is an integer of 1 to 4, when n is an integer of 2 or greater, two or more Ls are the same as or different from each other, and Y1 to Y6 are the same as or different from each other, and each independently hydrogen; or a functional group capable of crosslinking by heat or light, and at least one or more of Y1 to Y4 are a functional group capable of crosslinking by heat or light.

Another embodiment of the present specification provides a coating composition comprising the carbazole derivative.

Still another embodiment of the present specification provides an organic light emitting device comprising a cathode; an anode; and one or more organic material layers provided between the cathode and the anode, wherein one or more layers of the organic material layers are formed using the coating composition.

Lastly, yet another embodiment of the present specification provides a method for manufacturing an organic light emitting device comprising preparing a substrate; forming a cathode or an anode on the substrate; forming one or more organic material layers on the cathode or the anode; and forming an anode or a cathode on the organic material layers, wherein one or more layers of the organic material layers are formed using the coating composition.

Advantageous Effects

A carbazole derivative according to one embodiment of the present specification is capable of a solution process, and is capable of manufacturing large area devices.

A carbazole derivative according to one embodiment of the present specification is capable of being used as a material of an organic material layer of an organic light emitting device, and is capable of providing low driving voltage, high light emission efficiency and high lifespan properties.

An organic material layer formed using a carbazole derivative according to one embodiment of the present specification has excellent thermal stability.

DESCRIPTION OF DRAWINGS

FIG. 1 illustrates an example of an organic light emitting device according to one embodiment of the present specification.

FIG. 2 is a diagram showing an NMR spectrum of Chemical Formula E-1.

FIG. 3 is a diagram showing an MS spectrum of Chemical Formula C-2.

FIG. 4 is a diagram showing an MS spectrum of Chemical Formula 1-2.

FIG. 5 is a diagram showing an MS spectrum of Chemical Formula 1-5.

FIG. 6 is a diagram showing an MS spectrum of Chemical Formula 1-1.

FIG. 7 is a diagram showing a differential scanning calorimetry of Chemical Formula 1-2.

FIG. 8 is a diagram showing a differential scanning calorimetry of Chemical Formula 1-5.

FIG. 9 is a diagram showing a differential scanning calorimetry of Chemical Formula 1-25.

FIG. 10 is a diagram showing an MS spectrum of Chemical Formula 1-26.

FIG. 11 is a diagram showing an NMR spectrum of Chemical Formula 1-27.

FIG. 12 is a diagram showing an MS spectrum of Chemical Formula 1-27.

FIG. 13 is a diagram showing a differential scanning calorimetry of Chemical Formula 1-28.

FIG. 14 is a diagram showing an NMR spectrum of Chemical Formula 1-28.

FIG. 15 is a diagram showing an MS spectrum of Chemical Formula 1-28.

101: Substrate
201: Anode
301: Hole Injection Layer
401: Hole Transfer Layer
501: Light Emitting Layer
601: Electron Transfer Layer
701: Cathode

MODE FOR DISCLOSURE

Hereinafter, the present specification will be described in detail.

In the present specification, a description of one member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

In the whole present specification, the term "combination thereof" included in the expression of Markush form means a mixture of a combination of one or more selected from the group consisting of constituents described in the expression of Markush form, and means including one or more selected from the group consisting of the constituents.

One embodiment of the present specification provides a carbazole derivative represented by Chemical Formula 1.

In one embodiment of the present specification, Y1 to Y6 are the same as or different from each other, and each independently hydrogen; or a functional group capable of crosslinking by heat or light, and at least one or more of Y1 to Y4 are a functional group capable of crosslinking by heat or light.

In the present specification, "functional group capable of crosslinking" may mean a reactive substituent crosslinking compounds by being exposed to heat and/or light. Crosslinking may occur by heat treatment or light irradiation through the linkage of radicals generated while carbon-carbon multiple bonds or cyclic structures are decomposed.

In one embodiment of the present specification, Y1 to Y6 are the same as or different from each other, and each independently hydrogen; or any one of the following structures, and at least one or more of Y1 to Y4 are any one of the following structures.

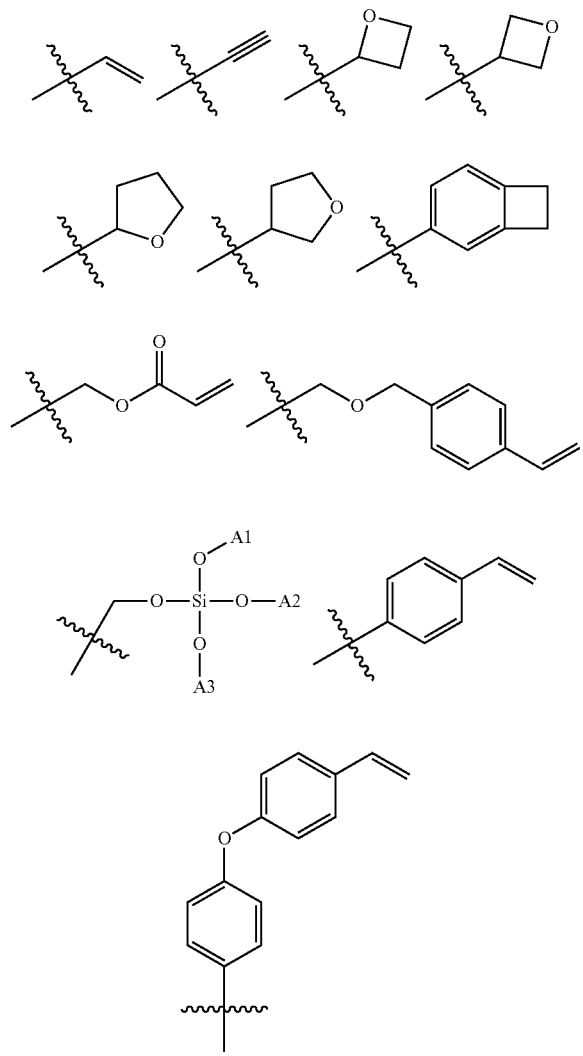

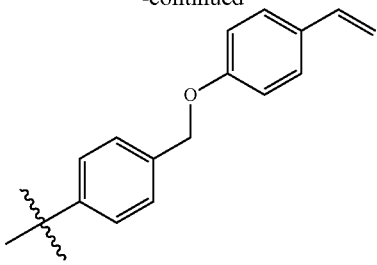

-continued

In the structures,

A1 to A3 are the same as or different from each other, and each independently a substituted or unsubstituted alkyl group having 1 to 6 carbon atoms.

As in one embodiment of the present specification, an organic light emitting device may be manufactured using a solution coating method with the carbazole derivative comprising a functional group capable of crosslinking, and therefore, it is economically effective in terms of time and costs.

In addition, when a coating layer is formed using a coating composition comprising the carbazole derivative comprising a functional group capable of crosslinking, the functional group capable of crosslinking forms crosslinkage by heat or light, and therefore, the carbazole derivative included in the coating composition being washed away by a solvent is prevented when laminating additional layers on the top of the coating layer, and accordingly, additional layers may be laminated on the top of the coating layer while the coating layer is retained.

Additionally, when the functional group capable of crosslinking forms crosslinkage to form a coating layer, chemical resistance of the coating layer for a solvent increases, and an effect of high membrane retention rate is obtained.

In addition, an organic light emitting device may be manufactured using a solution coating method with the carbazole derivative according to one embodiment of the present specification, and therefore, devices having large areas are capable of being manufactured.

According to one embodiment of the present specification, the carbazole derivative forming crosslinkage by heat treatment or light treatment is provided in an organic light emitting device in a thin film form with a plurality of the carbazole derivatives being crosslinked, and therefore, is effective in exhibiting excellent thermal stability is obtained. Accordingly, an organic light emitting device using the carbazole derivative according to one embodiment of the present specification is effective in exhibiting excellent lifespan properties.

In addition, the carbazole derivative according to one embodiment of the present specification comprises an amine structure in the core structure, and therefore, may have suitable energy level and band gap as a hole injection, hole transfer or light emitting material in an organic light emitting device. Furthermore, the suitable energy level and band gap may be finely adjusted by controlling substituents of the compound of Chemical Formula 1 according to one embodiment of the present specification, and by enhancing interfacial properties between organic materials, an organic light emitting device having low driving voltage and high light emission efficiency may be provided.

Hereinafter, substituents of the present specification will be described in detail.

In the present specification,

means a site bonding to other substituents or bonding sites.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of hydrogen; deuterium; a halogen group; a nitrile group; a nitro group; a hydroxyl group; an alkyl group; an alkoxy group; an alkenyl group; an aryl group; an amine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, examples of the halogen group may include fluorine, chlorine, bromine or iodine.

In the present specification, the alkyl group may be linear, branched or cyclic, and the number of carbon atoms is not particularly limited, but is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

The alkyl group may be substituted with an aryl group or a heteroaryl group to function as an arylalkyl group or a heteroarylalkyl group. The aryl group or the heterocyclic group may be selected from among examples of an aryl group or a heterocyclic group to be described below.

In the present specification, the length of the alkyl group does not affect conjugation length of a compound, and may affect a method of using the compound in an organic light emitting device, for example, use of a vacuum deposition method or a solution coating method.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

The alkoxy group may be substituted with an aryl group or a heteroaryl group to function as an aryloxy group or a heteroaryloxy group. The aryl group or the heterocyclic group may be selected from among examples of an aryl group or a heterocyclic group to be described below.

In the present specification, the alkenyl group may be linear or branched, and although not particularly limited thereto, the number of carbon atoms is preferably from 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

The alkenyl group may be substituted with an aryl group or a heteroaryl group to function as an arylalkenyl group or a heteroarylalkenyl group. The aryl group or the heterocyclic group may be selected from among examples of an aryl group or a heterocyclic group to be described below.

When the aryl group is a monocyclic aryl group in the present specification, the number of carbon atoms is not particularly limited, but is preferably from 6 to 25. Specific examples of the monocyclic aryl group may include a phenyl group, a biphenyl group, a terphenyl group, a quaterphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

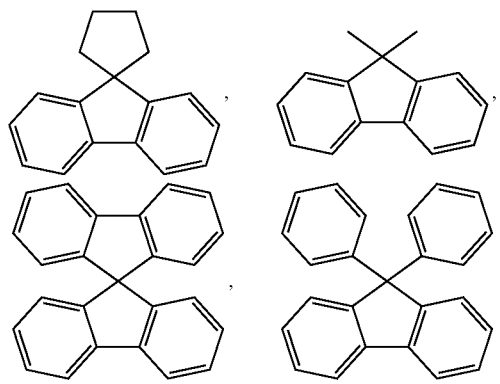

and the like may be included. However, the compound is not limited thereto.

The aryl group may be substituted with an alkyl group to function as an arylalkyl group. The alkyl group may be selected from among the examples described above.

In the present specification, the heterocyclic group includes one or more atoms that are not carbon, that is, heteroatoms, and specifically, the heteroatom may include one or more atoms selected from the group consisting of O, N, Se, S and the like. The number of carbon atoms of the heterocyclic group is not particularly limited, but is preferably from 2 to 60. Examples of the heterocyclic group may include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

The heterocyclic group may be monocyclic or multicyclic, and may be aromatic, aliphatic or a fused ring of aromatic and aliphatic.

In the present specification, the number of carbon atoms of the amine group is not particularly limited, but is preferably from 1 to 30. The amine group may be substituted with the alkyl group, the aryl group, the heterocyclic group, the alkenyl group and the cycloalkyl group described above, and combinations thereof. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, the alkylene group, the alkenylene group and the arylene group may be selected from among the examples of the alkyl group, the alkenyl group or the aryl group except that they are divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the ring formed by adjacent groups bonding to each other may be monocyclic or multicyclic, may be aliphatic, aromatic, or a fused ring of aliphatic and aromatic, and may form a hydrocarbon ring or a heteroring.

The hydrocarbon ring may be selected from among the examples of the cycloalkyl group or the aryl group except for those that are not monovalent. The heteroring may be aliphatic, aromatic, or a fused ring of aliphatic and aromatic, and may be selected from among the examples of the heterocyclic group except for those that are not monovalent.

In one embodiment of the present specification, R1 and R2 are the same as or different from each other, and each independently hydrogen; deuterium; a substituted or unsubstituted alkyl group having 1 to 30 carbon atoms; or a substituted or unsubstituted aryl group having 6 to 30 carbon atoms.

In another embodiment, R1 and R2 are the same as or different from each other, and each independently hydrogen; deuterium; or a substituted or unsubstituted alkyl group having 1 to 30 carbon atoms.

In another embodiment, adjacent substituents among a plurality of R1s bond to each other to form a substituted or unsubstituted hydrocarbon ring; or a substituted or unsubstituted heterocyclic group.

In one embodiment, adjacent substituents among a plurality of R1s form a substituted or unsubstituted hydrocarbon ring.

In another embodiment, adjacent substituents among a plurality of R1s form a substituted or unsubstituted hydrocarbon ring having 6 to 30 carbon atoms.

In another embodiment, adjacent substituents among a plurality of R1s form a substituted or unsubstituted benzene ring.

In another embodiment, adjacent substituents among a plurality of R1s form a benzene ring.

In another embodiment, adjacent substituents among a plurality of R2s bond to each other to form a substituted or unsubstituted hydrocarbon ring; or a substituted or unsubstituted heterocyclic group.

In one embodiment, adjacent substituents among a plurality of R2s form a substituted or unsubstituted hydrocarbon ring.

In another embodiment, adjacent substituents among a plurality of R2s form a substituted or unsubstituted hydrocarbon ring having 6 to 30 carbon atoms.

In another embodiment, adjacent substituents among a plurality of R2s form a substituted or unsubstituted benzene ring.

In another embodiment, adjacent substituents among a plurality of R2s form a benzene ring.

In one embodiment of the present specification, R1 is hydrogen.

In another embodiment, R2 is hydrogen.

In one embodiment of the present specification, L1 and L4 are the same as or different from each other, and each independently a direct bond; a substituted or unsubstituted arylene group; or a substituted or unsubstituted divalent heterocyclic group.

In one embodiment of the present specification, L1 and L4 are the same as or different from each other, and each independently a direct bond; a substituted or unsubstituted arylene group having 6 to 30 carbon atoms; or a substituted or unsubstituted divalent heterocyclic group having 2 to 30 carbon atoms.

In one embodiment of the present specification, L1 and L4 are the same as or different from each other, and each independently a direct bond; or a substituted or unsubstituted arylene group having 6 to 30 carbon atoms.

In one embodiment of the present specification, L1 and L4 are the same as or different from each other, and each independently a direct bond; or a substituted or unsubstituted phenylene group.

In one embodiment of the present specification, L1 is a direct bond.

In another embodiment, L1 is a substituted or unsubstituted arylene group having 6 to 30 carbon atoms.

In another embodiment, L1 is a substituted or unsubstituted phenylene group.

In another embodiment, L1 is a phenylene group.

In one embodiment of the present specification, L4 is a direct bond.

In another embodiment, L4 is a substituted or unsubstituted arylene group having 6 to 30 carbon atoms. In another embodiment, L4 is a substituted or unsubstituted phenylene group.

In another embodiment, L4 is a phenylene group.

In another embodiment, L2 and L3 are the same as or different from each other, and each independently a direct bond; a substituted or unsubstituted arylene group having 6 to 30 carbon atoms; or a substituted or unsubstituted heterocyclic group having 2 to 30 carbon atoms.

In one embodiment of the present specification, L2 and L3 are the same as or different from each other, and each independently a substituted or unsubstituted phenylene group; a substituted or unsubstituted biphenylene group; a substituted or unsubstituted naphthylene group; or a substituted or unsubstituted fluorenylene group.

In one embodiment of the present specification, L2 and L3 are a direct bond.

In another embodiment, L2 is a substituted or unsubstituted phenylene group.

In another embodiment, L2 is a phenylene group.

In one embodiment of the present specification, L2 is a phenylene group substituted with an alkyl group.

In one embodiment, L2 is a phenyl group substituted with an alkyl group having 1 to 20 carbon atoms.

In another embodiment, L2 is a phenyl group substituted with a methyl group.

In another embodiment, L2 is a substituted or unsubstituted biphenyl group.

In another embodiment, L2 is a biphenyl group.

In another embodiment, L2 is a substituted or unsubstituted naphthyl group.

In another embodiment, L2 is a naphthyl group.

In one embodiment of the present specification, L2 is a substituted or unsubstituted fluorenyl group.

In another embodiment, L2 is a fluorenyl group unsubstituted or substituted with an alkyl group.

In another embodiment, L2 is a fluorenyl group substituted with an alkyl group having 1 to 20 carbon atoms.

In another embodiment, L2 is a fluorenyl group substituted with a methyl group.

In one embodiment of the present specification, L3 is a substituted or unsubstituted aryl group.

In another embodiment, L3 is a substituted or unsubstituted aryl group having 6 to 30 carbon atoms.

In another embodiment, L3 is a substituted or unsubstituted phenyl group.

In another embodiment, L3 is a phenyl group.

In one embodiment of the present specification, L3 is a phenyl group substituted with an alkyl group.

In one embodiment, L3 is a phenyl group substituted with an alkyl group having 1 to 20 carbon atoms.

In another embodiment, L3 is a phenyl group substituted with a methyl group.

In another embodiment, L3 is a substituted or unsubstituted biphenyl group.

In another embodiment, L3 is a biphenyl group.

In another embodiment, L3 is a substituted or unsubstituted naphthyl group.

In another embodiment, L3 is a naphthyl group.

In one embodiment of the present specification, L3 is a substituted or unsubstituted fluorenyl group.

In another embodiment, L3 is a fluorenyl group unsubstituted or substituted with an alkyl group.

In another embodiment, L3 is a fluorenyl group substituted with an alkyl group having 1 to 20 carbon atoms.

In another embodiment, L3 is a fluorenyl group substituted with a methyl group.

In one embodiment of the present specification, L5 and L6 are the same as or different from each other, and each independently a substituted or unsubstituted arylene group having 6 to 30 carbon atoms.

According to one embodiment of the present specification, L5 and L6 are the same as or different from each other, and each independently a substituted or unsubstituted phenylene group.

In one embodiment of the present specification, n is 1.

In another embodiment, n is 2.

In one embodiment of the present specification, L is a substituted or unsubstituted arylene group; a substituted or unsubstituted divalent heterocyclic group; or -L7-NR'-L8-.

In one embodiment of the present specification, L is a substituted or unsubstituted arylene group having 6 to 30 carbon atoms.

In another embodiment, L is a substituted or unsubstituted phenylene group; a substituted or unsubstituted biphenylene group; or a substituted or unsubstituted fluorenylene group.

In one embodiment of the present specification, L is a phenylene group.

In another embodiment, L is a biphenylylene group.

In another embodiment, L is a fluorenylene group substituted with an alkyl group.

In another embodiment, L is a fluorenylene group substituted with an alkyl group having 1 to 20 carbon atoms.

In one embodiment of the present specification, L is a fluorenylene group substituted with a methyl group.

In one embodiment of the present specification, L is a substituted or unsubstituted divalent heterocyclic group.

In one embodiment of the present specification, L is a substituted or unsubstituted divalent heterocyclic group including one or more N atoms.

In another embodiment, L is a substituted or unsubstituted divalent heterocyclic group having 2 to 30 carbon atoms including one or more N atoms.

In one embodiment, L is a substituted or unsubstituted carbazolylene group.

In one embodiment of the present specification, L is a carbazolylene group unsubstituted or substituted with an aryl group having 6 to 30 carbon atoms.

In one embodiment, L is a carbazolylene group substituted with a phenyl group.

In one embodiment of the present specification, L is -L7-NR'-L8-.

In one embodiment of the present specification, L7 and L8 are the same as or different from each other, and each independently a substituted or unsubstituted arylene group having 6 to 30 carbon atoms.

In another embodiment, L7 and L8 are the same as or different from each other, and each independently a substituted or unsubstituted phenylene group.

In another embodiment, L7 and L8 are a phenylene group.

In one embodiment of the present specification, R' is a substituted or unsubstituted aryl group having 6 to 30 carbon atoms; or a substituted or unsubstituted heterocyclic group having 2 to 30 carbon atoms.

In one embodiment of the present specification, R' is a substituted or unsubstituted aryl group having 6 to 30 carbon atoms.

In another embodiment, R' is a substituted or unsubstituted phenyl group.

According to another embodiment, R' is a phenyl group.

In one embodiment of the present specification, the carbazole derivative represented by Chemical Formula 1 is represented by any one of the following Chemical Formulae 1-1 to 1-32.

Chemical Formula 1-1

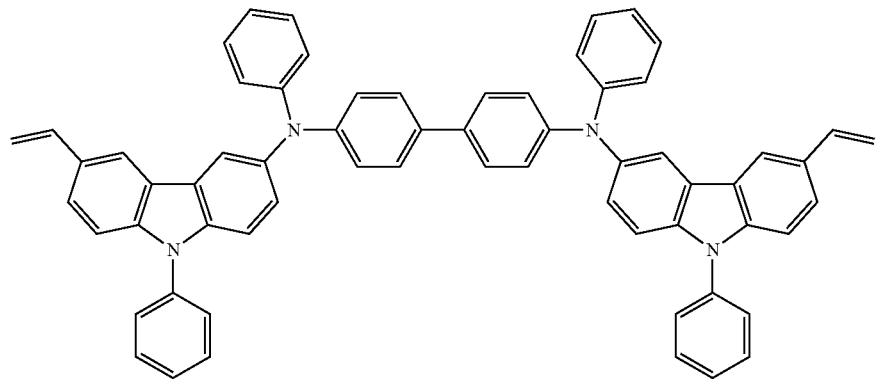

Chemical Formula 1-2

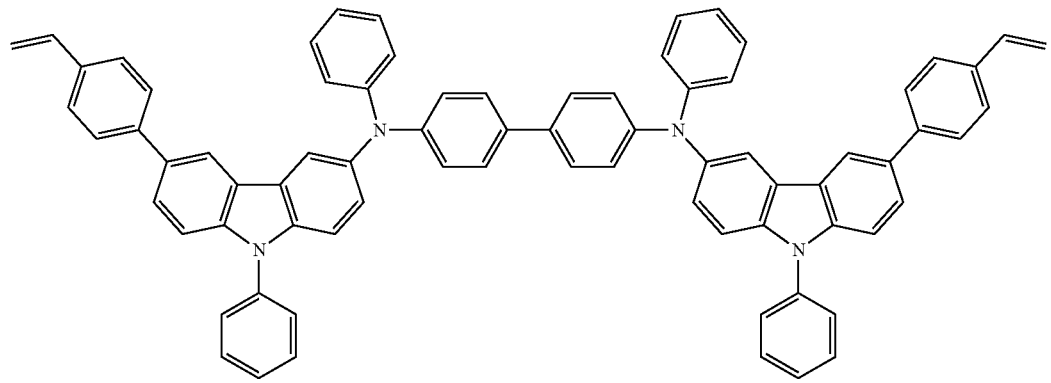

Chemical Formula 1-3

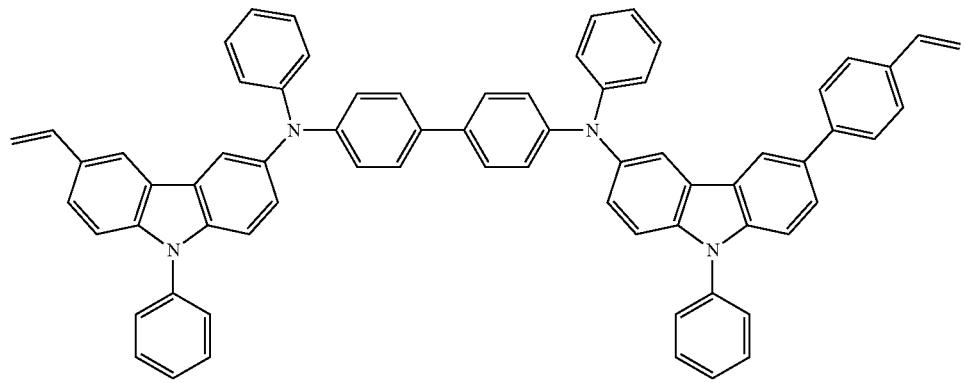

Chemical Formula 1-4
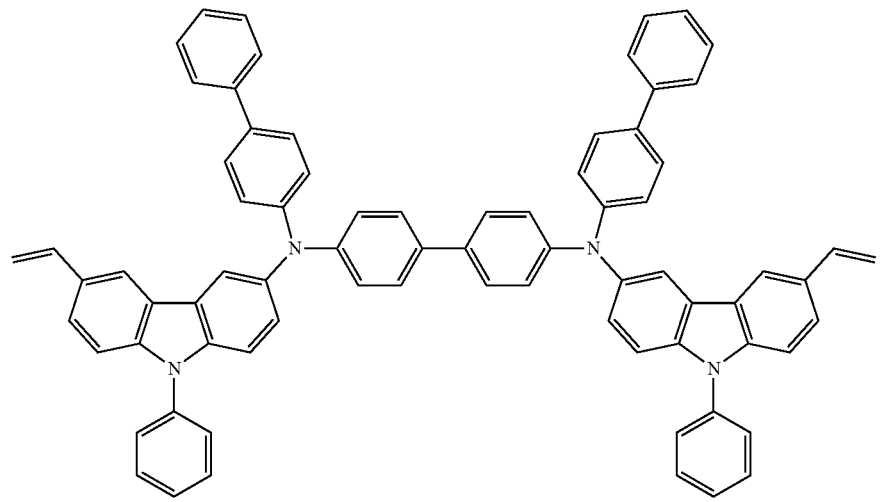
Chemical Formula 1-5
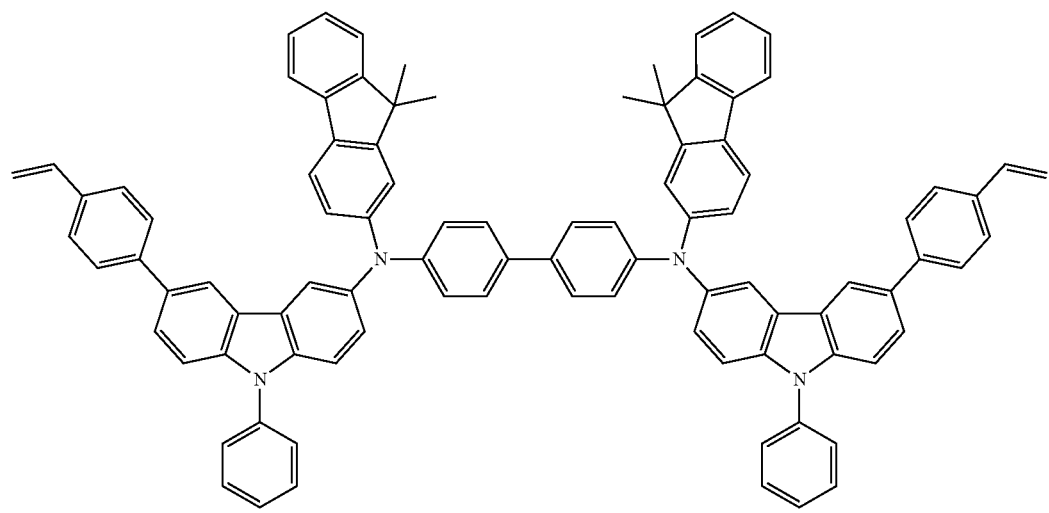
Chemical Formula 1-6
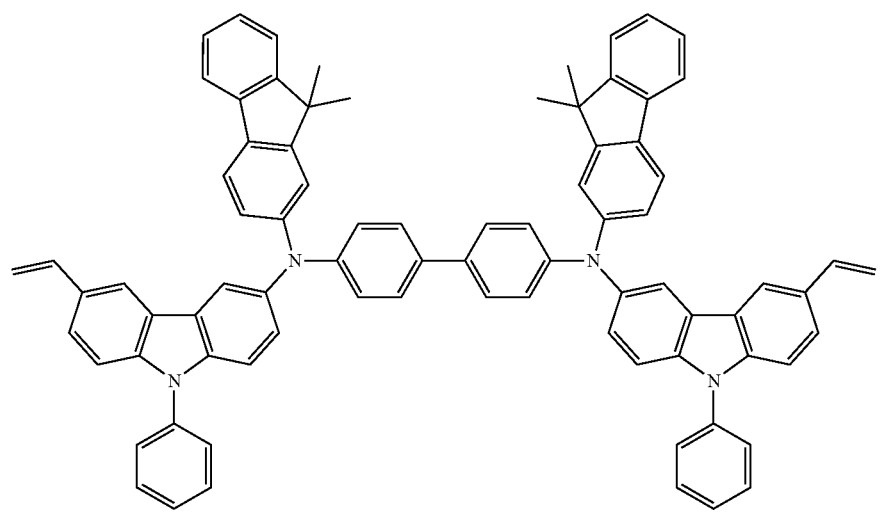

Chemical Formula 1-7
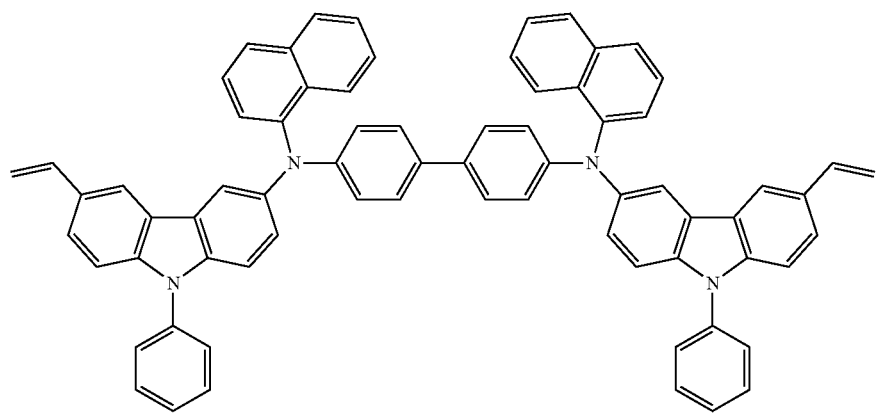
Chemical Formula 1-8
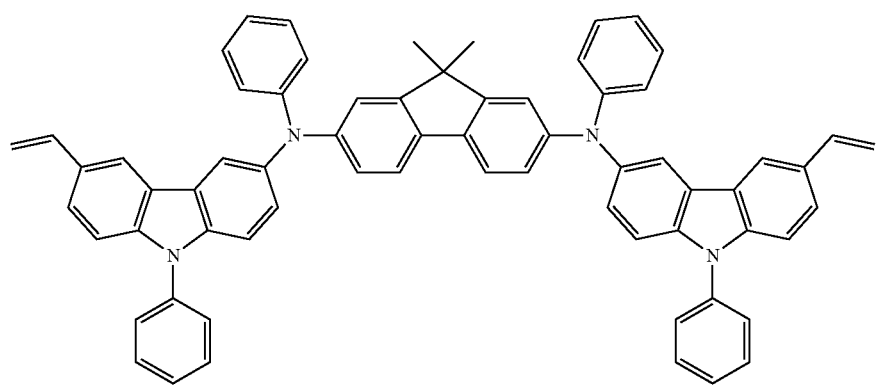
Chemical Formula 1-9
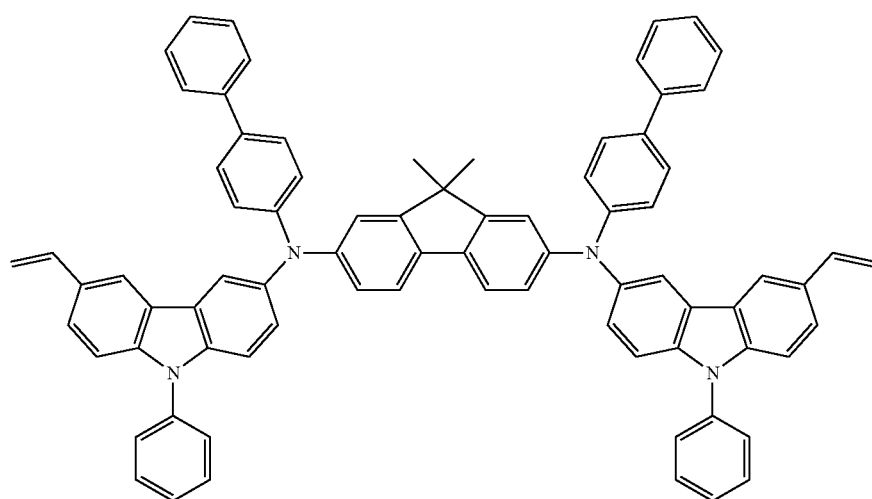

Chemical Formula 1-10
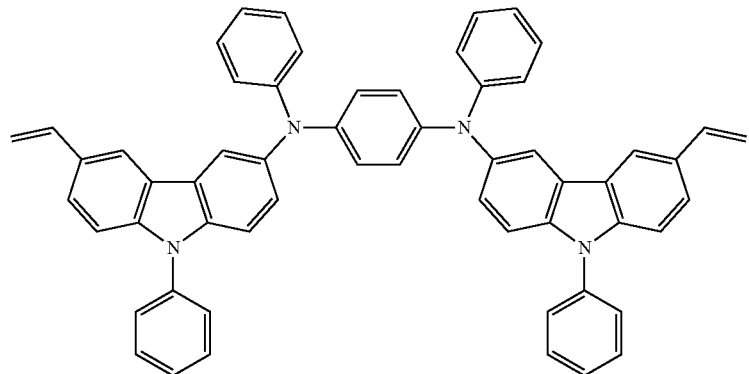
Chemical Formula 1-11
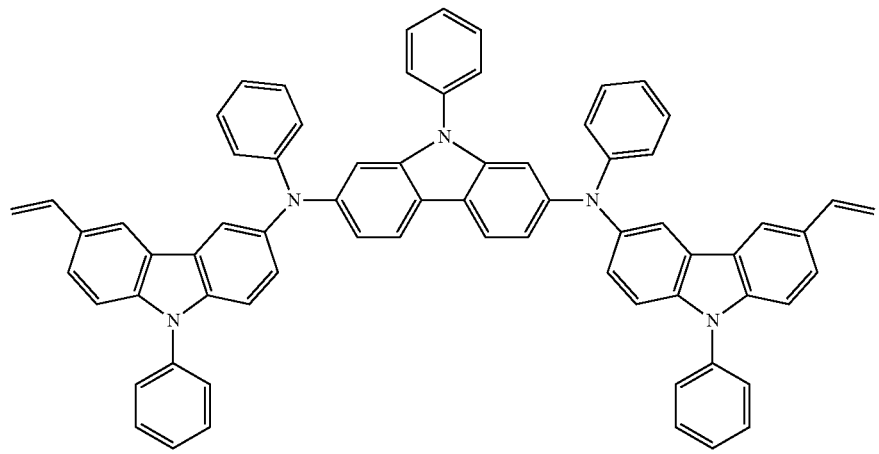
Chemical Formula 1-12
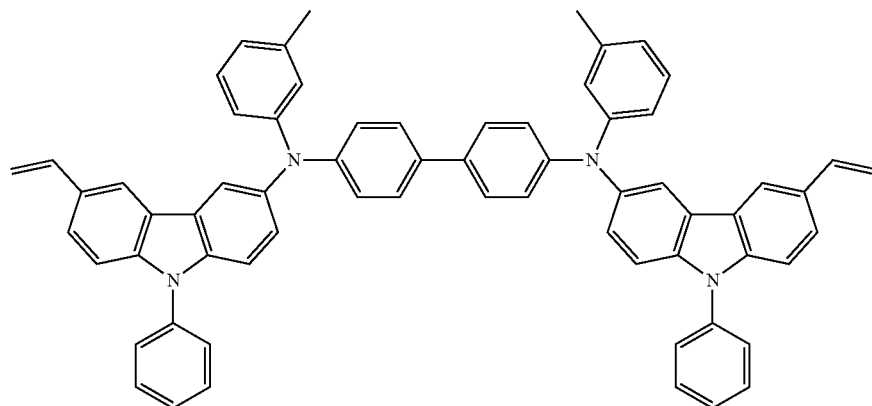
Chemical Formula 1-13
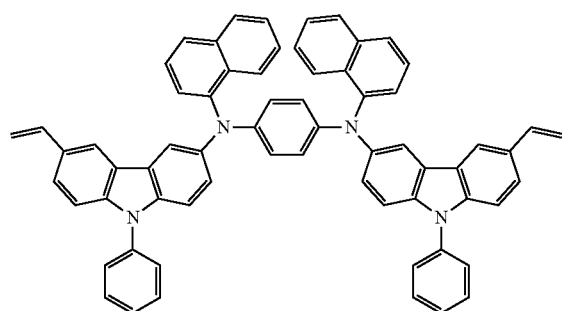
Chemical Formula 1-14
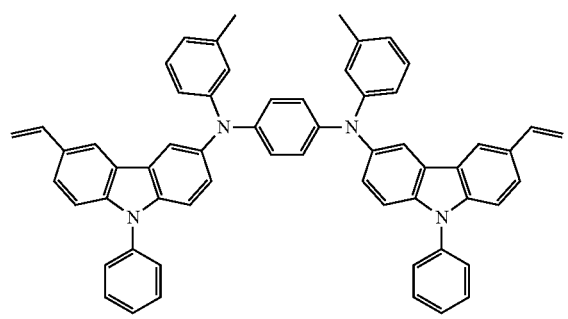

-continued
Chemical Formula 1-15
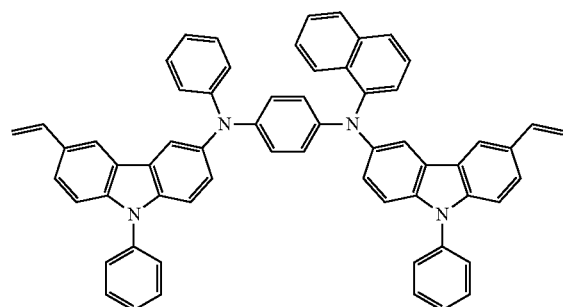
Chemical Formula 1-16
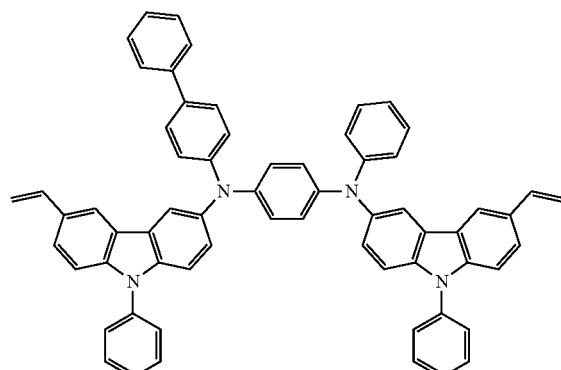
Chemical Formula 1-17
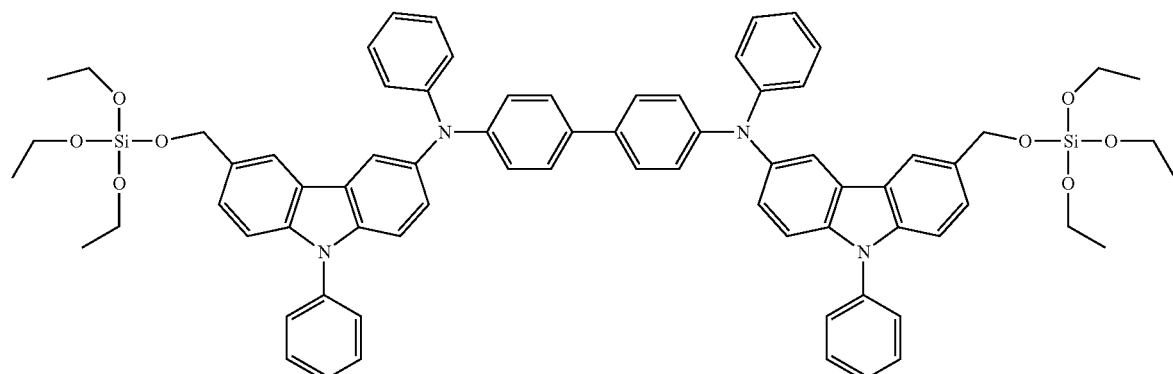
Chemical Formula 1-18
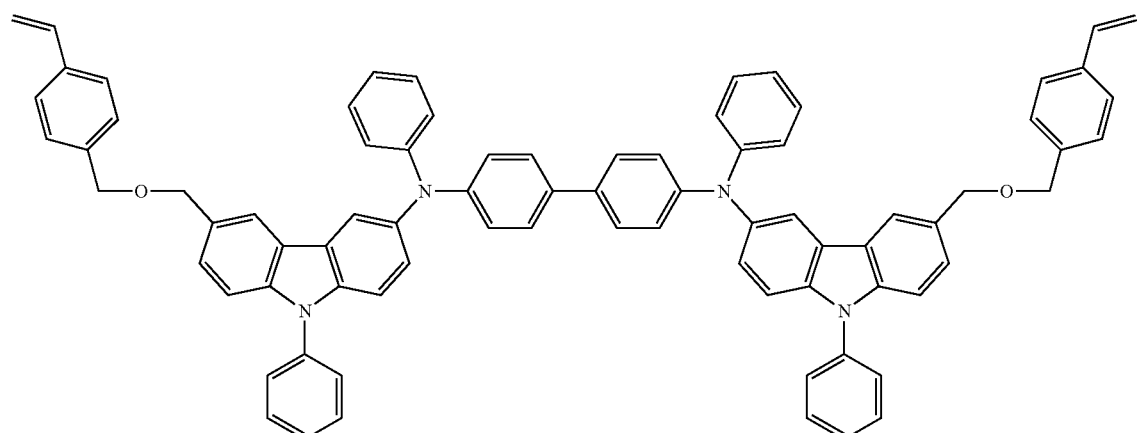
Chemical Formula 1-19
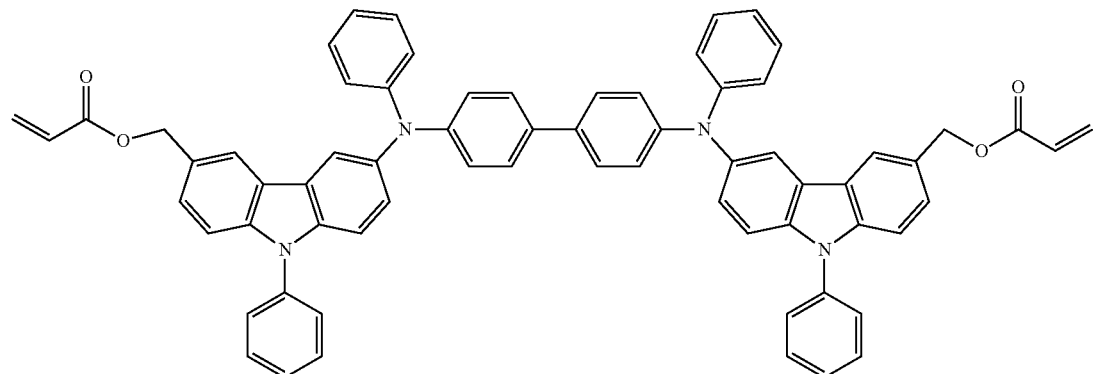

-continued
Chemical Formula 1-20
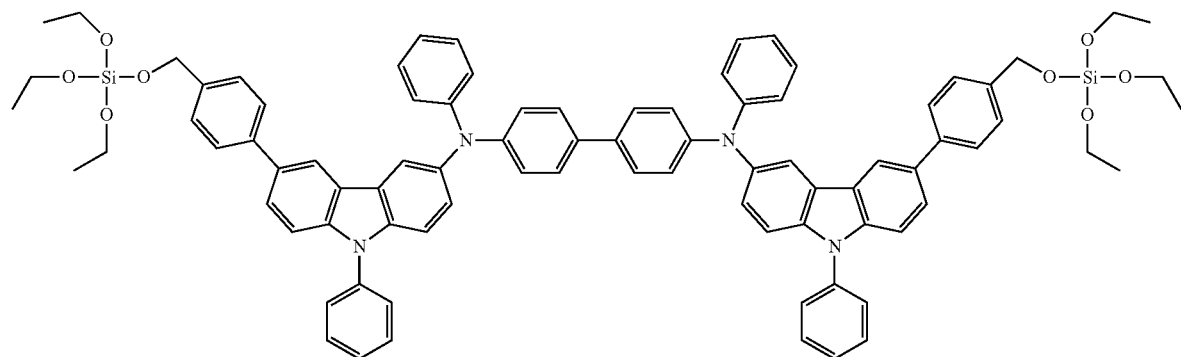
Chemical Formula 1-21
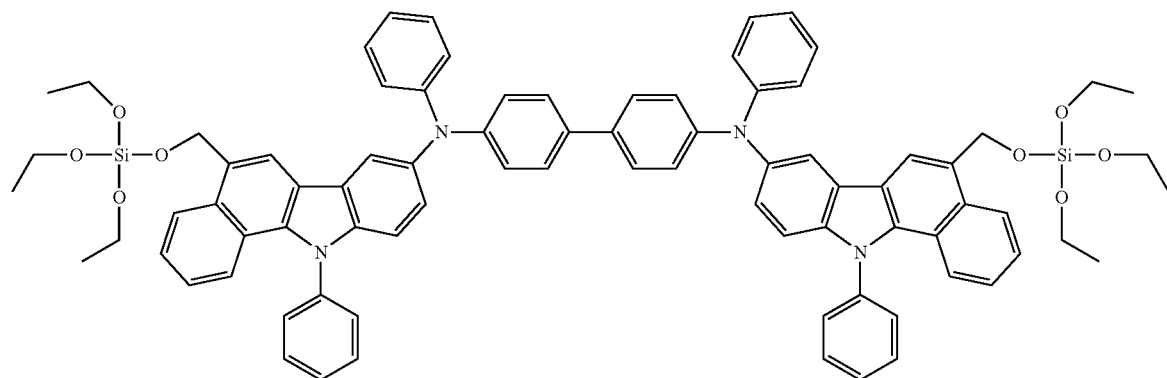
Chemical Formula 1-22
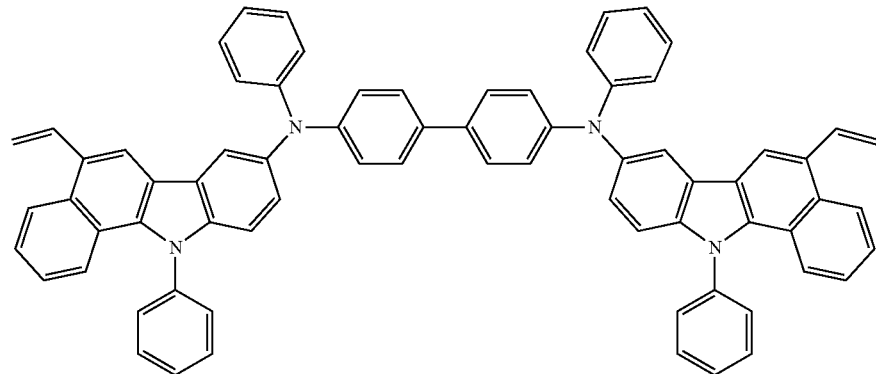
Chemical Formula 1-23
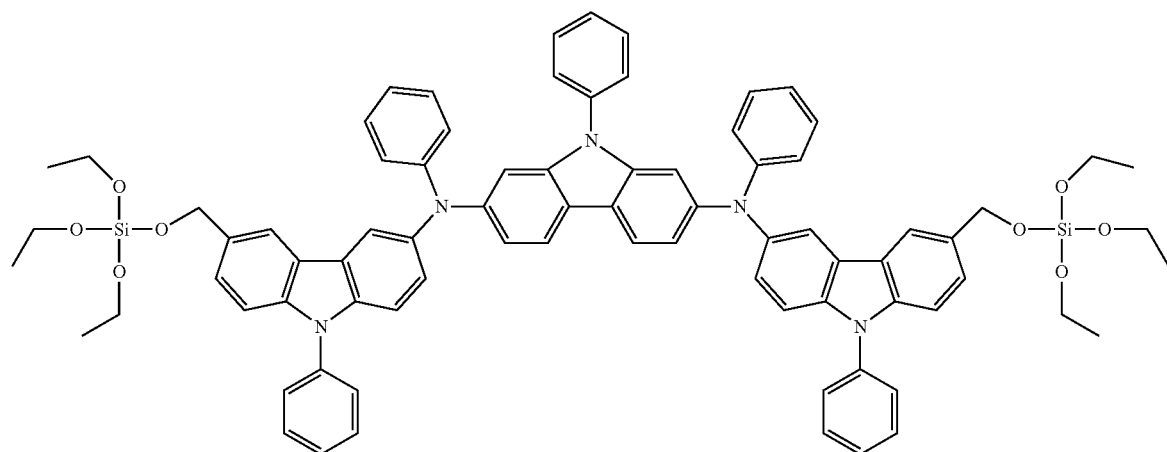

Chemical Formula 1-24
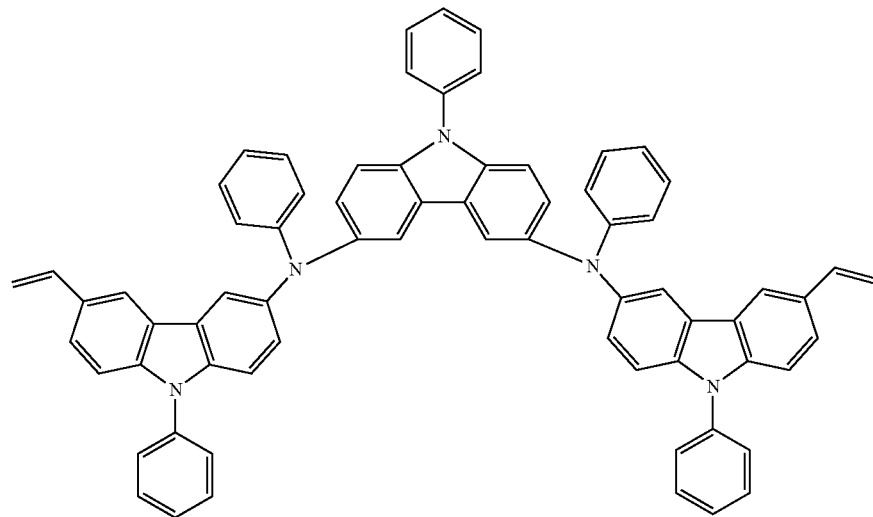
Chemical Formula 1-25
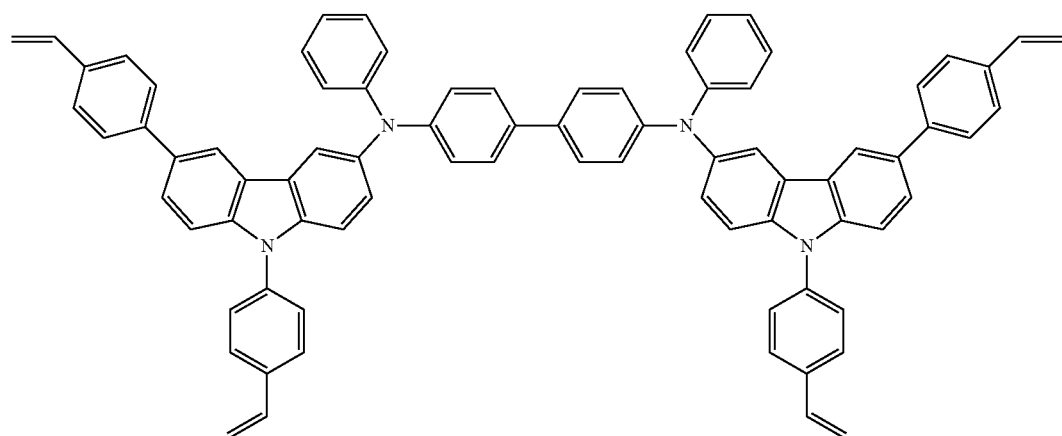
Chemical Formula 1-26
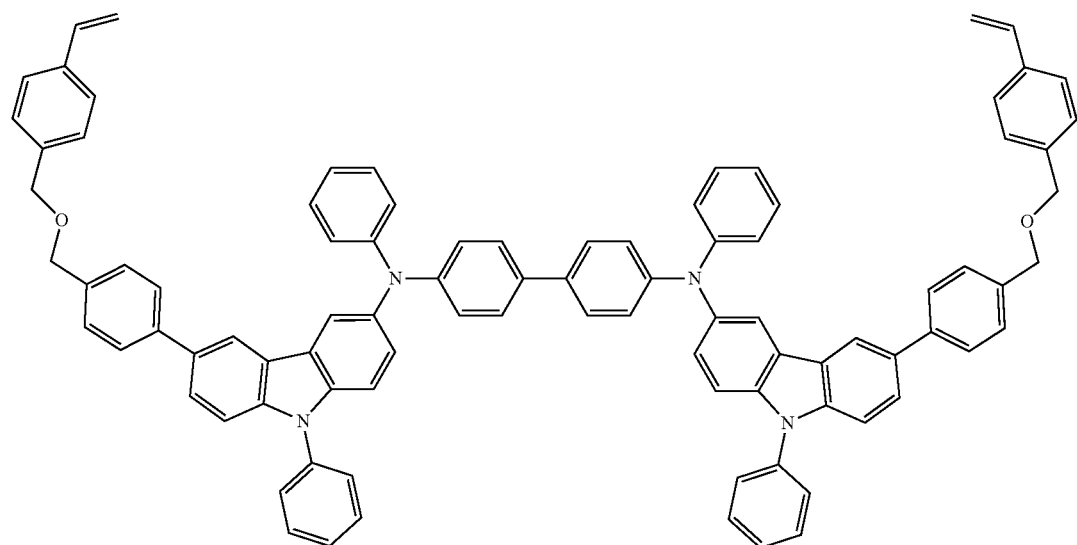

Chemical Formula 1-27
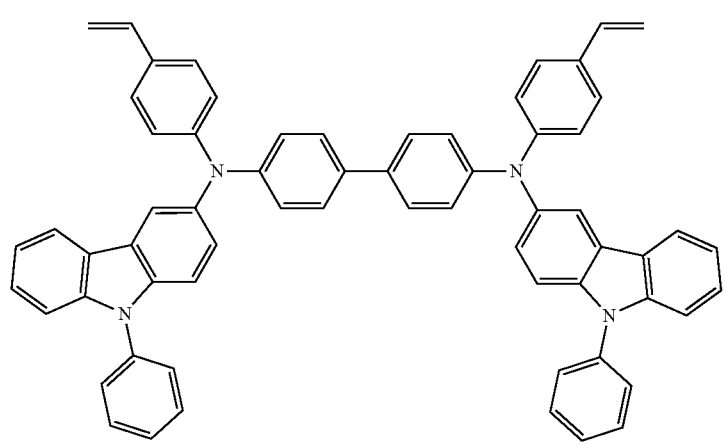
Chemical Formula 1-28
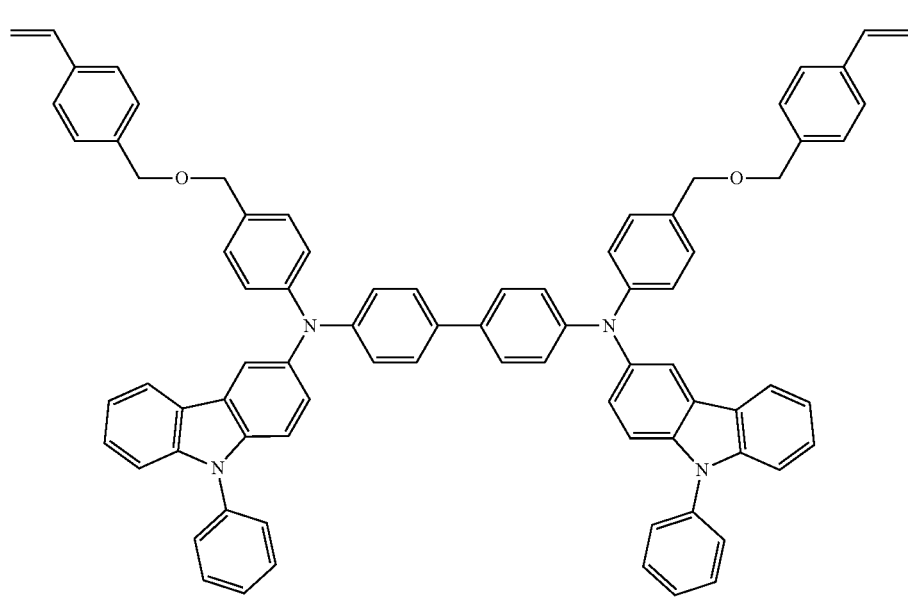
Chemical Formula 1-29
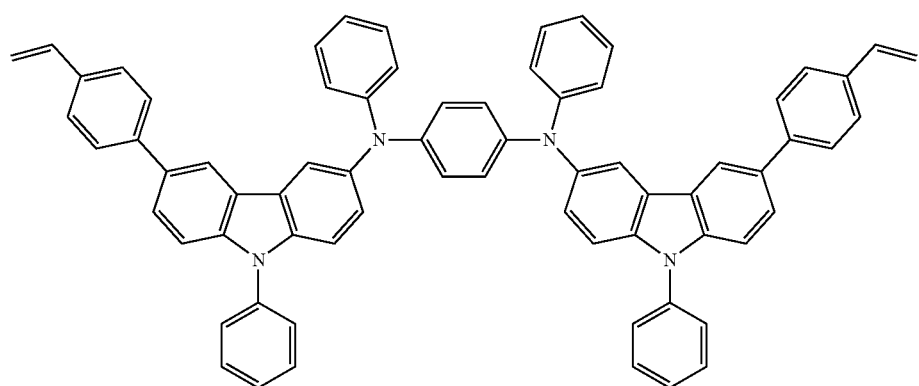

Chemical Formula 1-30

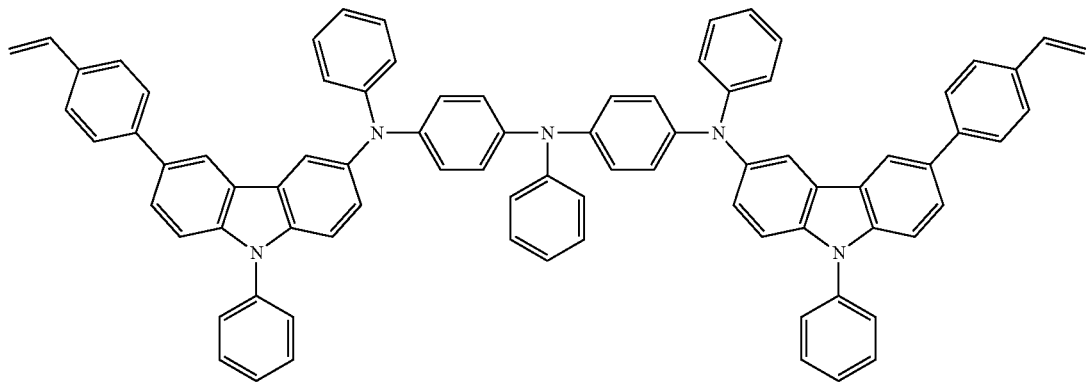

Chemical Formula 1-31

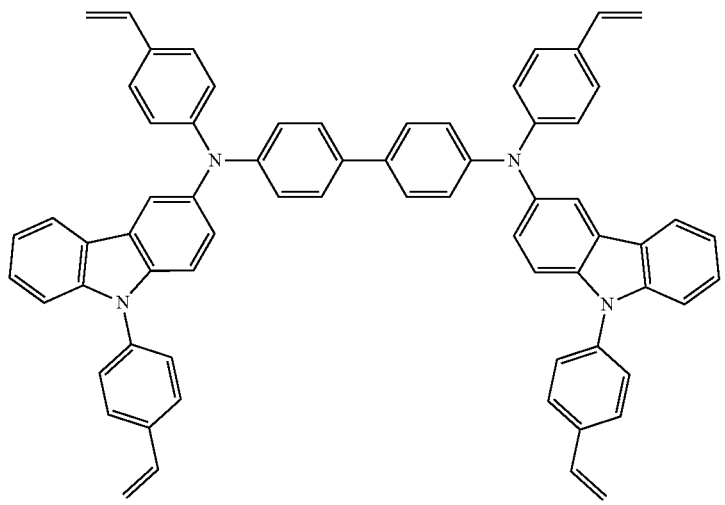

Chemical Formula 1-32

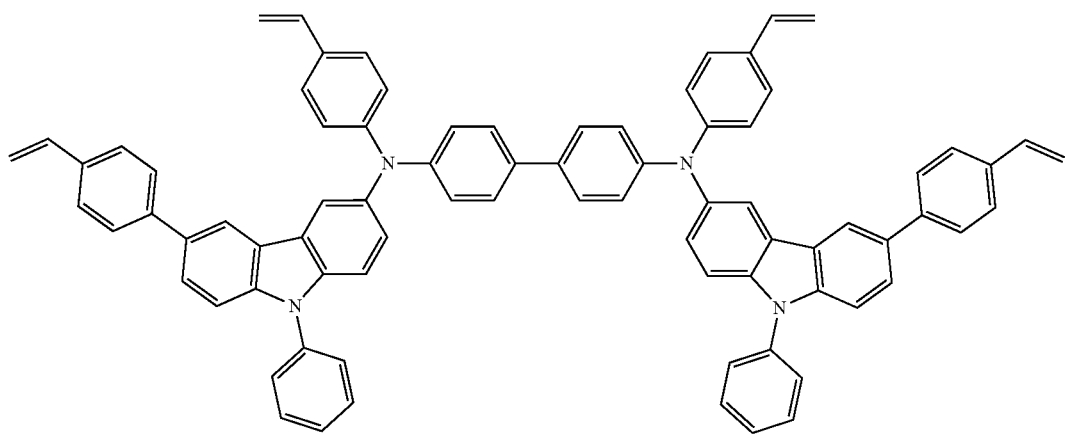

Another embodiment of the present specification provides a coating composition comprising the carbazole derivative described above.

In one embodiment of the present specification, the coating composition comprises the carbazole derivative and a solvent.

In one embodiment of the present specification, the coating composition may further comprise one or two types of compounds selected from the group consisting of a compound introducing a functional group capable of crosslinking in the molecule and a polymer compound.

In one embodiment of the present specification, the coating composition may further comprise a compound introducing a functional group capable of crosslinking in the molecule. When the coating composition further comprises the compound introducing a functional group capable of crosslinking in the molecule, the degree of curing of the coating composition may further increase.

According to one embodiment of the present specification, the compound introducing a functional group capable of crosslinking in the molecule has a molecular weight of 100 g/mol to 3,000 g/mol. In another embodiment of the present specification, the compound introducing a functional group capable of crosslinking in the molecule more preferably has a molecular weight of 500 g/mol to 2,000 g/mol.

In one embodiment of the present specification, the coating composition may further comprise a polymer compound. When the coating composition further comprises the polymer compound, ink properties of the coating composition may increase. In other words, the coating composition further including the polymer compound may provide viscosity suited for coating or inkjet.

In one embodiment of the present specification, the coating composition has viscosity of 2 cP to 15 cP. When having viscosity in the above-mentioned range, a device is readily manufactured.

In one embodiment of the present specification, the polymer compound has a molecular weight of 10,000 g/mol to 200,000 g/mol.

In one embodiment of the present specification, the polymer compound may further include a functional group capable of crosslinking.

In one embodiment of the present specification, the coating composition may be in a liquid state. The "liquid state" means being in a liquid state at room temperature and atmospheric pressure.

In one embodiment of the present specification, examples of the solvent may include ether-based solvents such as tetrahydrofuran and dioxane; aromatic hydrocarbon-based solvents such as toluene, xylene, trimethylbenzene and mesitylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone, cyclohexanone, isophorone, tetralone, decalone and acetylacetone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol; sulfoxide-based solvents such as dimethyl sulfoxide; amide-based solvents such as N-methyl-2-pyrrolidone and N,N-dimethylformamide; tetraline, and the like, however, the solvent is not particularly limited as long as the solvent is capable of dissolving or dispersing the carbazole derivative according to one embodiment of the present disclosure.

In another embodiment, the solvent may be used either alone as one type, or as a mixture of two or more types.

In one embodiment of the present specification, the coating composition may further include one, two or more types of additives selected from the group consisting of a thermal polymerization initiator and a photopolymerization initiator.

In one embodiment of the present specification, the coating composition does not further include a p-doping material.

In another embodiment, the coating composition further includes a p-doping material.

The p-doping material in the present specification may facilitate thermal curing or photocuring.

The p-doping material in the present specification means a material letting a host material have a p-semiconductor property. The p-semiconductor property means a property receiving or transferring holes at a highest occupied molecular orbital (HOMO) energy level, that is, a property of a material having high hole conductivity.

In one embodiment of the present specification, the p-doping material may be represented by any one of the following Chemical Formulae 2 to 5.

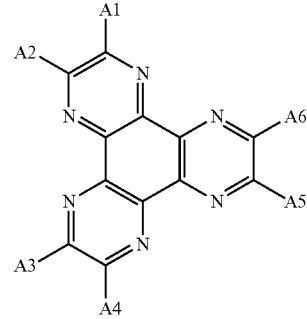

[Chemical Formula 2]

In Chemical Formula 2,

A1 to A6 are the same as or different from each other, and each independently hydrogen; a nitrile group; a nitro group; an amide group; a carbonyl group; a substituted or unsubstituted sulfonyl group; a substituted or unsubstituted ester group; a substituted or unsubstituted alkyl group; a substituted or unsubstituted alkenyl group; a substituted or unsubstituted aryl group; or a substituted or unsubstituted heteroring, or bond to adjacent groups to form a substituted or unsubstituted hydrocarbon ring or a substituted or unsubstituted heteroring,

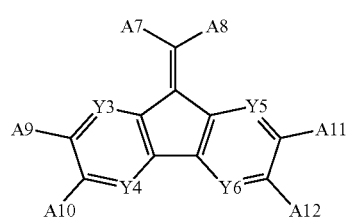

[Chemical Formula 3]

in Chemical Formula 3,

Y3 to Y6 are the same as or different from each other, and each independently CR or N, A7 and A8 are the same as or different from each other, and each independently hydrogen; a nitrile group; —CF$_3$; or —COOA13, R and A9 to A13 are the same as or different from each other, and each independently hydrogen; a halogen group; a nitrile group; a substituted or unsubstituted alkyl group; an unsubstituted alkyl group; a substituted or unsubstituted aryl group; a substituted or unsubstituted heterocyclic group, or bond to adjacent groups to form a substituted or unsubstituted hydrocarbon ring or a substituted or unsubstituted heteroring,

[Chemical Formula 4]

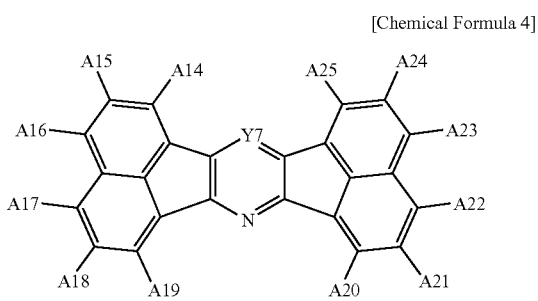

in Chemical Formula 4,

Y7 is the same as or different from each other, and each independently CR' or N, R' and A14 to A25 are the same as or different from each other, and each independently hydrogen; a halogen group; a nitrile group; a substituted or unsubstituted alkyl group; a substituted or unsubstituted alkoxy group; a substituted or unsubstituted aryl group; a substituted or unsubstituted silyl group; or a substituted or unsubstituted heterocyclic group, or bond to adjacent substituents to form a substituted or unsubstituted hydrocarbon ring or a substituted or unsubstituted heteroring,

[Chemical Formula 5]

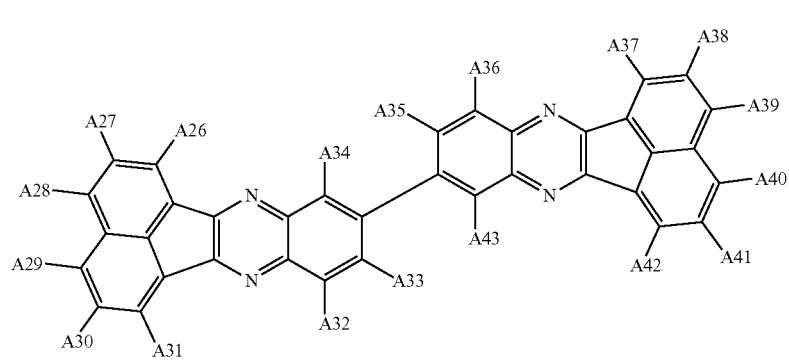

in Chemical Formula 5,

A26 to A43 are the same as or different from each other, and each independently hydrogen; a substituted or unsubstituted alkyl group; a substituted or unsubstituted alkoxy group; a substituted or unsubstituted aryl group; a substituted or unsubstituted silyl group; a substituted or unsubstituted heterocyclic group, or bond to adjacent substituents to form a substituted or unsubstituted hydrocarbon ring or a substituted or unsubstituted heteroring.

In one embodiment of the present specification, A1 to A6 are the same as or different from each other, and each independently a nitrile group; a nitro group; a substituted or unsubstituted sulfonyl group (SO2Ra); a substituted or unsubstituted alkenyl group; or a substituted or unsubstituted aryl group.

Ra means a substituted or unsubstituted aryl group.

In another embodiment, A1 to A6 are each an alkenyl group substituted with a nitrile group.

In another embodiment of the present specification, A1 to A6 are each a nitro group; or an aryl group substituted with a nitrile group.

In another embodiment, A1 to A6 are each a nitro group; or a phenyl group substituted with a nitrile group.

In one embodiment of the present specification, the compound represented by Chemical Formula 2 may be represented by any one of the following Chemical Formulae 2-1 to 2-6.

Chemical Formula 2-1

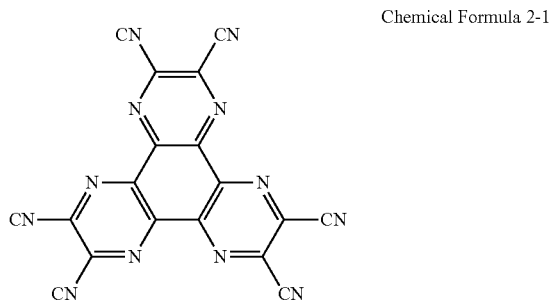

-continued

Chemical Formula 2-2

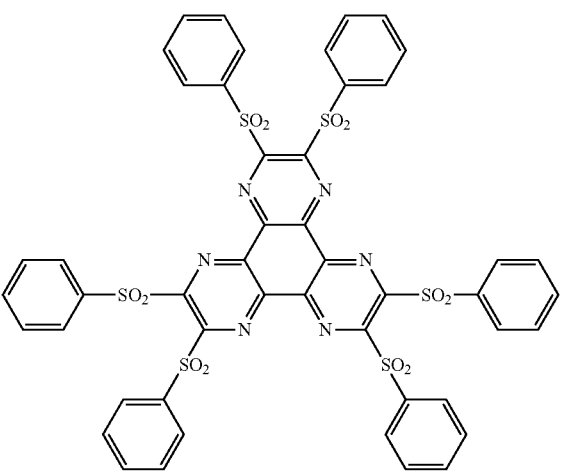

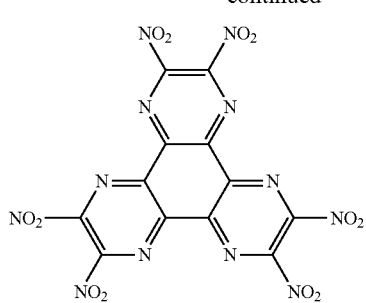
[Chemical Formula 2-3]

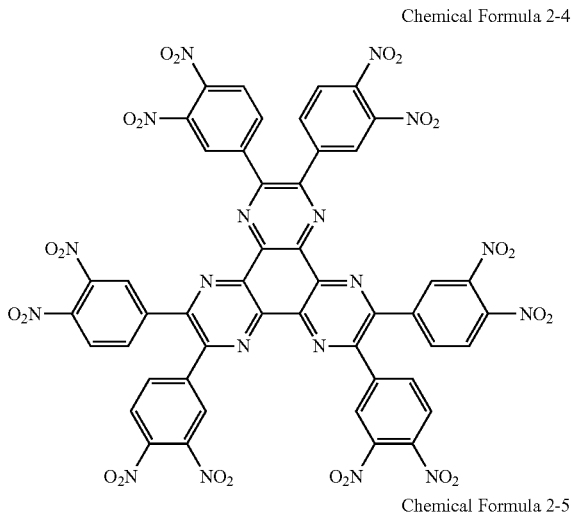
[Chemical Formula 2-4]

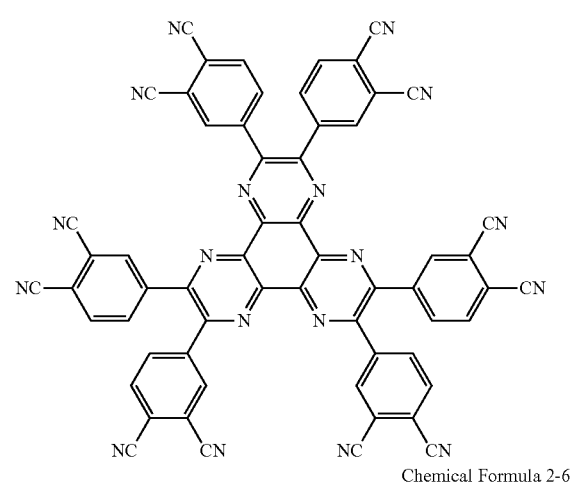
[Chemical Formula 2-5]

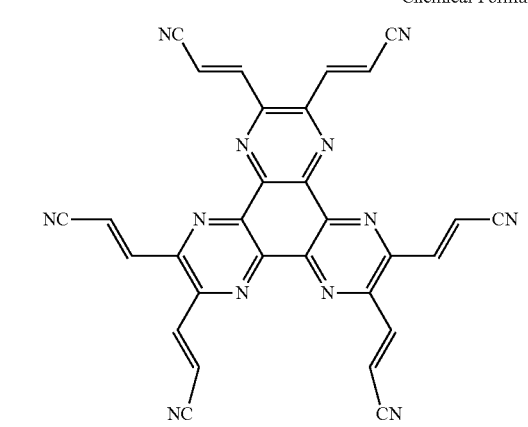
[Chemical Formula 2-6]

In one embodiment of the present specification, A14 and A15 bond to each other to form a substituted or unsubstituted hydrocarbon ring.

In one embodiment of the present specification, A14 and A15 bond to each other to form a benzene ring.

In one embodiment of the present specification, A18 and A19 bond to each other to form a substituted or unsubstituted hydrocarbon ring.

In one embodiment of the present specification, A18 and A19 bond to each other to form a benzene ring.

In one embodiment of the present specification, A20 and A21 bond to each other to form a substituted or unsubstituted hydrocarbon ring.

In one embodiment of the present specification, A20 and A21 bond to each other to form a benzene ring.

In one embodiment of the present specification, Y7 is N.

In one embodiment of the present specification, the compound represented by Chemical Formula 4 may be represented by the following Chemical Formulae 4-1 to 4-3.

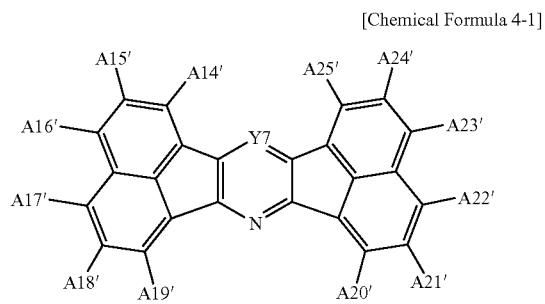
[Chemical Formula 4-1]

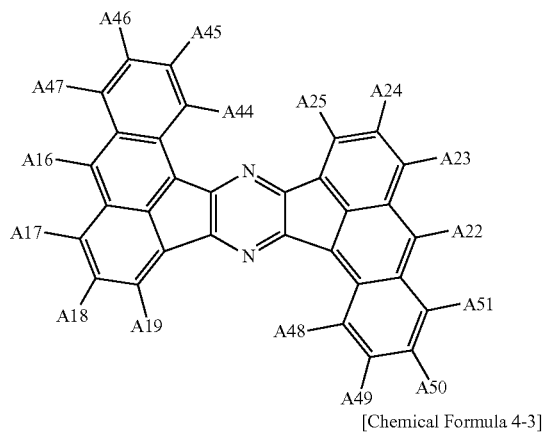
[Chemical Formula 4-2]

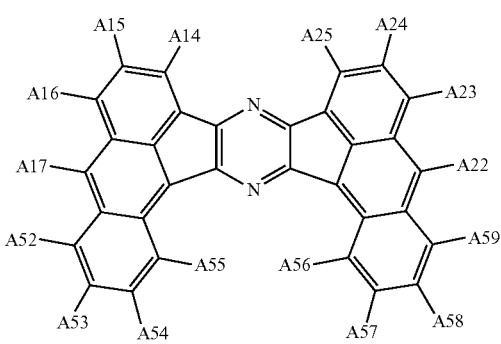
[Chemical Formula 4-3]

In Chemical Formulae 4-1 to 4-3,

Y7 is the same as or different from each other, and each independently CR' or N, R', A14 to A19, and A22 to A25 have the same definitions as in Chemical Formula 4, A44 to A59 are the same as or different from each other, and each independently have the same definitions as A14 to A25, A14' to A25' are the same as or different from each other, and each independently hydrogen; a halogen group; a nitrile group; a substituted or unsubstituted alkyl group; a substituted or unsubstituted alkoxy group; a substituted or unsubstituted aryl group; a substituted or unsubstituted silyl group; or a substituted or unsubstituted heterocyclic group.

In one embodiment of the present specification, the p-doping material may be represented by a conductivity dopant of the following structures, however, the structure is not limited thereto. Including the conductivity dopant may mean a dopant increasing conductivity of an organic material layer formed using the carbazole derivative.

In one embodiment of the present specification, the conductivity dopant may be represented by any one of the following Chemical Formulae 7-1 to 7-11.

[Chemical Formula 7-1]

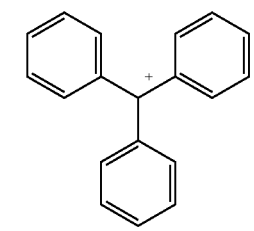 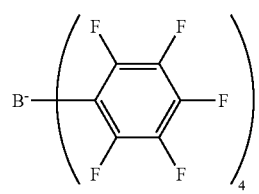

[Chemical Formula 7-2]

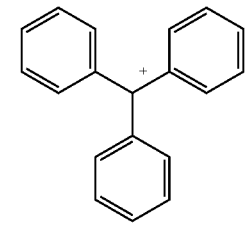 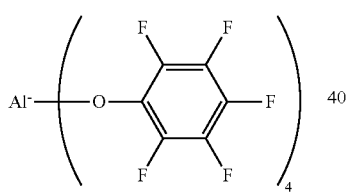

[Chemical Formula 7-3]

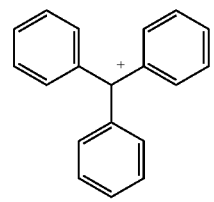 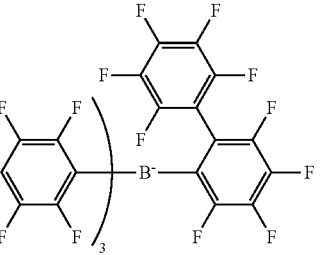

[Chemical Formula 7-4]

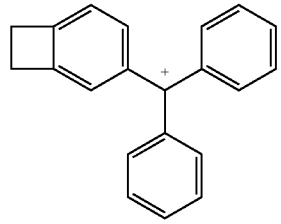 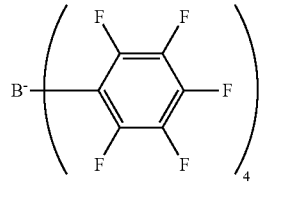

-continued

[Chemical Formula 7-5]

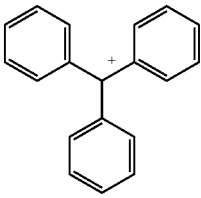 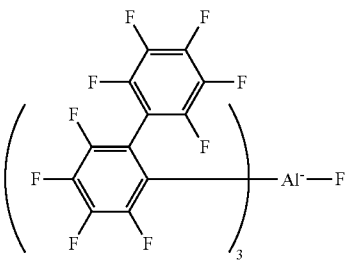

[Chemical Formula 7-6]

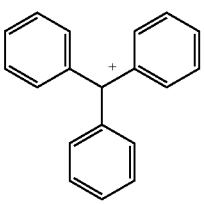 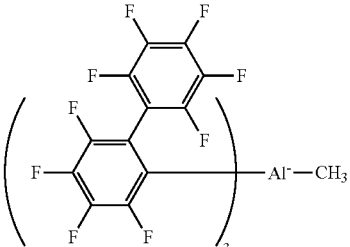

[Chemical Formula 7-7]

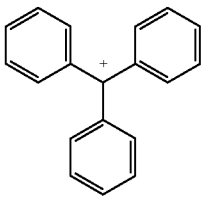 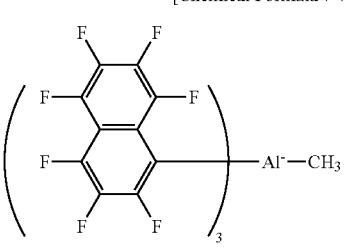

[Chemical Formula 7-8]

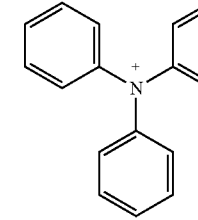 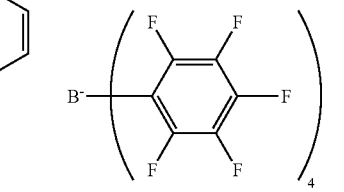

[Chemical Formula 7-9]

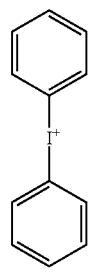 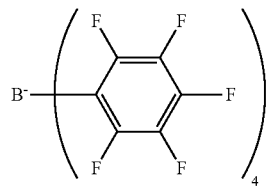

[Chemical Formula 7-10]

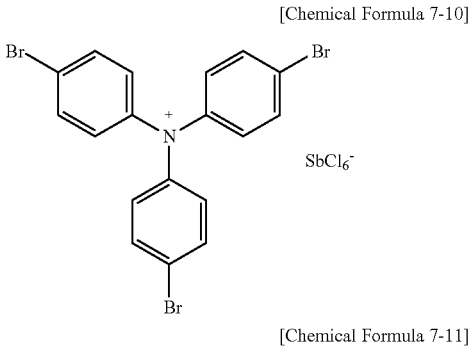

[Chemical Formula 7-11]

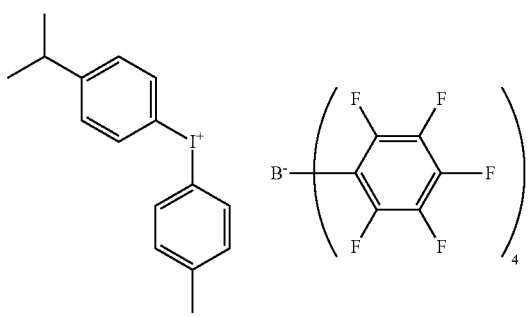

In another embodiment, the p-doping material may be a metal oxide such as $MoO_2(acac)_2$, $VO(acac)_2$, $V(acac)_3$ or $WO_3$, but is not limited thereto.

In another embodiment, the p-doping material may be a halide such as $AgBF_4$, $InCl_3$, $FeCl_3$, $GaCl_3$, $SbCl_5$, $AlCl_3$, $BF_3$, $I_2$ or $Na_2IrCl_6$, but is not limited thereto.

In another embodiment, the p-doping material may include compounds including a sulfonic acid compound or a boron anion as an ionic compound.

In another embodiment, the p-doping material may be a compound including a cyano group, for example, any one of compounds of the following structures, but is not limited thereto.

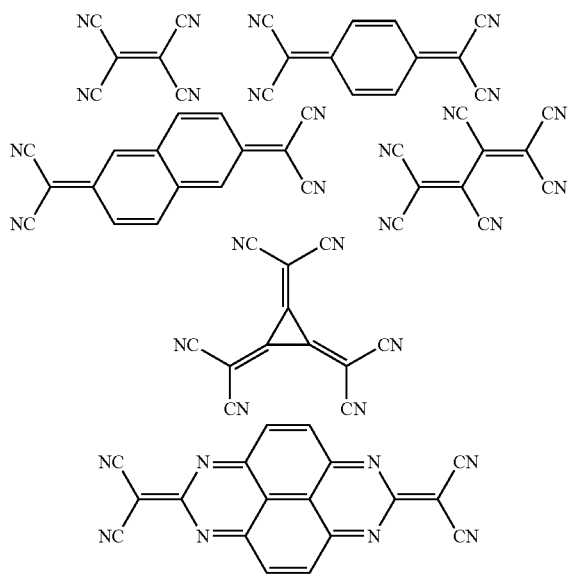

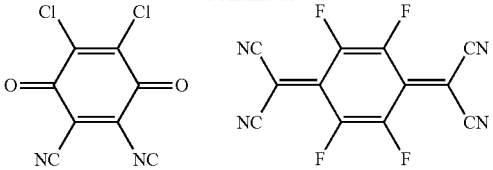

In another embodiment, polymer materials of polystyrene sulfonate (PSS) may be used as the p-doping material, however, the material is not limited thereto.

In another embodiment, the p-doping material may be $Ce(NH_4)_2(NO_3)_6$ or $[FeCp_2]PF_6$, but is not limited thereto.

In the present specification, the p-doping material is not limited as long as it is a material having p-semiconductor properties, and one, two or more types thereof may be used without limiting types thereof.

In one embodiment of the present specification, content of the p-doping material may be from 0% by weight to 50% by weight based on the whole carbazole derivative.

In one embodiment of the present specification, content of the p-doping material is from 0% by weight to 30% by weight based on the total solid content of the coating composition.

In one embodiment of the present specification, content of the p-doping material is preferably from 1% by weight to 30% by weight based on the total solid content of the coating composition, and in another embodiment, content of the p-doping material is more preferably from 1% by weight to 10% by weight based on the total solid content of the coating composition.

In another embodiment, the coating composition may further include a monomer including a functional group capable of crosslinking; or a monomer including a terminal group capable of forming a polymer by heat. A molecular weight of the monomer including a functional group capable of crosslinking; or the monomer including a terminal group capable of forming a polymer by heat may be 2,000 g/mol or less.

As in one embodiment of the present specification, the curing temperature may be lowered when the coating composition further includes a monomer including a functional group capable of crosslinking; or a monomer including a terminal group capable of forming a polymer by heat, and the coating composition may be more preferably formed with similar structures that do not affect physical properties of the carbazole derivative of the present specification.

In one embodiment of the present specification, the coating composition has a molecular weight of 2,000 g/mol or less, and further includes a monomer including a functional group capable of crosslinking; or a monomer including a terminal group capable of forming a polymer by heat.

The monomer including a functional group capable of crosslinking; or the monomer including a terminal group capable of forming a polymer by heat may mean a monomer in which aryl of phenyl, biphenyl, fluorine or naphthalene; arylamine; or carbazole is substituted with a functional group capable of crosslinking or a terminal group capable of forming a polymer by heat.

The functional group capable of crosslinking is the same as described above.

In addition, in one embodiment of the present specification, the monomer including a functional group capable of crosslinking includes the following structures, however, the monomer is not limited as long as it does not harm properties of the coating composition.

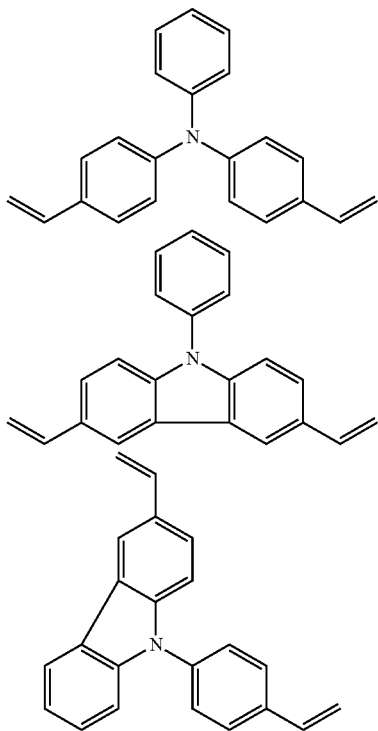

In another embodiment, the monomer including a terminal group capable of forming a polymer by heat includes the following structures, however, the monomer is not limited as long as it does not harm properties of the coating composition.

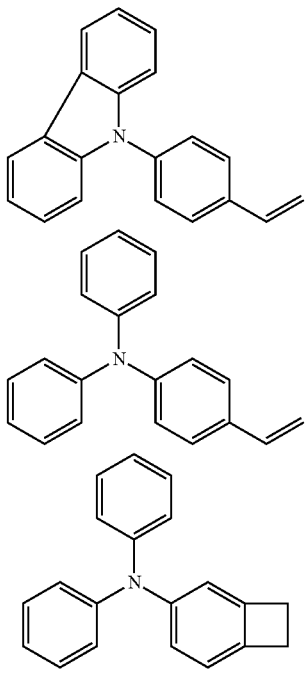

One embodiment of the present specification also provides an organic light emitting device formed using the coating composition.

In one embodiment of the present specification, the organic light emitting device comprises a cathode; an anode; and one or more organic material layers provided between the cathode and the anode, and one or more layers of the organic material layers are formed using the coating composition.

In one embodiment of the present specification, the organic material layer formed using the coating composition is a hole transfer layer, a hole injection layer or a layer carrying out hole transfer and hole injection at the same time.

In another embodiment, the organic material layer formed using the coating composition is a light emitting layer.

In another embodiment, the organic material layer formed using the coating composition is a light emitting layer, and the light emitting layer comprises the carbazole derivative as a host of the light emitting layer.

In one embodiment of the present specification, the organic light emitting device further comprises one, two or more layers selected from the group consisting of a hole injection layer, a hole transfer layer, an electron transfer layer, an electron injection layer, an electron blocking layer and a hole blocking layer.

In another embodiment, the organic light emitting device may be an organic light emitting device having a structure consecutively laminating an anode, one or more organic material layers and a cathode on a substrate (normal type).

In another embodiment, the organic light emitting device may be an organic light emitting device having an inverted structure consecutively laminating a cathode, one or more organic material layers and an anode on a substrate (inverted type).

The organic material layer of the organic light emitting device of the present specification may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may include less numbers of organic material layers.

Figure 1:
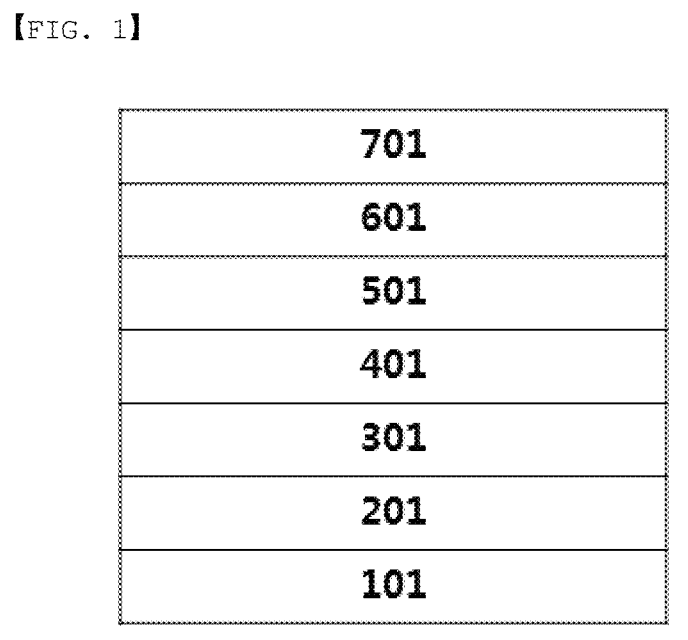

For example, a structure of an organic light emitting device according to one embodiment of the present specification is illustrated in FIG. 1.

FIG. 1 illustrates a structure of an organic light emitting device in which an anode (201), a hole injection layer (301), a hole transfer layer (401), a light emitting layer (501), an electron transfer layer (601) and a cathode (701) are consecutively laminated on a substrate (101).

In FIG. 1, the hole injection layer (301), the hole transfer layer (401) and the light emitting layer (501) are formed using the coating composition including the carbazole derivative.

FIG. 1 is a diagram illustrating the organic light emitting device, and the organic light emitting device is not limited thereto.

When the organic light emitting device comprises a plurality of organic material layers, the organic material layers may be formed with materials that are the same as or different from each other.

The organic light emitting device of the present specification may be manufactured using materials and methods known in the art, except that one or more layers of the organic material layers are formed using the coating composition including the carbazole derivative.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

One embodiment of the present specification also provides a method for manufacturing an organic light emitting device formed using the coating composition.

Specifically, in one embodiment of the present specification, the method comprises preparing a substrate; forming a cathode or an anode on the substrate; forming one or more organic material layers on the cathode or the anode; and forming an anode or a cathode on the organic material layers, wherein one or more layers of the organic material layers are formed using the coating composition.

In one embodiment of the present specification, the organic material layer formed using the coating composition is formed using spin coating.

In another embodiment, the organic material layer formed using the coating composition is formed using a printing method.

In an embodiment of the present specification, examples of the printing method comprise inkjet printing, nozzle printing, offset printing, transfer printing, screen printing or the like, but are not limited thereto.

In another embodiment, the organic material layer formed using the coating composition is formed using an inkjet method.

The coating composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer formed using the coating composition includes coating the coating composition on the cathode or the anode; and heat treating or light treating the coated coating composition.

In one embodiment of the present specification, a heat treatment temperature in the heat treatment step is 230° C. or lower, and more preferably from 85° C. to 230° C.

In another embodiment, a heat treatment time in the heat treatment step may be for 1 minute to 1 hour.

In one embodiment of the present specification, when the coating composition does not include additives, crosslinking is preferably progressed through heat treatment at a temperature of 85° C. to 230° C., and crosslinking is more preferably progressed at a temperature of 85° C. to 200° C. In addition, the coating composition of the present specification may further include an initiator, but it is more preferable not to use an initiator.

When the heat treatment or the light treatment step is included in the forming of an organic material layer formed using the coating composition, an organic material layer including a thin-filmed structure by a plurality of the carbazole derivatives included in the coating composition forming crosslinkage may be provided. In this case, when another layer is laminated on the surface of the organic material layer formed using the coating composition, dissolution caused by a solvent, or morphological influences or decomposition may be prevented.

Accordingly, when an organic material layer formed using the coating composition is formed including the heat treatment or the light treatment step, resistance for a solvent increases, and multiple layers may be formed by repeatedly carrying out solution deposition and crosslinking methods, and as a result, lifespan properties of a device may be enhanced by increasing stability.

In one embodiment of the present specification, the coating composition including the carbazole derivative may use a coating composition mixed and dispersed to a polymer bonding agent.

As the polymer bonding agent in one embodiment of the present specification, those that do not extremely inhibit charge transfer are preferred, and those that do not exhibit strong absorption for visible light are preferably used. Examples of the polymer bonding agent include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

By the carbazole derivative according to one embodiment of the present specification including carbazole and an amine group, the carbazole derivative may be included alone in the organic material layer, or the coating composition including the carbazole derivative may be progressed to a thin film through heat treatment or light treatment, or may be included as a copolymer using a coating composition mixed with other monomers. In addition, the coating composition may be included as a copolymer or included as a mixture by using a coating composition mixed with other polymers.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzo quinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato) (0-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

In one embodiment of the present specification, the hetero-cyclic compound may be included in organic solar cells or organic transistors in addition to organic light emitting devices.

Hereinafter, the present specification will be described in detail with reference to examples. However, the examples according to the present specification may be modified to various other forms, and the scope of the present specification is not to be construed as being limited to the examples described below. Examples of the present specification are provided in order to more completely describe the present specification to those having average knowledge in the art.

Preparation Example 1. Preparation of Chemical Formula 1-1
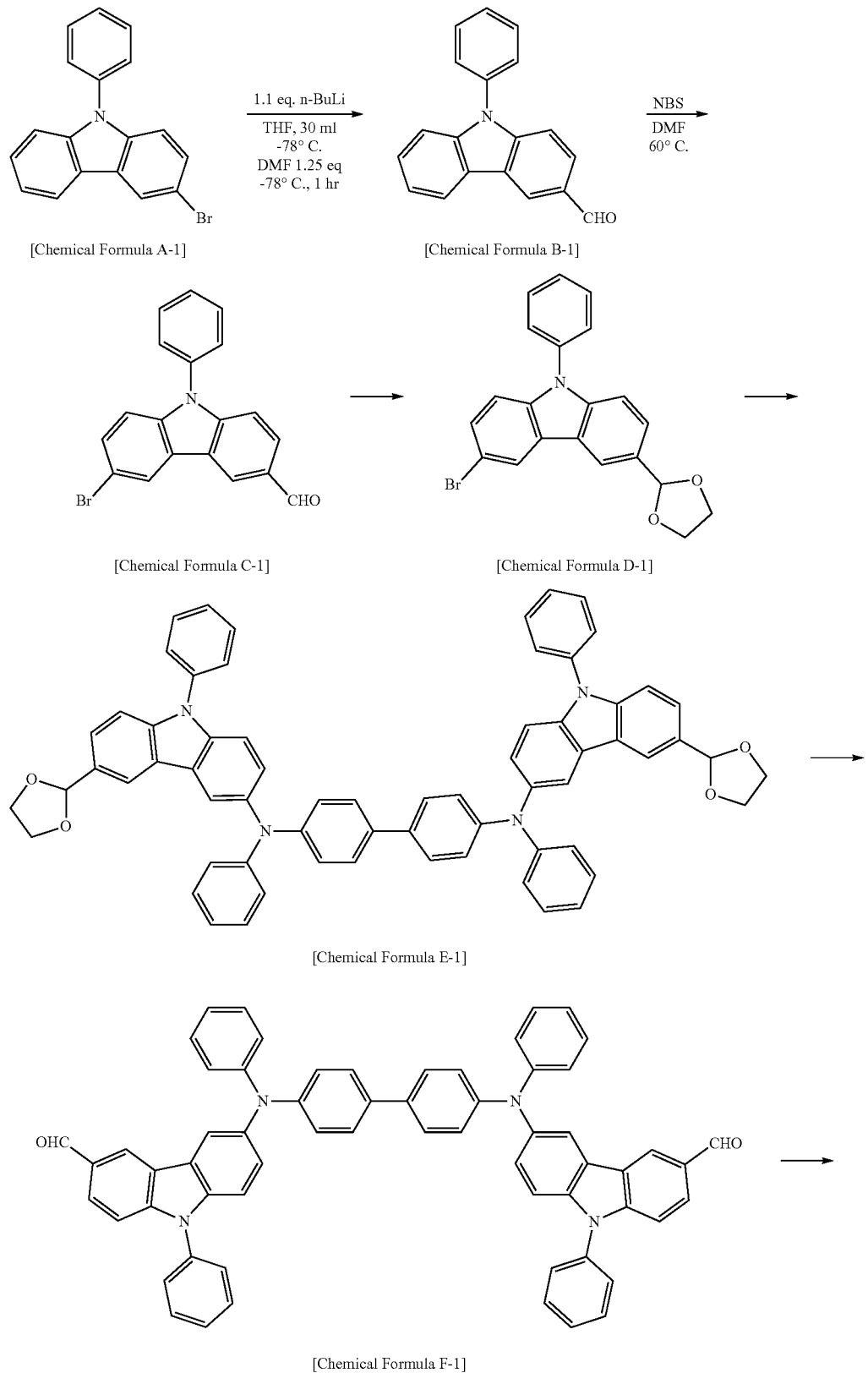
[Chemical Formula A-1] [Chemical Formula B-1]
[Chemical Formula C-1] [Chemical Formula D-1]
[Chemical Formula E-1]
[Chemical Formula F-1]

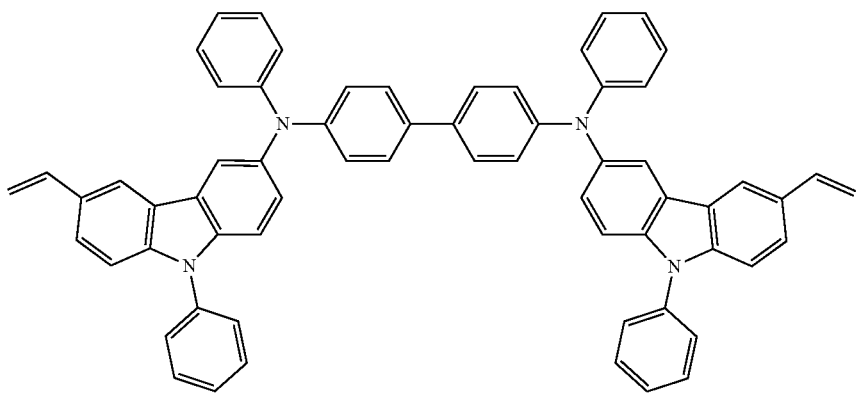

[Chemical Formula 1-1]

(1) Preparation of Chemical Formula A-1

N-phenyl carbazole (27 g, 111 mmol) was dissolved in chloroform (200 mL), N-bromosuccinimide (19.7 g, 111 mmol) was added thereto, and the result was stirred for 5 hours at room temperature.

Distilled water was introduced to the reaction solution to terminate the reaction, and the organic layer was extracted. The reaction solution was concentrated and used in the next reaction without a purification process. MS:[M+H]$^+$=321

(2) Preparation of Chemical Formula B-1

After dissolving Chemical Formula A-1 (10.3 g, 32 mmol) prepared in the step (1) in 50 mL of tetrahydrofuran (THF), 1.1 eq. of n-butyllithium (n-BuLi) (2.5 M in HEX, 14.1 mL, 35.2 mmol) was introduced thereto at −78° C. and stirred, and 10 mL of anhydrous dimethylformamide (DMF) was added dropwise thereto. The result was stirred for 1 hour at the same temperature, then distilled water was introduced to the reaction solution to terminate the reaction, and the organic layer was extracted. The reaction solution was concentrated and recrystallized with ethyl alcohol (EtOH) to obtain Chemical Formula B-1 (9.5 g, yield 84%). MS: [M+H]$^+$=272

(3) Preparation of Chemical Formula C-1

After dissolving Chemical Formula B-1 (4 g, 11.3 mmol) prepared in the step (2) and N-bromosuccinimide (NBS 2.74 g, 11.3 mmol) in 50 ml of dimethylformamide (DMF), the result was stirred for 6 hours at 60° C. Distilled water was introduced to the reaction solution to terminate the reaction and to form precipitates, and the formed precipitates were filtered and sufficiently washed with water. The result was vacuum dried to obtain Chemical Formula C-1 (3.1 g, yield 78%). MS: [M+H]$^+$=349

(4) Preparation of Chemical Formula D-1

After dissolving Chemical Formula C-1 (3.1 g, 8.85 mmol) prepared in the step (3) and dihydroxyethane (1.1 g, 17.7 mmol) in 50 ml of toluene, the result was stirred for 48 hours at 150° C. Ethanol was added to the reaction solution to form precipitates. The formed ivory solids were filtered, washed with ethanol, and then vacuum dried to obtain Chemical Formula D-1 (2.8 g, yield 80.2%). MS: [M+H]$^+$=393

(5) Preparation of Chemical Formula E-1

After dissolving Chemical Formula D-1 (3.1 g, 8.85 mmol) prepared in the step (4) and N4,N4'-diphenyl-[1,1'-biphenyl]-4,4'-diamine (1.24 g, 6.32 mmol) in 100 ml of xylene, sodium-tertiary-butoxide (1.2 g, 12.64 mmol), 0.13 g (0.23 mmol) of bisdibenzylideneacetone palladium(0) and 0.11 ml (0.23 mmol) of a 50 wt % tri-tertiary-butylphosphine toluene solution were added thereto, and the result was refluxed for 5 hours under nitrogen atmosphere.

Distilled water was introduced to the reaction solution to terminate the reaction, and the organic layer was extracted. The result was column separated using a normal-hexane/tetrahydrofuran=6/1 solvent, stirred in ethyl alcohol (EtOH), filtered and then vacuum dried to obtain Chemical Formula E-1 (2.92 g, yield 48%). MS: [M+H]$^+$=963

FIG. 2 is a diagram showing an NMR spectrum of Chemical Formula E-1.

(6) Preparation of Chemical Formula F-1

After dissolving Chemical Formula E-1 (2.92 g, 3.03 mmol) prepared in the step (5) in 50 ml of tetrahydrofuran (THF), 20 ml of 1 N hydrochloric acid (HCl) solution was added thereto, and the result was stirred for 1 hour. The organic material layer was extracted, dried with anhydrous magnesium sulfate, and then filtered, and after removing the solvent, the result was recrystallized with ethanol to obtain Chemical Formula F-1 (2.55 g, yield 96%). MS: [M+H]$^+$=875

(7) Preparation of Chemical Formula 1-1

After dissolving (bromomethyl)triphenylphosphonium bromide (3 g, 6.87 mmol) in 100 mL of tetrahydrofuran (THF), 1 eq. of n-butyllithium (n-BuLi) (2.5 M in HEX, 2.8 mL, 6.87 mmol) was introduced thereto at −78° C., and the result was stirred for 20 minutes. After raising the reaction temperature to 0° C., Chemical Formula F-1 (2 g, 2.29 mmol) prepared in the step (6) was introduced to the reactant, and the result was stirred for 1 hour at the same temperature.

Distilled water was introduced to the reaction solution to terminate the reaction, and the organic layer was extracted. The reaction solution was concentrated, dissolved in methylene chloride (MC), and then recrystallized with ethyl alcohol (EtOH) to obtain Chemical Formula 1-1 (1.18 g, yield 59%). MS: [M+H]$^+$=872

FIG. 6 is a diagram showing an MS spectrum of Chemical Formula 1-1.

Preparation Example 2. Preparation of Chemical Formula 1-2
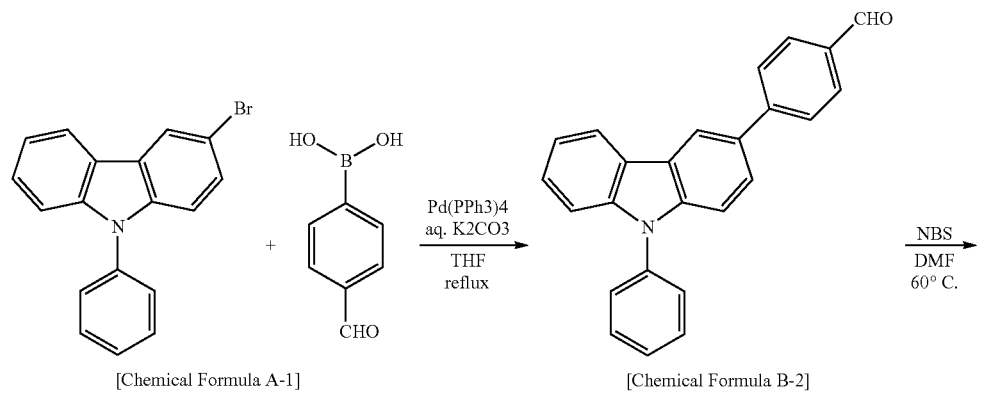
[Chemical Formula A-1]     [Chemical Formula B-2]
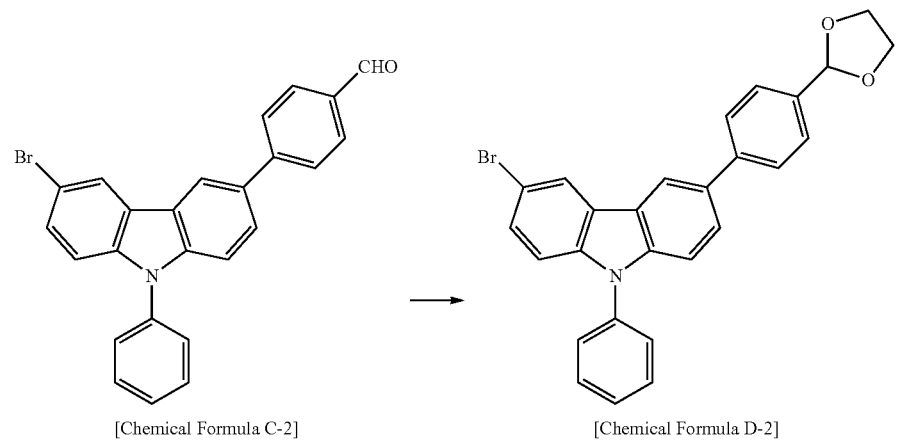
[Chemical Formula C-2]     [Chemical Formula D-2]
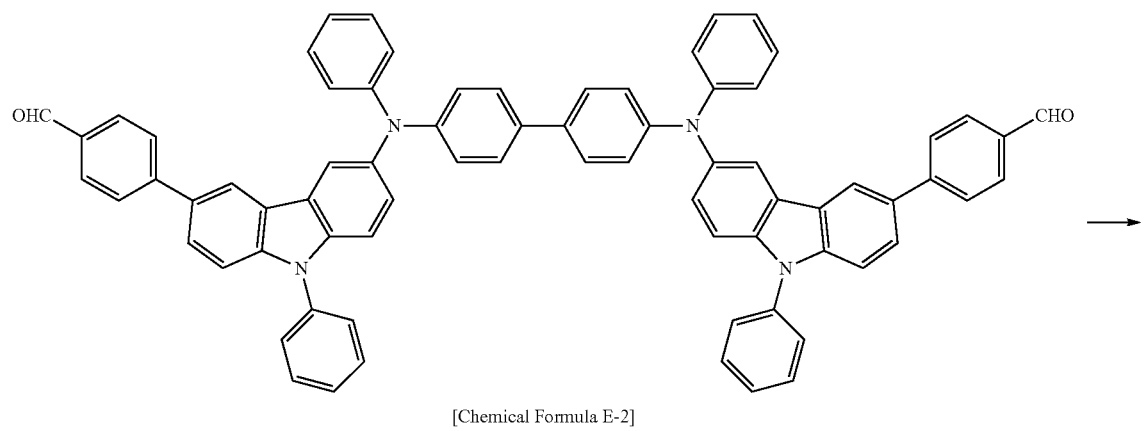
[Chemical Formula E-2]

-continued

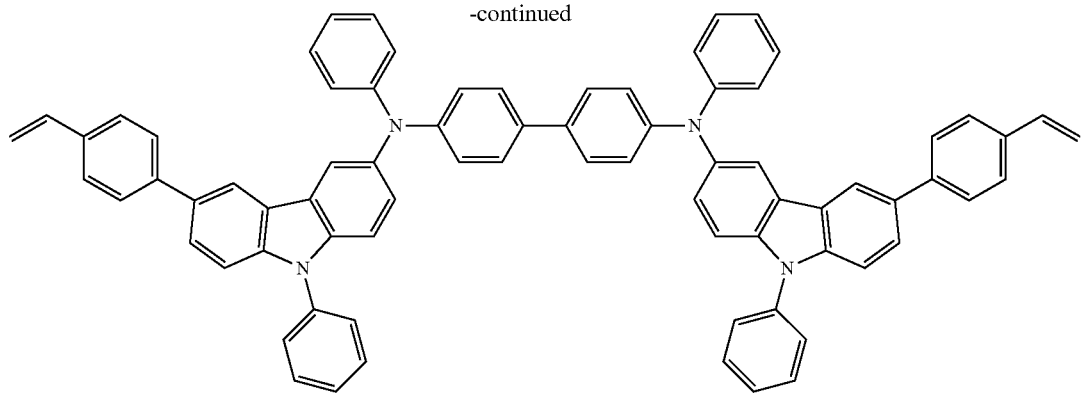

[Chemical Formula 1-2]

(1) Preparation of Chemical Formula B-2

After dissolving Chemical Formula A-1 (9 g, 27.9 mmol) and 4-formylbenzene boronic acid (4.18 g, 27.9 mmol) in anhydrous tetrahydrofuran (THF) (100 mL), Pd(PPh$_3$)$_4$ (0.32 g, 0.28 mmol) and 70 ml of a 2 M aqueous potassium carbonate (K$_2$CO$_3$/H$_2$O) solution were added thereto, and the result was refluxed for 6 hours. After cooling the reaction solution to room temperature, the organic layer was extracted. The reaction solution was concentrated and recrystallized with ethyl alcohol (EtOH) to obtain Chemical Formula B-2 (8.9 g, yield 92%). MS: [M+H]$^+$=348

(2) Preparation of Chemical Formula C-2

After dissolving Chemical Formula B-2 (8.2 g, 23.6 mmol) prepared in the step (1) in chloroform (200 mL), N-bromosuccinimide (4.15 g, 23.6 mmol) was added thereto, and the result was stirred for 5 hours at room temperature. Distilled water was introduced to the reaction solution to terminate the reaction, and the organic layer was extracted. The reaction solution was concentrated and recrystallized with ethyl alcohol (EtOH) to obtain Chemical Formula C-2 (8.25 g, yield 82%). MS: [M+H]$^+$=425

FIG. 3 is a diagram showing an MS spectrum of Chemical Formula C-2.

(3) Preparation of Chemical Formula D-2

After dissolving Chemical Formula C-2 (3.1 g, 8.85 mmol) prepared in the step (2) and dihydroxyethane (1.1 g, 17.7 mmol) in 50 ml of toluene, the result was stirred for 48 hours at 150° C. Ethanol was added to the reaction solution to form precipitates. The formed ivory solids were filtered, washed with ethanol, and vacuum dried to obtain Chemical Formula D-2 (2.8 g, yield 80.2%). MS: [M+H]$^+$=469

(4) Preparation of Chemical Formula E-2

After dissolving Chemical Formula D-2 (3 g, 7.04 mmol) prepared in the step (3) and N4,N4'-diphenyl-[1,1'-biphenyl]-4,4'-diamine (0.99 g, 2.93 mmol) in 40 ml of xylene, sodium-tertiary-butoxide (0.68 g, 7.04 mmol), 0.13 g (0.23 mmol) of bisdibenzylideneacetone palladium(0) and 0.11 ml (0.23 mmol) of a 50 wt % tri-tertiary-butylphosphine toluene solution were added thereto, and the result was refluxed for 5 hours under nitrogen atmosphere.

Distilled water was introduced to the reaction solution to terminate the reaction, and the organic layer was extracted. The result was column separated using a normal-hexane/tetrahydrofuran=6/1 solvent, stirred in ethyl alcohol (EtOH), filtered and then vacuum dried to obtain Chemical Formula E-2 (2.92 g, yield 48%). MS: [M+H]$^+$=1027

(5) Preparation of Chemical Formula 1-2

After dissolving (bromomethyl)triphenylphosphonium bromide (2.55 g, 5.85 mmol) in 100 mL of tetrahydrofuran (THF), 1 eq. of n-butyllithium (n-BuLi) (2.5 M in HEX, 2.34 mL, 5.85 mmol) was introduced thereto at −78° C., and the result was stirred for 20 minutes. After raising the reaction temperature to 0° C., Chemical Formula E-2 (2 g, 1.95 mmol) prepared in the step (4) was introduced to the reactant, and the result was stirred for 1 hour at the same temperature. Distilled water was introduced to the reaction solution to terminate the reaction, and the organic layer was extracted. The reaction solution was concentrated, dissolved in methylene chloride (MC), and then recrystallized with ethyl alcohol (EtOH) to obtain Chemical Formula 1-2 (1.28 g, yield 64%). MS: [M+H]$^+$=1023

FIG. 4 is a diagram showing an MS spectrum of Chemical Formula 1-2.

FIG. 7 is a diagram showing a differential scanning calorimetry of Chemical Formula 1-2.

Preparation Example 3. Preparation of Chemical Formula 1-5

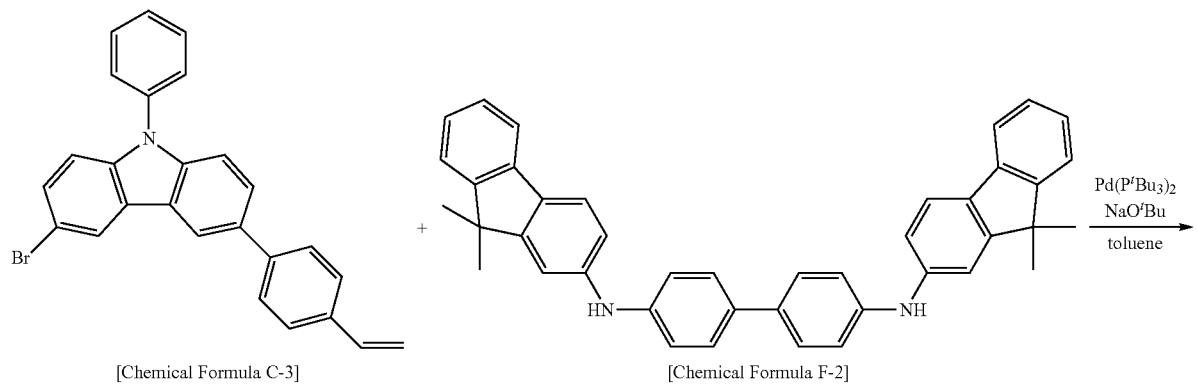

[Chemical Formula C-3]     [Chemical Formula F-2]

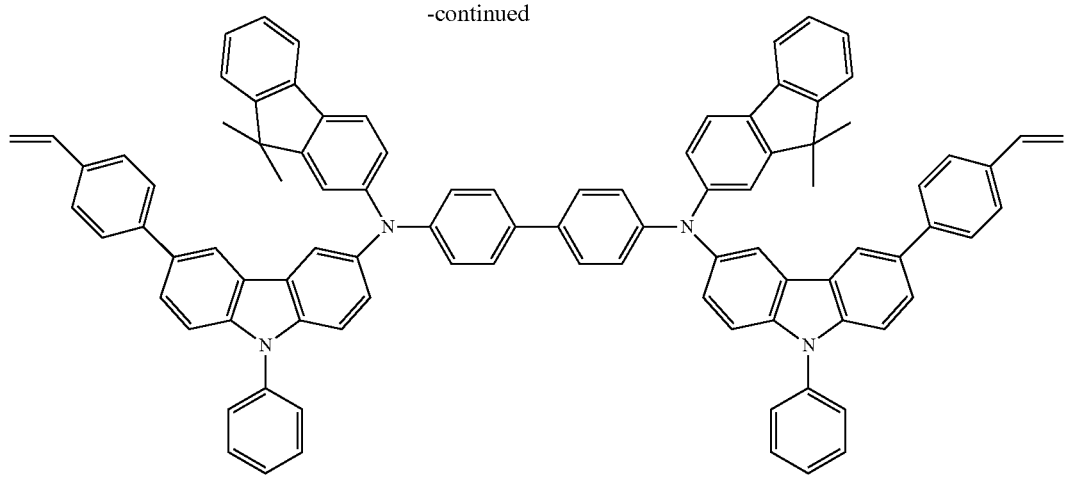

[Chemical Formula 1-5]

After dissolving 3-bromo-9-phenyl-5 6-(4-vinylphenyl)-9H-carbazole (1.77 g, 4.18 mmol) and N,N'-bis(9,9-dimethyl-9H-fluoren-2-yl)-[1,1'-biphenyl]-4,4'-diamine (1.03 g, 1.82 mmol) in 30 ml of toluene, sodium-tertiary-butoxide (3.46 g, 36.07 mmol) and 0.09 g (0.18 mmol) of bis[tri-tert-butylphosphine]palladium(0) were added thereto, and the result was refluxed for 24 hours under nitrogen atmosphere.

Distilled water was introduced to the reaction solution to terminate the reaction, and the organic layer was extracted. The result was column separated using a normal-hexane/methylene chloride=1/1 solvent, stirred in ethyl alcohol (EtOH), filtered and then vacuum dried to obtain Chemical Formula 1-5 (0.83 g, yield 15%). MS: [M+H]$^+$=1254

FIG. 5 is a diagram showing an MS spectrum of Chemical Formula 1-5.

FIG. 8 is a diagram showing a differential scanning calorimetry of Chemical Formula 1-5.

Preparation Example 4. Preparation of Chemical Formula 1-17

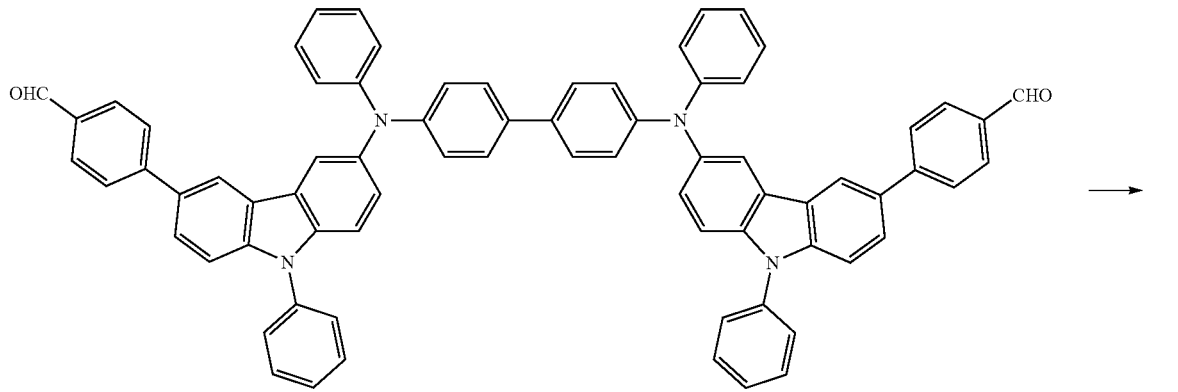

[Chemical Formula E-2]

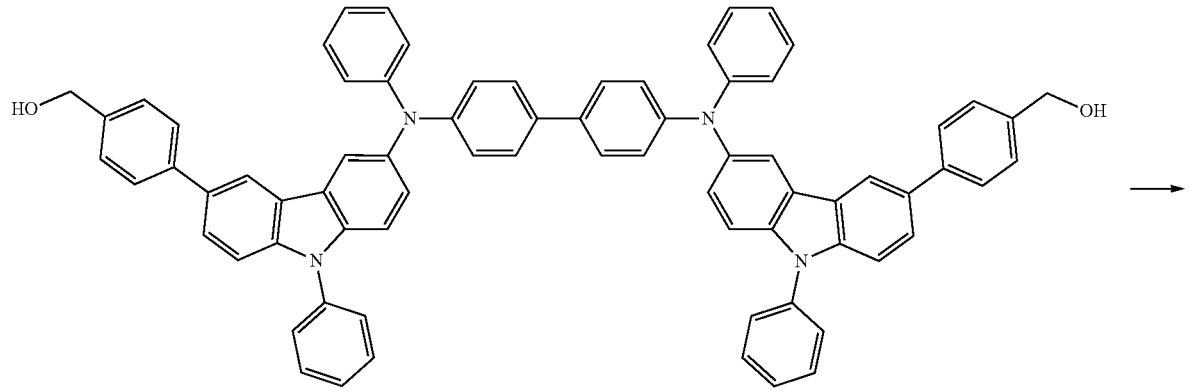

[Chemical Formula F-3]

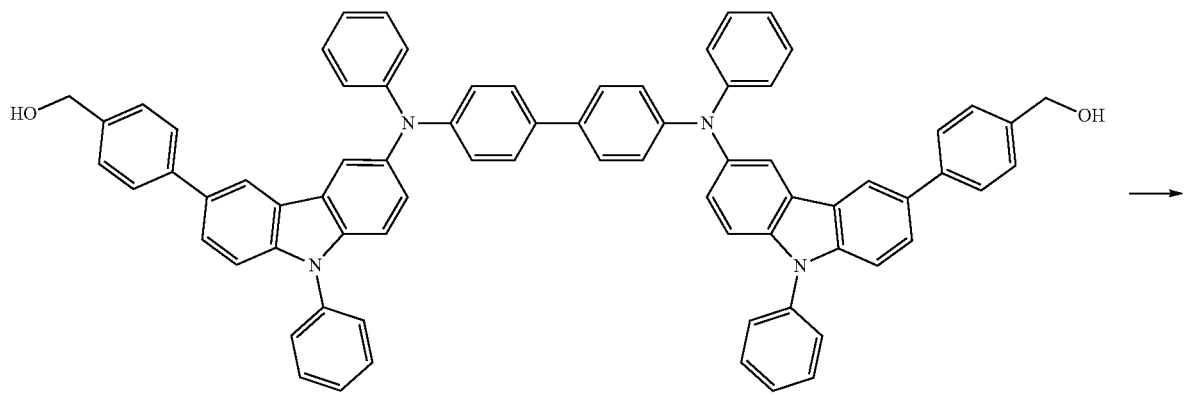

[Chemical Formula F-3]

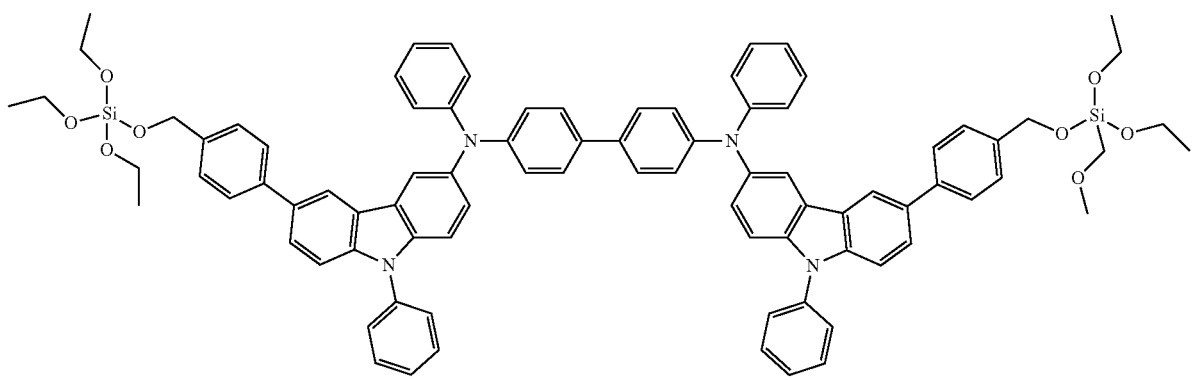

[Chemical Formula 1-17]

(1) Preparation of Chemical Formula F-3

After dissolving the compound of Chemical Formula E-2 (2.05 g, 2 mmol) in 50 mL of tetrahydrofuran (THF) in a 50 mL reaction flask, sodium borohydride (NaBH$_4$) (1.00 g, 26 mmol) and 2 mL of ethanol were injected to the flask. The result was stirred for 30 minutes at room temperature, and then water was added to terminate the reaction. The organic layer was extracted with ethyl acetate, dried with anhydrous magnesium sulfate and concentrated, and then developed using column chromatography (EA:Hex=1:1) to obtain Compound F-3 in a 87% yield.

(2) Preparation of Chemical Formula 1-17

After dissolving the compound of Chemical Formula F-3 (1.79 g, 1.74 mmol) in 50 mL of tetrahydrofuran (THF), triethylamine (0.43 g, 4.2 mmol) was injected thereto, and the result was stirred for 10 minutes at room temperature. Chlorotriethoxysilane (1.02 g, 5.13 mmol) was added dropwise to the reactant, and the result was stirred for 15 hours at room temperature. Water was poured to the reaction mixture, and the result was extracted with ethyl acetate, dried with anhydrous magnesium sulfate, concentrated, and separated using column chromatography (EA:Hex=1:2) to obtain Chemical Formula 1-17 in a 93% yield.

Preparation Example 5. Preparation of Chemical Formula 1-25
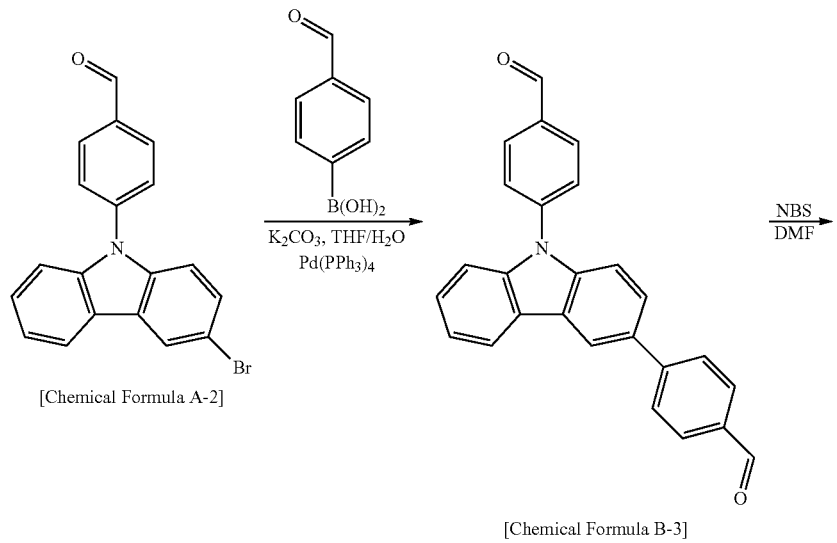
[Chemical Formula A-2]
[Chemical Formula B-3]
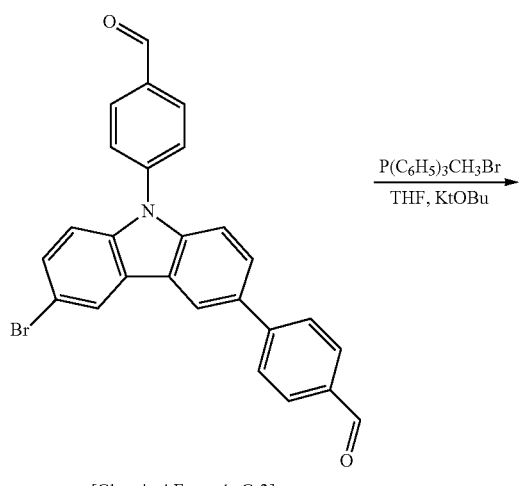
[Chemical Formula C-3]
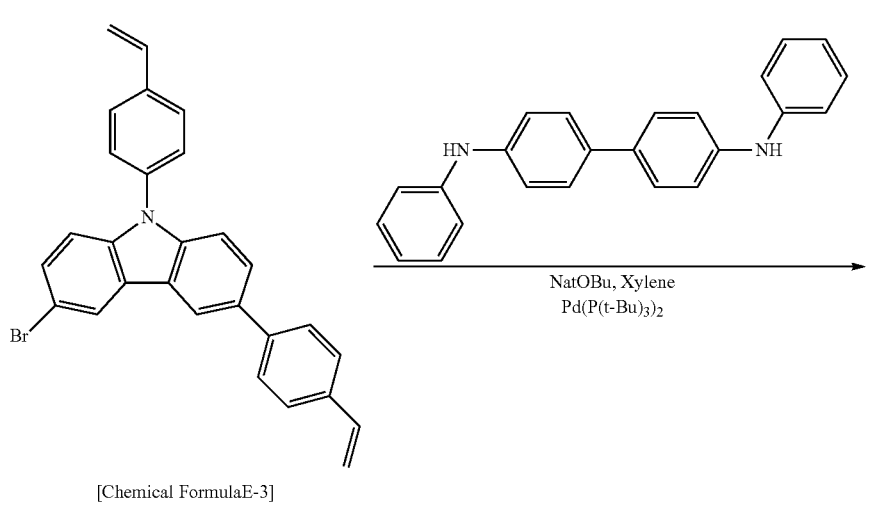
[Chemical FormulaE-3]

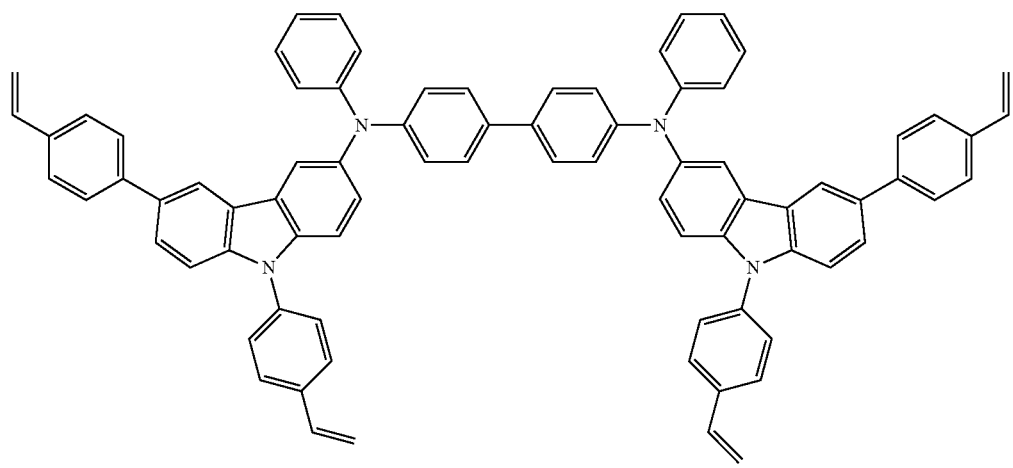

[Chemical Formula 1-25]

(1) Preparation of Chemical Formula B-3

Compound B-3 was obtained in the same manner as Chemical Formula B-2 of Preparation Example 2, except that Chemical Formula A-2 was used instead of Chemical Formula A-1. MS: $[M+H]^+=376$ (2) Preparation of Chemical Formula C-3

Compound C-3 was obtained in the same manner as Chemical Formula C-2 of Preparation Example 2, except that Chemical Formula B-3 was used instead of Chemical Formula B-2. MS: $[M+H]^+=454$ (3) Preparation of Chemical Formula 1-25

Compound 1-25 was obtained in the same manner as Chemical Formula E-2 of Preparation Example 2, except that Chemical Formula E-3 was used instead of Chemical Formula D-2. MS: $[M+H]^+=1075$ FIG. 9 is a diagram showing a differential scanning calorimetry of Chemical Formula 1-25.

Preparation Example 6. Preparation of Chemical Formula 1-26

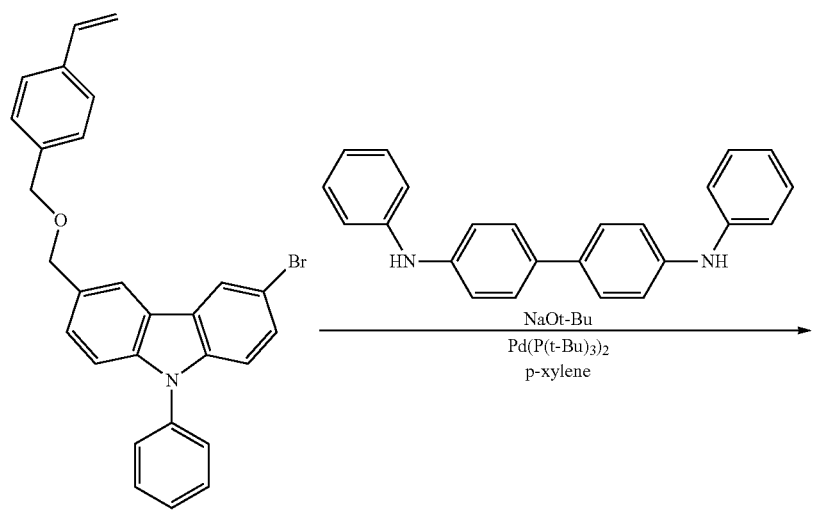

[Chemical Formula E-4]

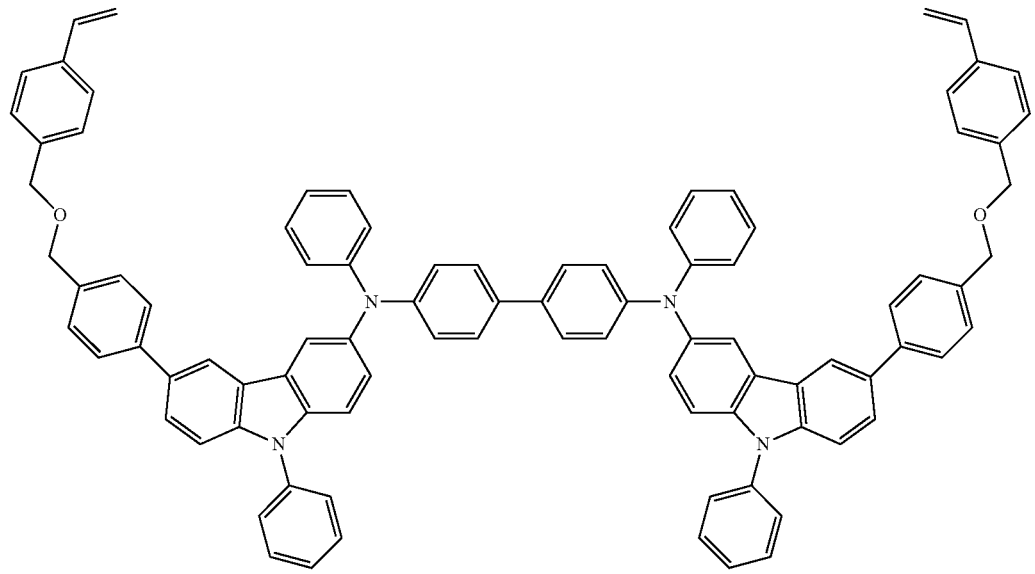
[Chemical Formula 1-26]
(1) Preparation of Chemical Formula 1-26
Compound 1-25 was obtained in the same manner as Chemical Formula E-2 of Preparation Example 2, except that Chemical Formula E-4 was used instead of Chemical Formula D-2. MS: [M+H]$^+$=1263
FIG. 10 is a diagram showing an MS spectrum of Chemical Formula 1-26.
Preparation Example 7. Preparation of Chemical Formula 1-27
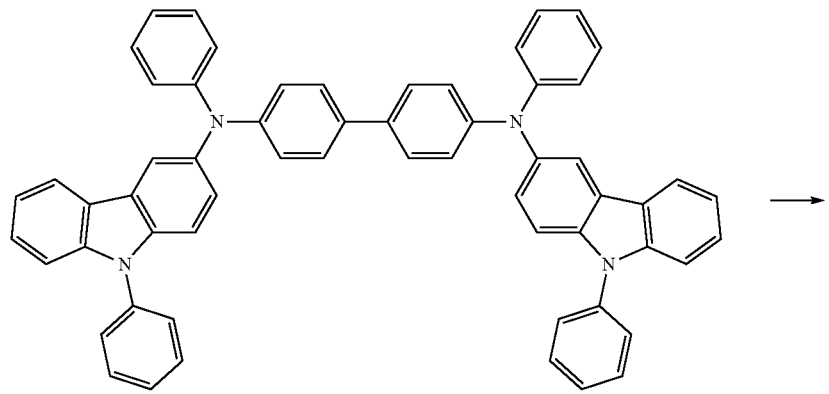
[Chemical Formula E-5]

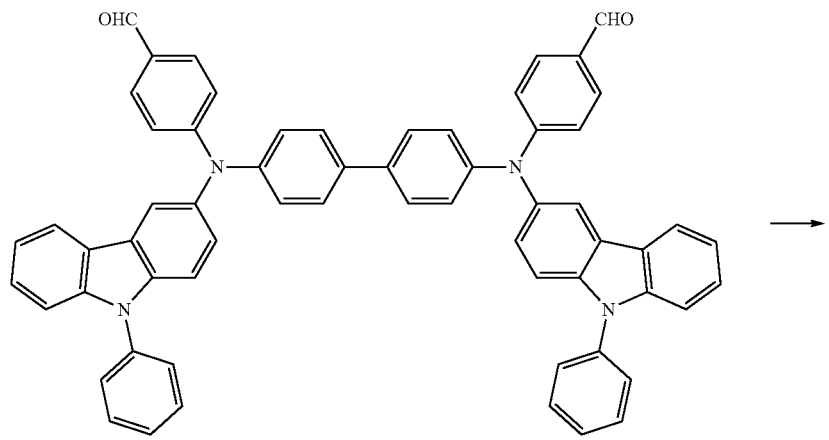

[Chemical Formula E-6]

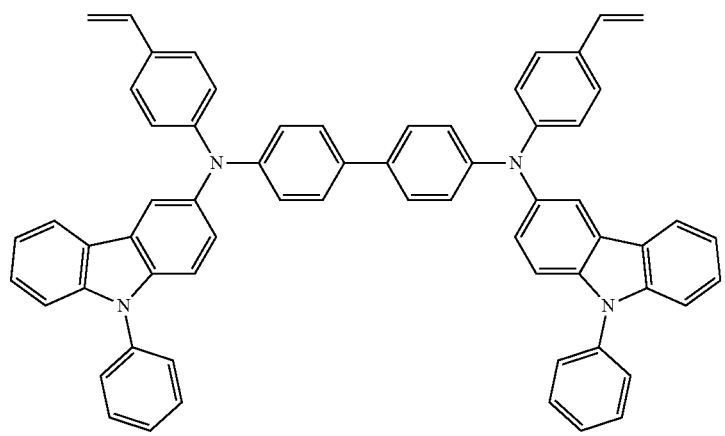

[Chemical Formula 1-27]

(1) Preparation of Chemical Formula E-6

After adding 16 mL of DMF in a 250 mL reaction flask and stirring for 10 minutes, POCl₃ (3.4 ml, 36.6 mmol) was added thereto, and the result was stirred for 10 minutes to prepare a vilsmeier reagent. The compound of Chemical Formula E-5 (10 g, 12.2 mmol) was dissolved in 120 ml of 1,2-dichloroethane, the prepared vilsmeier reagent was added thereto, and the result was stirred for 4 hours at 60° C. Water was added to the reactor, the result was stirred again for 1 hour, and extracted with DCM.

The organic solution was dried using MgSO₄ and filtered, and then the solvent removed using a rotary vacuum evaporator. The result was purified using column chromatography (developing solvent DCM/Hexane=1:2 to 1:1) to obtain 6.82 g of a compound of Chemical Formula E-6.

(2) Preparation of Chemical Formula 1-27

After dissolving methyl triphenylphosphonium bromide (9.8 g, 27.4 mmol) in 150 ml of anhydrous THF, n-BuLi (2.5 M in hexane, 9.6 ml, 24 mmol) was introduced thereto at −78° C. After stirring the result for 30 minutes at −78° C. and for 1 hour at 0° C., the temperature was lowered again to −78° C. Chemical Formula E-6 (3.5 g, 4 mmol) was dissolved in anhydrous THF and was introduced to the reaction flask using a cannula. The result was stirred for 1 hour at −78° C. and for 1 hour at room temperature. Water was added thereto to terminate the reaction, and the reaction solution was diluted with ethyl acetate. The result was extracted with ethyl acetate, dried with NaSO₄, and filtered. The organic solvent was removed using a rotary vacuum evaporator, and the mixture was purified using column chromatography (Et3N:DCM:Hexane=1:40:160 to 1:100:500) to obtain 2.93 g of Chemical Formula 1-27.

FIG. 11 is a diagram showing an NMR spectrum of Chemical Formula 1-27.

FIG. 12 is a diagram showing an MS spectrum of Chemical Formula 1-27.

Preparation Example 8. Preparation of Chemical Formula 1-28
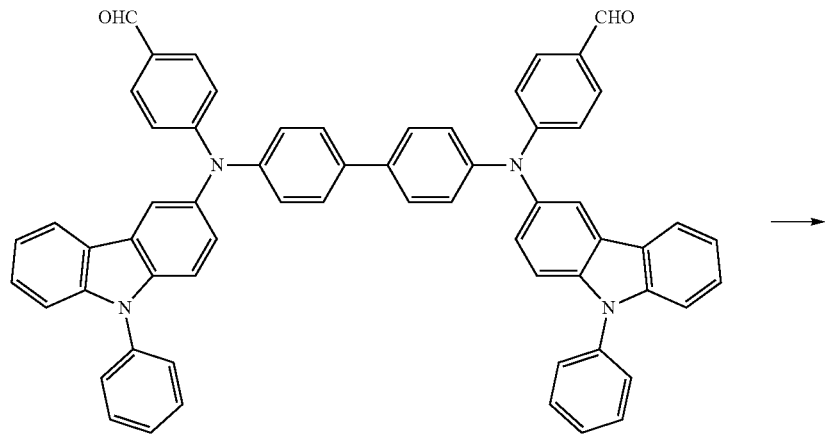
[Chemical Formula E-6]
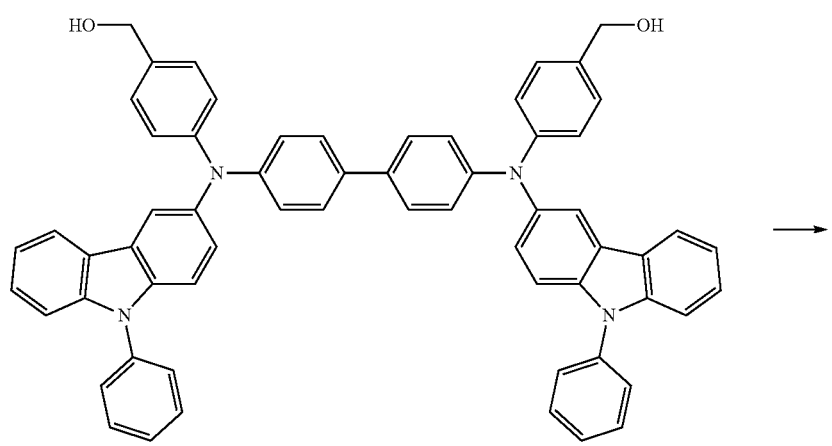
[Chemical Formula F-4]
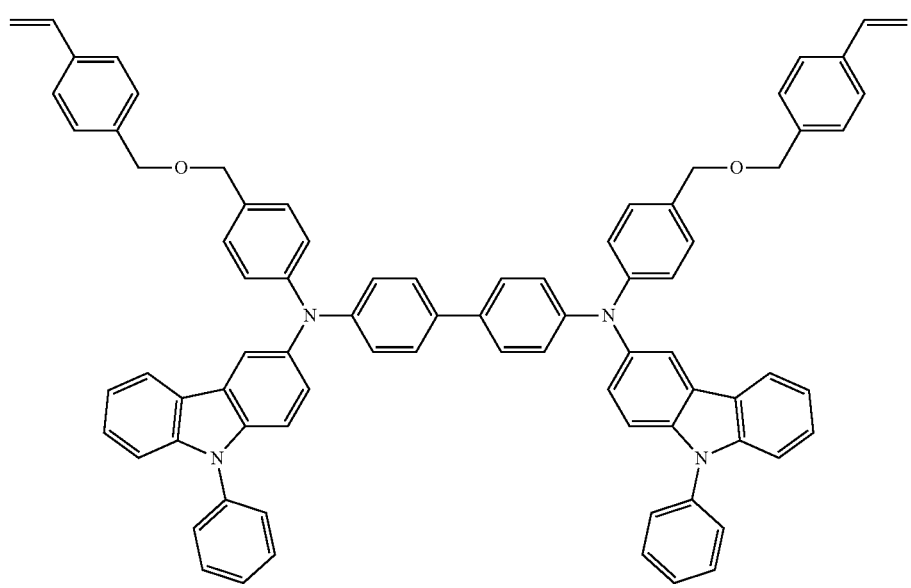
[Chemical Formula 1-28]

(1) Preparation of Chemical Formula F-4

Anhydrous THF was introduced to a flask holding LiAlH (690 g, 17.22 mmol), and the flask was immersed in ice water. Chemical Formula E-6 (5.02 g, 5.74 mmol) was dissolved in THF and slowly added to the reaction flask using a cannula. After stirring the result for 3 hours at 0° C., the reaction was terminated using an aqueous NaOH solution, and the result was stirred for approximately 12 hours. After filtering, the organic solvent was removed using a rotary vacuum evaporator. The residue was dissolved in THF, and precipitated through ethanol addition to obtain 3.7 g of a compound of Chemical Formula F-4.

After dissolving the compound of Chemical Formula F-4 (2.02 g, 2.29 mmol) in 50 mL of anhydrous DMF, the temperature was lowered to 0° C. The result was stirred for 1 hour after adding NaH (60 wt %, 303 mg, 7.57 mmol), and 4-vinylbenzyl chloride (780 μl, 5.5 mmol) was introduced thereto. After stirring the result for 6 hours at 70° C., water was introduced thereto to complete the reaction, and solids were dropped. Filtration was attempted without success, and in this process, other by-products were formed. After column purification, the mixture was recrystallized using DCM and hexane to obtain 0.2 g of a compound of Chemical Formula 1-28.

FIG. 13 is a diagram showing a differential scanning calorimetry of Chemical Formula 1-28.

FIG. 14 is a diagram showing an NMR spectrum of Chemical Formula 1-28.

FIG. 15 is a diagram showing an MS spectrum of Chemical Formula 1-28.

Example 1. Formation of Coating Layer Using Coating Composition

As described in the following Table 1-1, a coating composition was produced by mixing the compound represented by Chemical Formula 1 of the present disclosure; a p-doping material; and an organic solvent (cyclohexanone). In addition, the prepared coating composition was spin coated as described in Table 1-1, and the film was baked at 230° C. to 250° C.

As the following p-doping material, structures of Chemical Formula 2-1 that is an organic compound p-doping material, and Chemical Formula 7-1 and Chemical Formula 7-2 that are d-ionic dopants, were used, however, the p-doping material is not limited thereto.

[Chemical Formula 2-1]

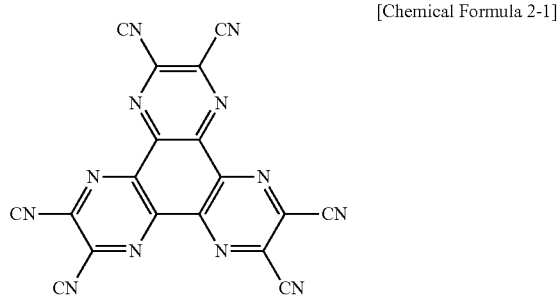

[Chemical Formula 7-1]

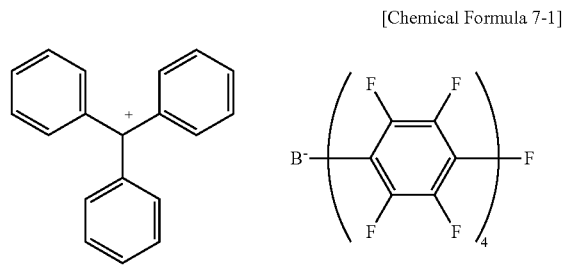

[Chemical Formula 7-11]

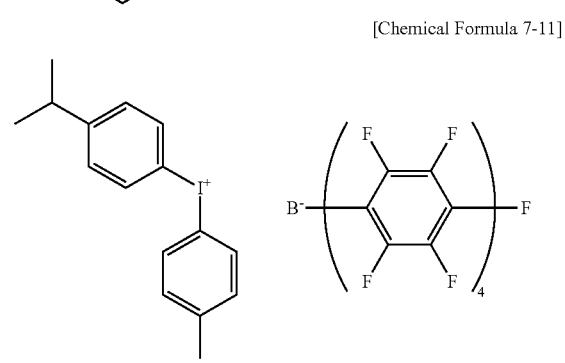

TABLE 1-1

| Coating Composition | Carbazole Derivative | P-Doping Material | Concentration (wt %) | Spin Rate (rpm)/time (s) | Baking Temperature (° C.)/time (min) |
|---|---|---|---|---|---|
| 1 | Chemical Formula 1-1:Chemical Formula 1-2 = 1:0 | 0% | 2 | 1000/60 s | 250/30 |
| 2 | Chemical Formula 1-1:Chemical Formula 1-2 = 8:1 | Chemical Formula 2-1 (10%) | 2 | 1000/60 s | 250/30 |
| 3 | Chemical Formula 1-1:Chemical Formula 1-2 = 1:1 | Chemical Formula 2-1 (10%) | 2 | 1000/60 s | 250/30 |
| 4 | Chemical Formula 1-1:Chemical Formula 1-2 = 0:1 | 0% | 2 | 1000/60 s | 250/30 |
| 5 | Chemical Formula 1-1:Chemical Formula 1-2 = 2:7 | Chemical Formula 2-1 (10%) | 2 | 1000/60 s | 250/30 |
| 6 | Chemical Formula 1-1:Chemical Formula 1-2 = 8:1 | Chemical Formula 5-1 (10%) | 2 | 1000/60 s | 250/30 |

TABLE 1-1-continued

| Composition | Compound | P-Doping Material | Concentration (wt %) | Spin Rate (rpm)/time (s) | Baking Temperature (° C.)/time (min) |
|---|---|---|---|---|---|
| 7 | Chemical Formula 1-1:Chemical Formula 1-2 = 1:1 | Chemical Formula 5-1 (10%) | 2 | 1000/60 s | 250/30 |
| 8 | Chemical Formula 1-1:Chemical Formula 1-2 = 2:7 | Chemical Formula 5-1 (10%) | 2 | 1000/60 s | 250/30 |
| 9 | Chemical Formula 1-1:Chemical Formula 1-2 = 8:1 | Chemical Formula 6-1 (10%) | 2 | 1000/60 s | 250/30 |
| 10 | Chemical Formula 1-1:Chemical Formula 1-2 = 1:1 | Chemical Formula 6-1 (10%) | 2 | 1000/60 s | 250/30 |
| 11 | Chemical Formula 1-1:Chemical Formula 1-2 = 2:7 | Chemical Formula 6-1 (10%) | 2 | 1000/60 s | 250/30 |
| 12 | Chemical Formula 1-1:Chemical Formula 1-17 = 0:1 | Chemical Formula 2-1 (10%) | 2 | 1000/60 s | 250/30 |
| 13 | Chemical Formula 1-1:Chemical Formula 1-17 = 2:7 | Chemical Formula 2-1 (10%) | 2 | 1000/60 s | 250/30 |
| 14 | Chemical Formula 1-1:Chemical Formula 1-2 = 1:0 | Chemical Formula 7-1 (10%) | 1 | 1000/60 s | 230 |
| 15 | Chemical Formula 1-1:Chemical Formula 1-2 = 0:1 | Chemical Formula 7-1 (10%) | 1 | 1000/60 s | 230 |
| 16 | Chemical Formula 1-1:Chemical Formula 1-2 = 1:1 | Chemical Formula 7-1 (10%) | 1 | 1000/60 s | 230 |
| 17 | Chemical Formula 1-1:Chemical Formula 1-2 = 1:0 | Chemical Formula 7-2 (10%) | 1 | 1000/60 s | 230 |
| 18 | Chemical Formula 1-1:Chemical Formula 1-2 = 0:1 | Chemical Formula 7-2 (10%) | 1 | 1000/60 s | 230 |
| 19 | Chemical Formula 1-1:Chemical Formula 1-2 = 1:1 | Chemical Formula 7-2 (10%) | 1 | 1000/60 s | 230 |
| 20 | Chemical Formula 1-28:Chemical Formula 1-25 = 1:0 | Chemical Formula 7-2 (10%) | 1 | 1000/60 s | 230 |
| 21 | Chemical Formula 1-28:Chemical Formula 1-25 = 0:1 | Chemical Formula 7-2 (10%) | 1 | 1000/60 s | 230 |
| 22 | Chemical Formula 1-28:Chemical Formula 1-25 = 1:1 | Chemical Formula 7-2 (10%) | 1 | 1000/60 s | 230 |
| 23 | Chemical Formula 1-28:Chemical Formula 1-26 = 1:0 | Chemical Formula 7-2 (10%) | 1 | 1000/60 s | 230 |
| 24 | Chemical Formula 1-28:Chemical Formula 1-26 = 0:1 | Chemical Formula 7-2 (10%) | 1 | 1000/60 s | 230 |
| 25 | Chemical Formula 1-28:Chemical Formula 1-26 = 1:1 | Chemical Formula 7-2 (10%) | 1 | 1000/60 s | 230 |
| 26 | Chemical Formula 1-28:Chemical Formula 1-27 = 1:0 | Chemical Formula 7-2 (10%) | 1 | 1000/60 s | 230 |
| 27 | Chemical Formula 1-28:Chemical Formula 1-27 = 0:1 | Chemical Formula 7-2 (10%) | 1 | 1000/60 s | 230 |
| 28 | Chemical Formula 1-28:Chemical Formula 1-27 = 1:1 | Chemical Formula 7-2 (10%) | 1 | 1000/60 s | 230 |

Example 2. Identification of Film Retention Rate of Coating Layer

In order to identify a film retention rate of the coating layer formed using the coating composition of Table 1-1, a toluene solvent was spin treated on the top of the film for washing.

When the film formed using the Coating Compositions 1 to 28 included a p-dopant, film shapes were maintained for the toluene.

From the results, it was identified that the coating composition according to one embodiment of the present specification included the carbazole derivative including the functional group capable of crosslinking, and the functional group capable of crosslinking formed crosslinkage resulting in high chemical resistance and a high film retention rate.

Example 2-1. Manufacture of Organic Light Emitting Device

A glass substrate on which indium tin oxide (ITO) was coated as a thin film to a thickness of 1,500 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone, then dried, washed for 5 minutes, and then transferred to a glove box.

On the transparent ITO electrode prepared as above, Coating Composition 1 described in Table 1-1 was spin coated, and heat treated to form to a thickness of 200 Å. After that, the result was transferred to a vacuum depositor, and then a hole transfer layer was formed by vacuum depositing the following Compound 1 on the hole injection layer.

[Compound 1]

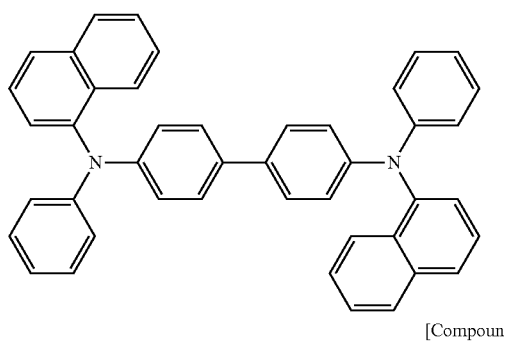

[Compound 2]

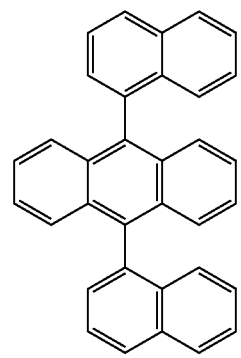

[Compound 3]

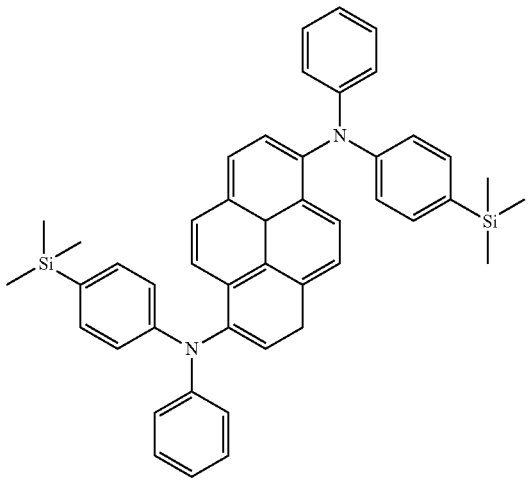

[Compound 4]

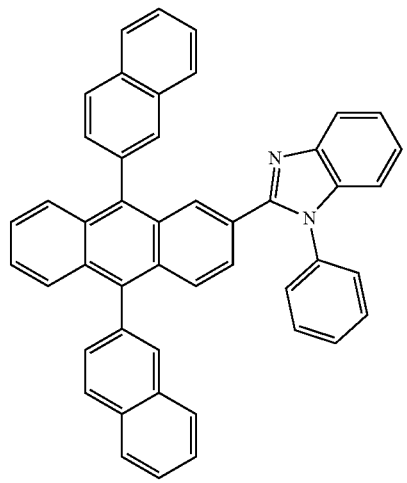

Subsequently, a light emitting layer was formed on the hole transfer layer by vacuum depositing Compound 2 and Compound 3 in 8% concentration to a thickness of 300 Å. An electron injection and transfer layer was formed on the light emitting layer by vacuum depositing Compound 4 to a thickness of 200 Å.

A cathode was formed on the electron injection and transfer layer by depositing lithium fluoride (LiF) to a thickness of 12 Å and aluminum to a thickness of 2,000 Å in consecutive order.

In the above process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum was maintained at $2\times10^{-7}$ torr to $5\times10^{-8}$ torr during the deposition.

Example 2-2

An organic light emitting device was manufactured in the same manner as in Example 2-1 except that Coating Composition 2 was used as the hole injection layer instead of Coating Composition 1.

Example 2-3

An organic light emitting device was manufactured in the same manner as in Example 2-1 except that Coating Composition 3 was used as the hole injection layer instead of Coating Composition 1.

Example 2-4

An organic light emitting device was manufactured in the same manner as in Example 2-1 except that Coating Composition 4 was used as the hole injection layer instead of Coating Composition 1.

Example 2-5

An organic light emitting device was manufactured in the same manner as in Example 2-1 except that Coating Composition 5 was used as the hole injection layer instead of Coating Composition 1.

Example 2-6

An organic light emitting device was manufactured in the same manner as in Example 2-1 except that Coating Composition 6 was used as the hole injection layer instead of Coating Composition 1.

Example 2-7

An organic light emitting device was manufactured in the same manner as in Example 2-1 except that Coating Composition 7 was used as the hole injection layer instead of Coating Composition 1.

Example 2-8

An organic light emitting device was manufactured in the same manner as in Example 2-1 except that Coating Composition 8 was used as the hole injection layer instead of Coating Composition 1.

Example 2-9

An organic light emitting device was manufactured in the same manner as in Example 2-1 except that Coating Composition 9 was used as the hole injection layer instead of Coating Composition 1.

Example 2-10

An organic light emitting device was manufactured in the same manner as in Example 2-1 except that Coating Composition 10 was used as the hole injection layer instead of Coating Composition 1.

Example 2-11

An organic light emitting device was manufactured in the same manner as in Example 2-1 except that Coating Composition 11 was used as the hole injection layer instead of Coating Composition 1.

Example 2-12

An organic light emitting device was manufactured in the same manner as in Example 2-1 except that Coating Composition 12 was used as the hole injection layer instead of Coating Composition 1.

Example 2-13

An organic light emitting device was manufactured in the same manner as in Example 2-1 except that Coating Composition 13 was used as the hole injection layer instead of Coating Composition 1.

Example 2-14 to 2-22

Example 2-14 to Example 2-22 were carried out in the same manner as in Example 2-1 except that Coating Compositions 14 to 22 were used, respectively, as the hole injection layer instead of Coating Composition 1.

Results of measuring driving voltage and light emission efficiency of the organic light emitting devices manufactured using the methods described above at current density of 20 mA/cm$^2$ are shown in the following Table 1.

TABLE 1

| Example | Composition | Driving Voltage (V) | Current Efficiency (cd/A) | Power Efficiency (Lm/W) |
|---|---|---|---|---|
| Example 2-1 | 1 | 9.83 | 2.72 | 0.87 |
| Example 2-2 | 2 | 7.75 | 3.41 | 1.38 |
| Example 2-3 | 3 | 8.42 | 3.13 | 1.17 |
| Example 2-4 | 4 | 10.52 | 2.61 | 0.78 |
| Example 2-5 | 5 | 8.23 | 3.11 | 1.19 |
| Example 2-6 | 6 | 7.51 | 3.24 | 1.36 |
| Example 2-7 | 7 | 8.19 | 2.99 | 1.15 |
| Example 2-8 | 8 | 9.0 | 3.9 | 1.36 |
| Example 2-9 | 9 | 9.25 | 2.24 | 0.76 |
| Example 2-10 | 10 | 8.22 | 2.78 | 1.06 |
| Example 2-11 | 11 | 8.85 | 3.01 | 1.07 |
| Example 2-12 | 12 | 8.83 | 2.66 | 0.95 |
| Example 2-13 | 13 | 7.75 | 3.83 | 1.55 |
| Example 2-14 | 14 | 7.48 | 4.34 | 1.82 |
| Example 2-15 | 15 | 5.24 | 4.69 | 2.81 |
| Example 2-16 | 16 | 5.12 | 4.84 | 2.97 |
| Example 2-17 | 17 | 5.62 | 4.22 | 2.36 |
| Example 2-15 | 18 | 5.18 | 4.73 | 2.87 |
| Example 2-16 | 19 | 5.24 | 4.63 | 2.78 |
| Example 2-17 | 20 | 6.12 | 3.33 | 1.71 |
| Example 2-15 | 21 | 7.10 | 4.11 | 1.82 |
| Example 2-16 | 22 | 8.45 | 4.24 | 1.58 |
| Example 2-17 | 23 | 5.57 | 4.97 | 4.48 |
| Example 2-18 | 24 | 4.80 | 3.62 | 2.37 |
| Example 2-19 | 25 | 4.84 | 3.79 | 2.47 |
| Example 2-20 | 26 | 6.21 | 4.27 | 2.17 |
| Example 2-21 | 27 | 6.08 | 4.27 | 2.21 |
| Example 2-22 | 28 | 6.72 | 3.82 | 1.80 |

Based on the results of Table 1, the carbazole derivative according to one embodiment of the present specification has excellent solubility for organic solvents, readily prepares a coating composition, and using the coating composition, a coating layer may be formed.

In addition, it can be identified that, in the formed coating layer, the carbazole derivatives having a functional group capable of crosslinking included in the coating composition are crosslinked to each other, and capable of forming a layer that is not washed away by a solvent, and therefore, additional layers may be laminated using a solution process, and it can be identified that the carbazole derivatives may be used as a material of an organic light emitting device.

The invention claimed is:
1. A carbazole derivative represented by the following Chemical Formula 1:

[Chemical Formula 1]

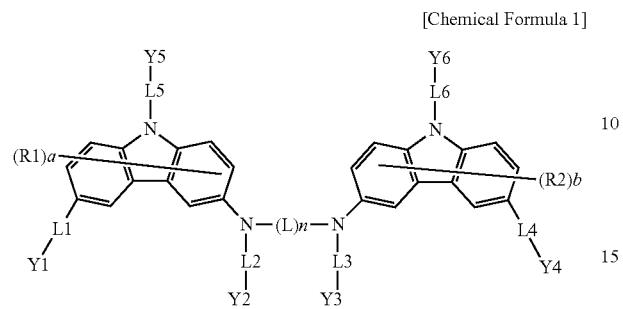

wherein, in Chemical Formula 1,
L is a substituted or unsubstituted arylene group; a substituted or unsubstituted divalent heterocyclic group; or L7-NR'-L8-, wherein L7 and L8 are the same as or different from each other, and each independently a substituted or unsubstituted arylene group, and R' is a substituted or unsubstituted aryl group; or a substituted or unsubstituted heterocyclic group;
L1 and L4 are the same as or different from each other, and each independently a direct bond; a substituted or unsubstituted arylene group; or a substituted or unsubstituted divalent heterocyclic group;
L2 and L3 are the same as or different from each other, and each independently a direct bond; a substituted or unsubstituted alkylene group having 1 to 30 carbon atoms; a substituted or unsubstituted alkenylene group having 1 to 30 carbon atoms; a substituted or unsubstituted arylene group having 6 to 30 carbon atoms; or a substituted or unsubstituted divalent heterocyclic group having 2 to 30 carbon atoms;
L5 and L6 are the same as or different from each other, and each independently a substituted or unsubstituted alkylene group having 1 to 30 carbon atoms; a substituted or unsubstituted alkenylene group having 2 to 30 carbon atoms; a substituted or unsubstituted arylene group having 6 to 30 carbon atoms; or a substituted or unsubstituted divalent heterocyclic group having 2 to 30 carbon atoms;
a and b are each an integer of 1 to 6;
when a and b are each 2 or greater, structures in the parentheses are the same as or different from each other;
R1 and R2 are the same as or different from each other, and each independently hydrogen; deuterium; a substituted or unsubstituted alkyl group having 1 to 30 carbon atoms; a substituted or unsubstituted alkoxy group having 1 to 30 carbon atoms; a substituted or unsubstituted aryl group having 6 to 30 carbon atoms; a substituted or unsubstituted arylamine group; or a substituted or unsubstituted heterocyclic group having 2 to 30 carbon atoms, or adjacent substituents bond to each other to form a substituted or unsubstituted hydrocarbon ring; or a substituted or unsubstituted heterocyclic group;
n is an integer of 1 to 4;
when n is an integer of 2 or greater, two or more Ls are the same as or different from each other; and
Y1 to Y6 are the same as or different from each other, and each independently hydrogen; or a functional group capable of crosslinking by heat or light, and at least one or more of Y1 to Y4 are the functional group capable of crosslinking by heat or light,
wherein the functional group capable of crosslinking by heat or light is selected from the following structures:

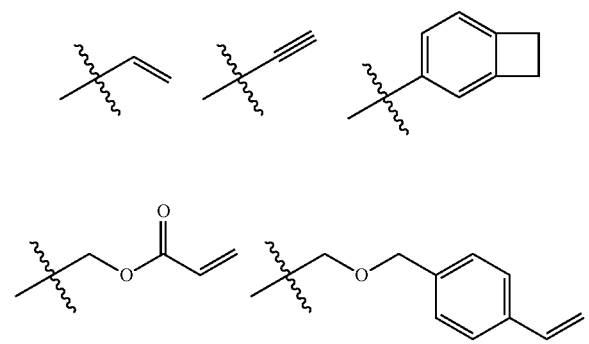

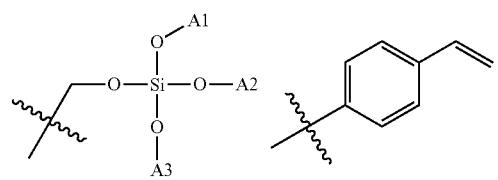

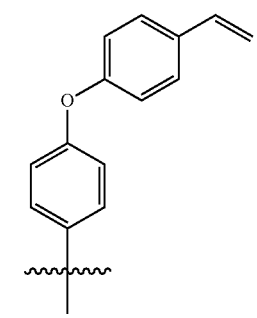

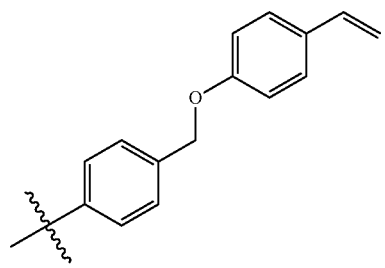

wherein A1 to A3 are the same as or different from each other, and each independently a substituted or unsubstituted alkyl group having 1 to 6 carbon atoms.
2. The carbazole derivative of claim 1, wherein L5 and L6 are the same as or different from each other, and each independently a substituted or unsubstituted arylene group having 6 to 30 carbon atoms.
3. The carbazole derivative of claim 1, wherein L1 and L4 are the same as or different from each other, and each independently a direct bond; or a substituted or unsubstituted phenylene group.

4. The carbazole derivative of claim 1, wherein L2 and L3 are the same as or different from each other, and each independently a direct bond; a substituted or unsubstituted phenylene group; a substituted or unsubstituted biphenylene group; a substituted or unsubstituted naphthylene group; or a substituted or unsubstituted fluorenylene group.

5. The carbazole derivative of claim 1, wherein L is a substituted or unsubstituted phenylene group; a substituted or unsubstituted biphenylene group; a substituted or unsubstituted naphthylene group; a substituted or unsubstituted fluorenylene group; or a substituted or unsubstituted carbazolylene group.

6. The carbazole derivative of claim 1, wherein the carbazole derivative represented by Chemical Formula 1 is represented by any one of the following Chemical Formulae 1-1 to 1-32:

Chemical Formula 1-1

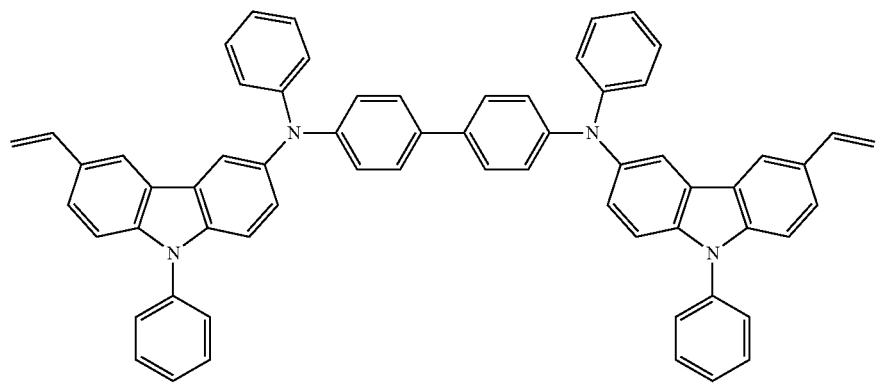

Chemical Formula 1-2

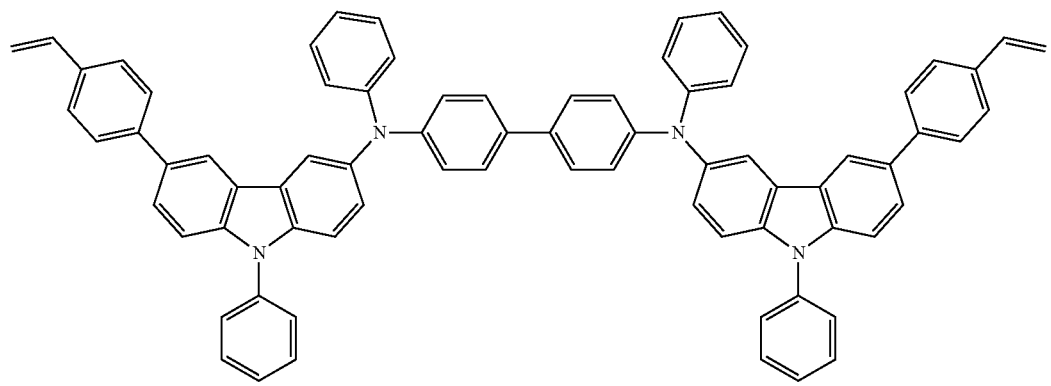

Chemical Formula 1-3

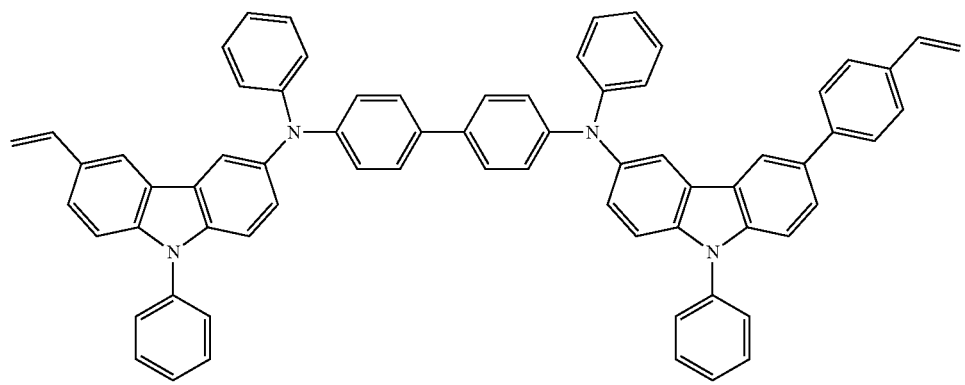

-continued
Chemical Formula 1-4
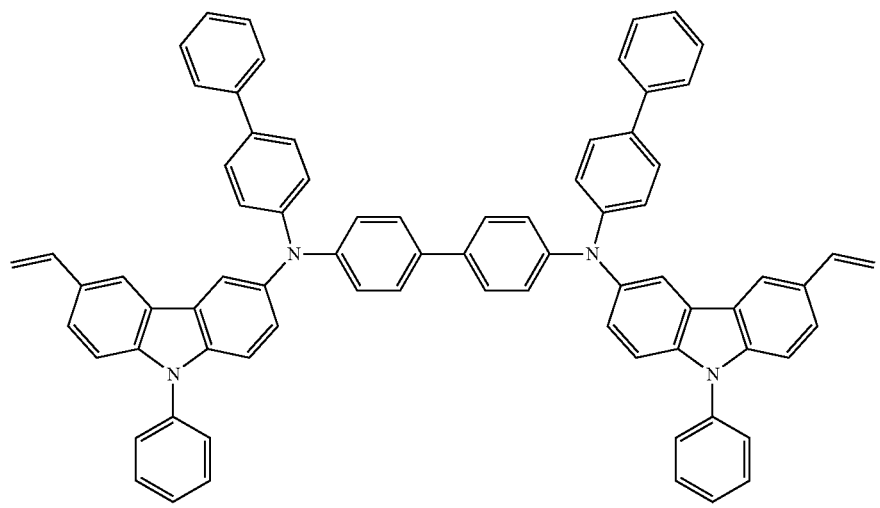
Chemical Formula 1-5
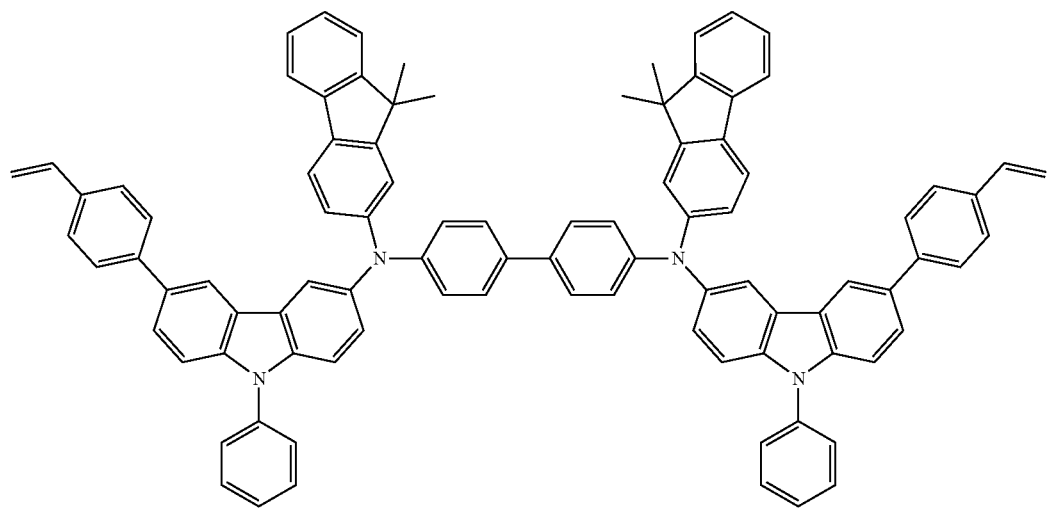
Chemical Formula 1-6
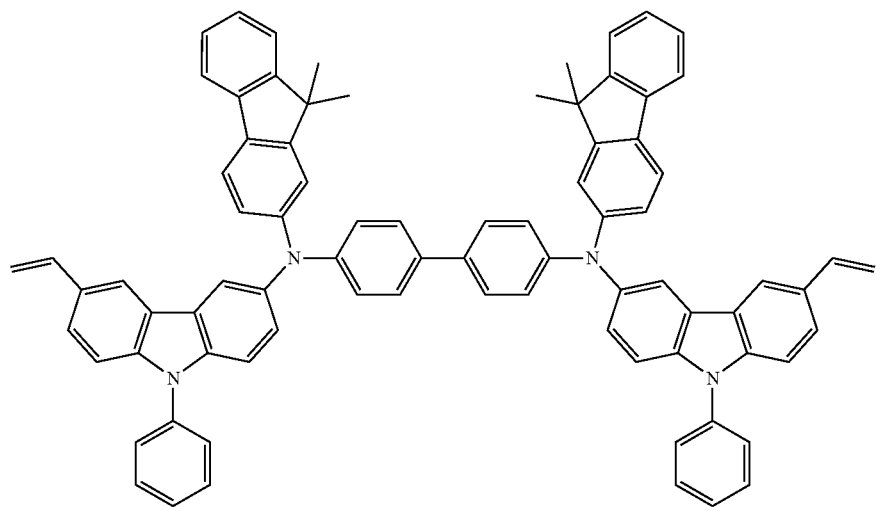

Chemical Formula 1-7
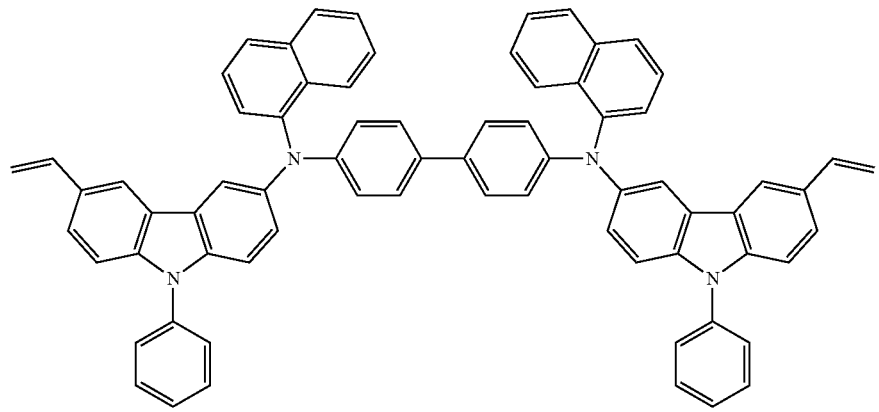
Chemical Formula 1-8
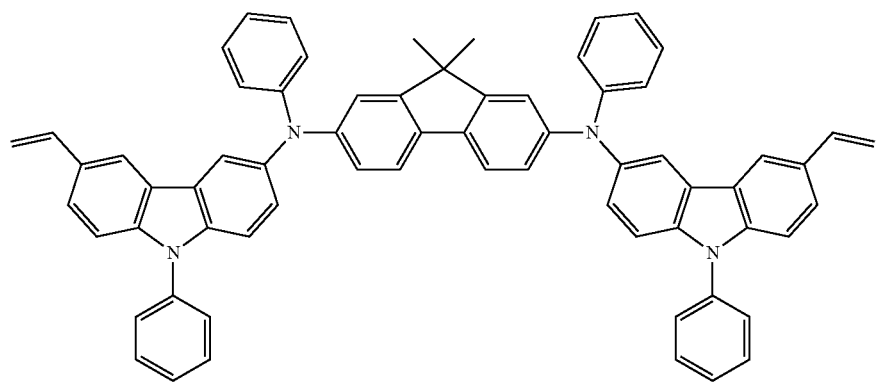
Chemical Formula 1-9
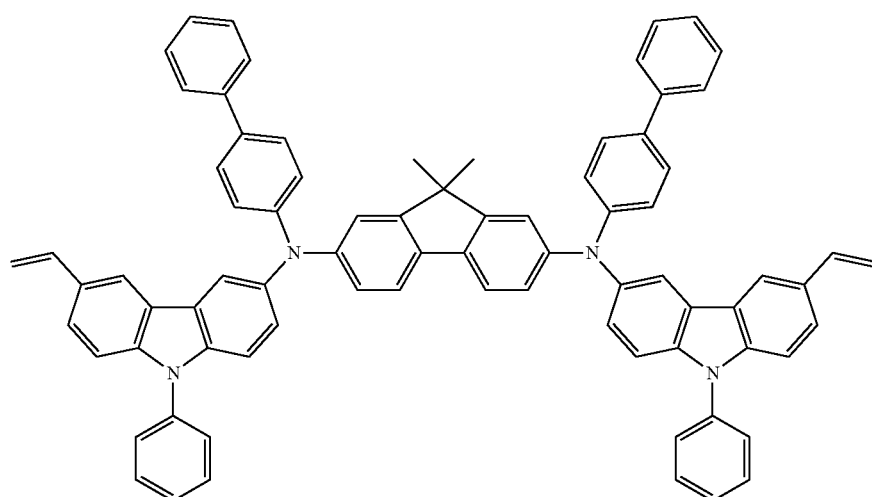

Chemical Formula 1-10
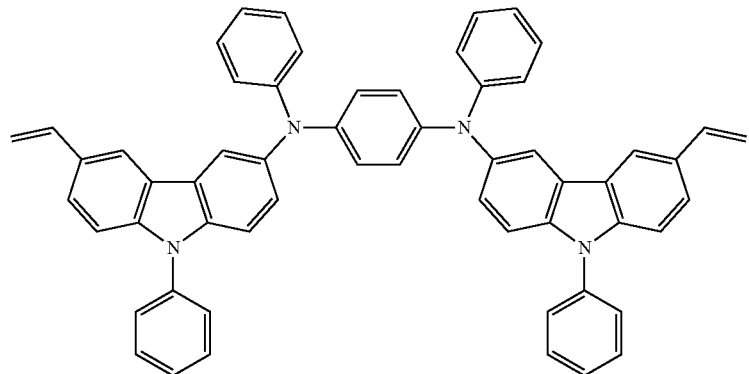
Chemical Formula 1-11
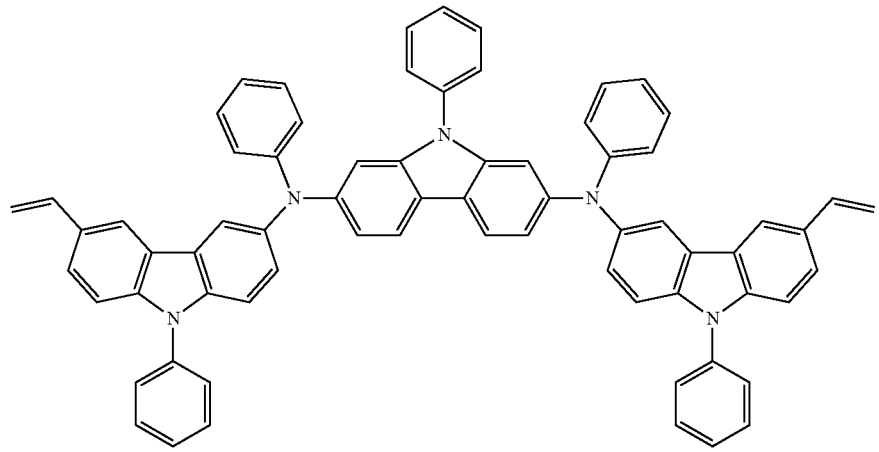
Chemical Formula 1-12
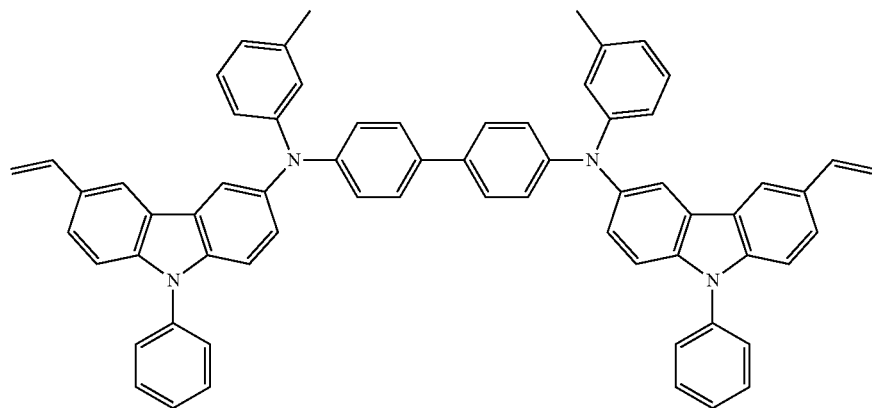
Chemical Formula 1-13
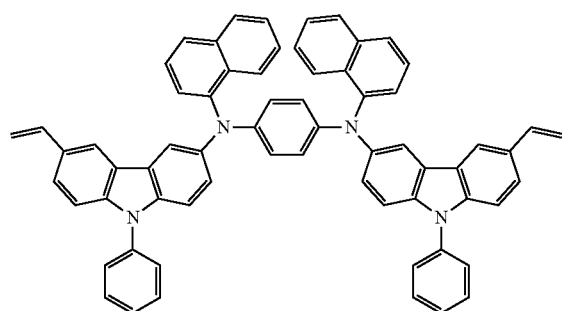
Chemical Formula 1-14
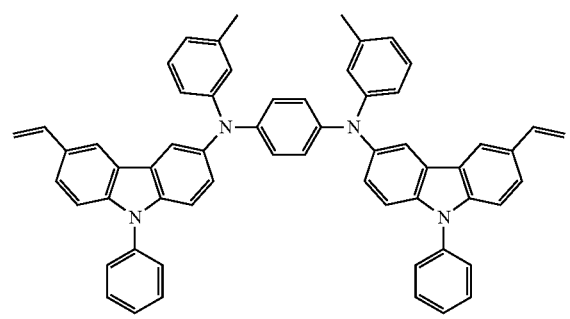

-continued
Chemical Formula 1-15
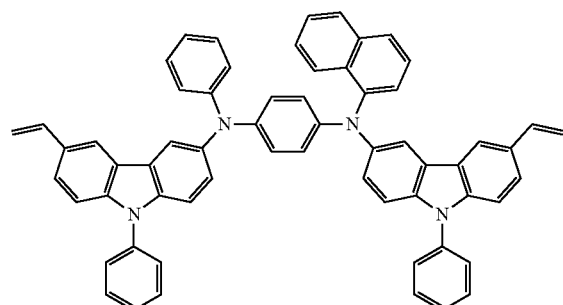
Chemical Formula 1-16
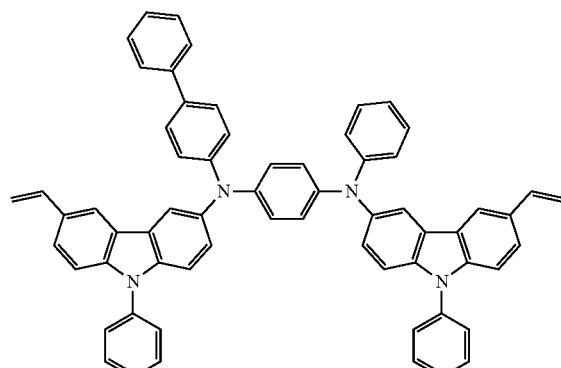
Chemical Formula 1-17
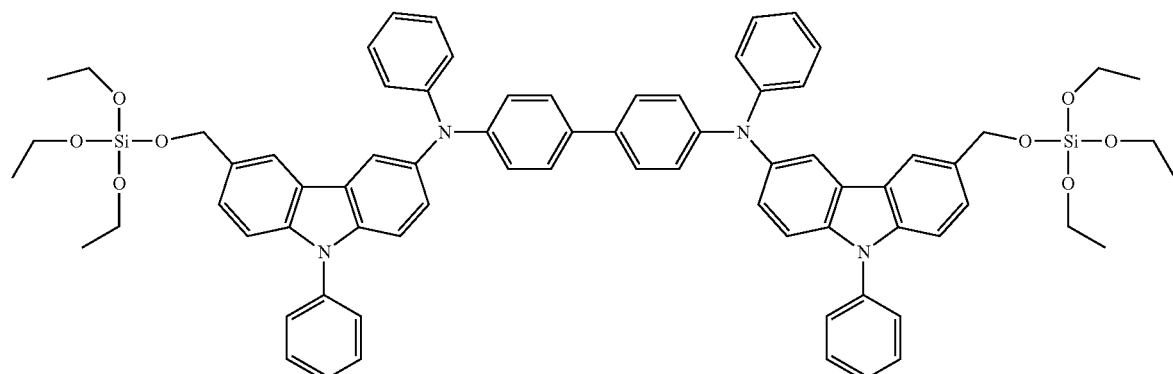
Chemical Formula 1-18
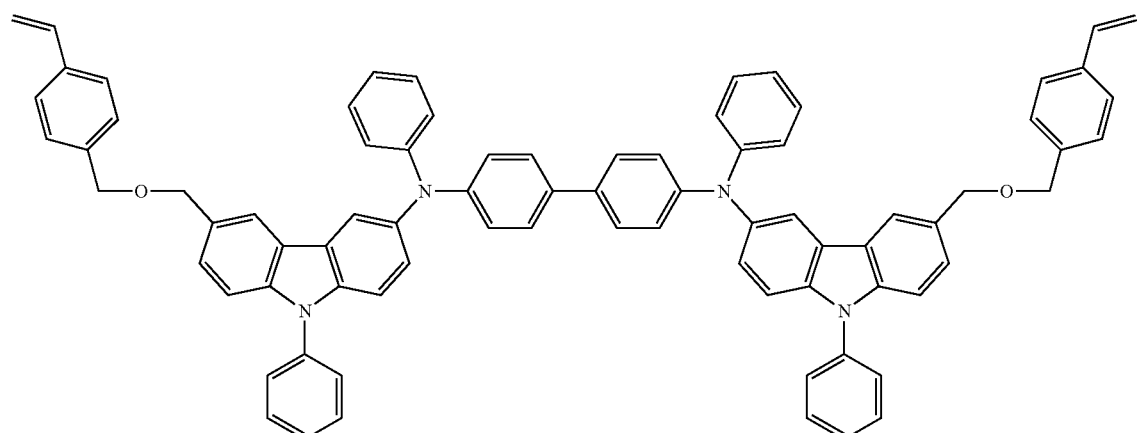
Chemical Formula 1-19
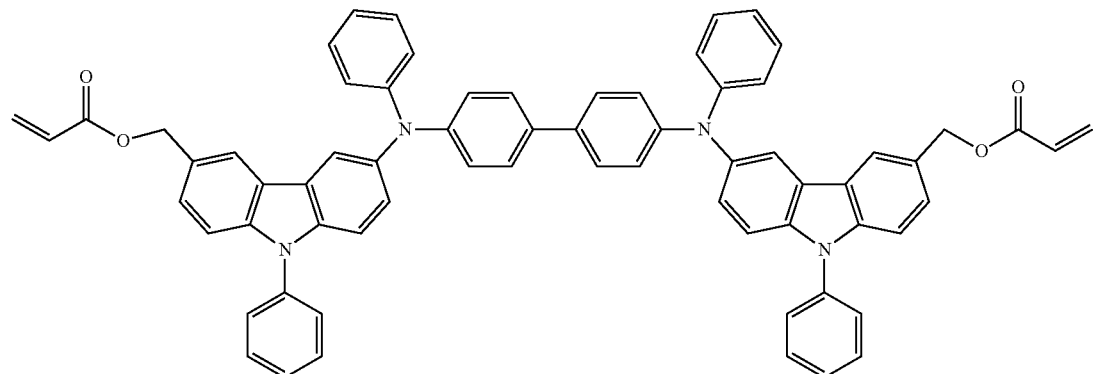

-continued
Chemical Formula 1-20
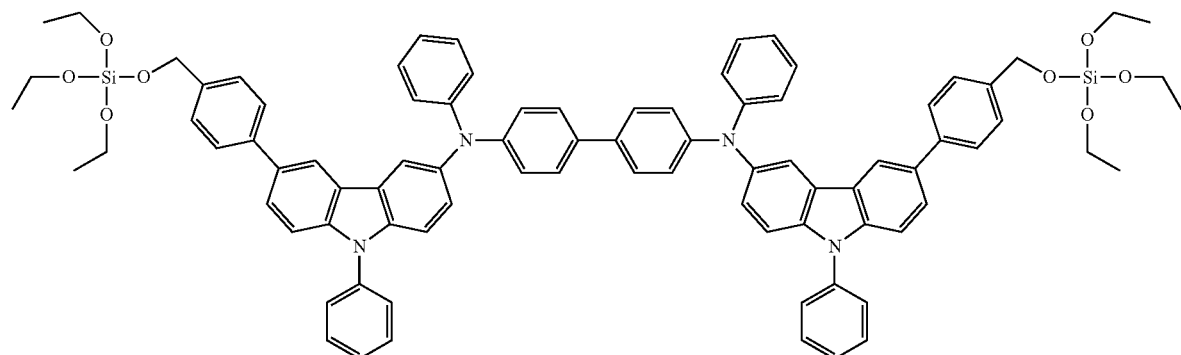
Chemical Formula 1-21
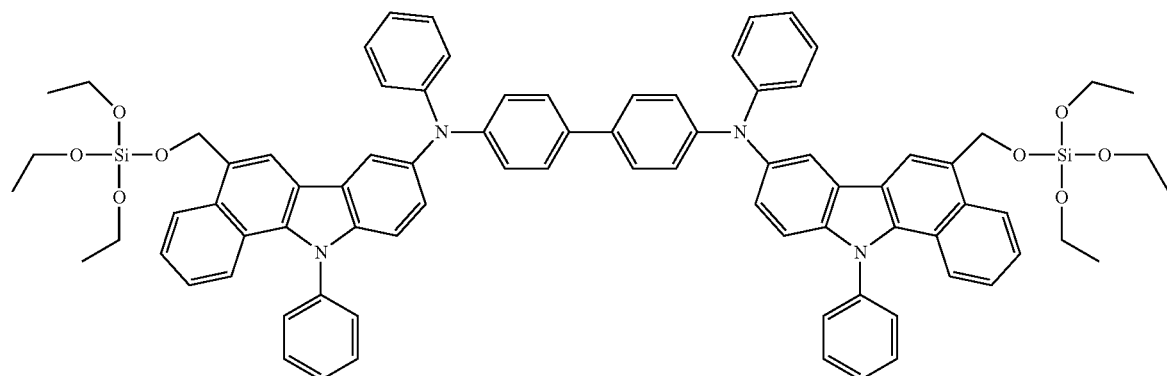
Chemical Formula 1-22
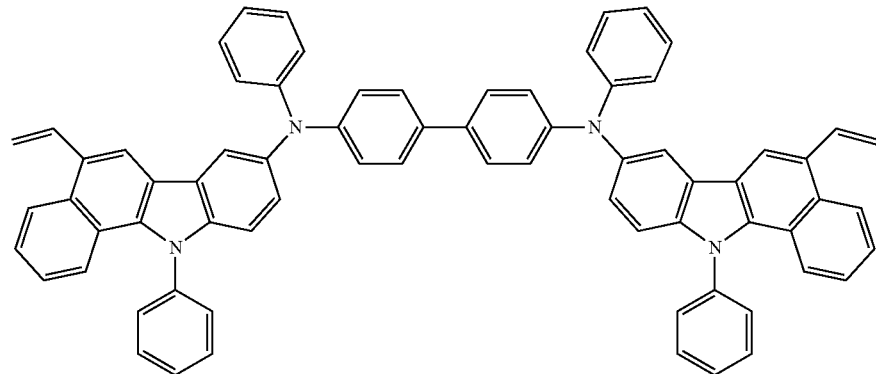
Chemical Formula 1-23
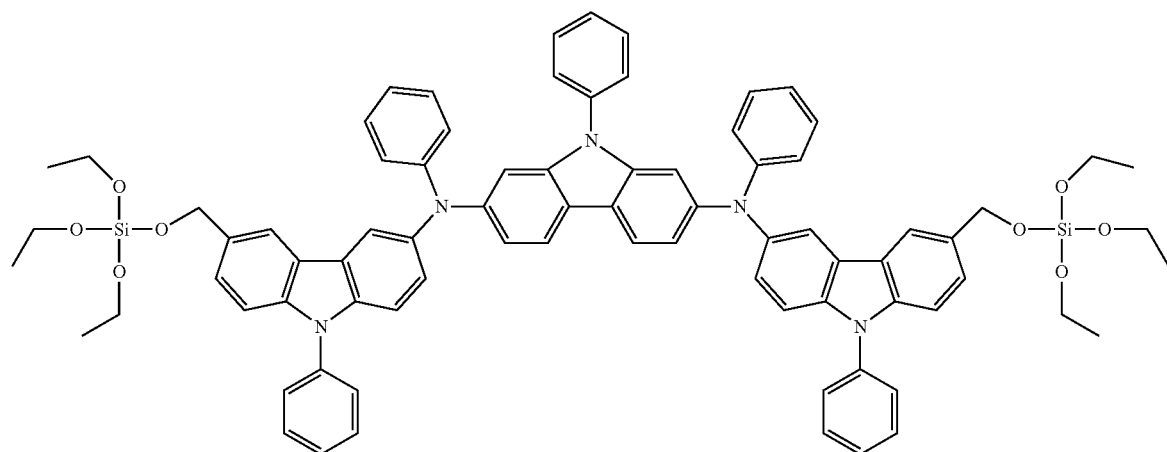

Chemical Formula 1-24
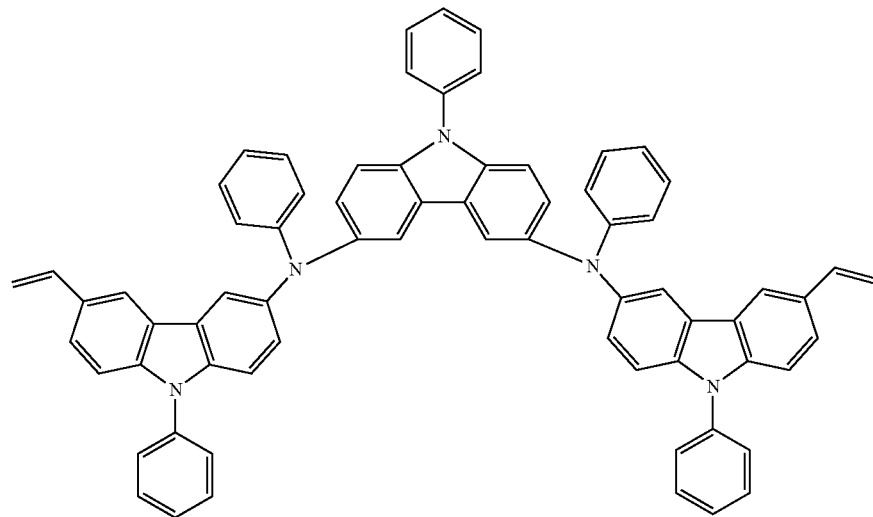
Chemical Formula 1-25
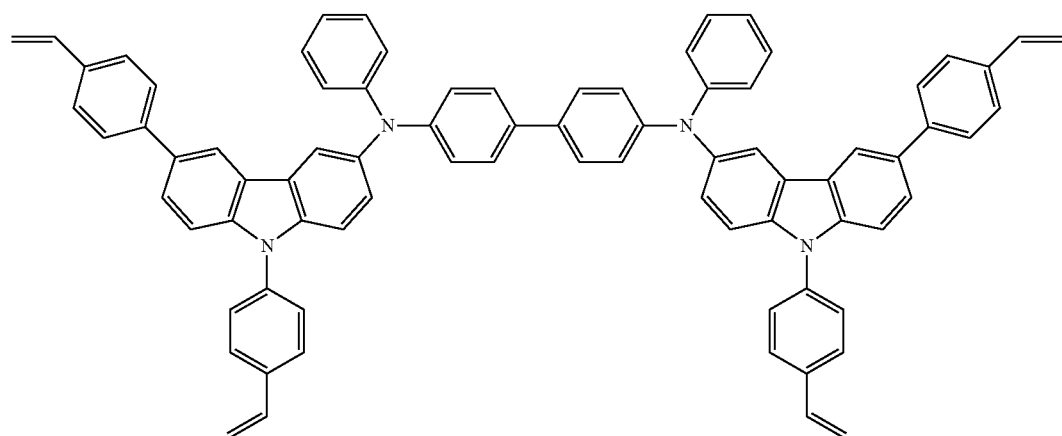
Chemical Formula 1-26
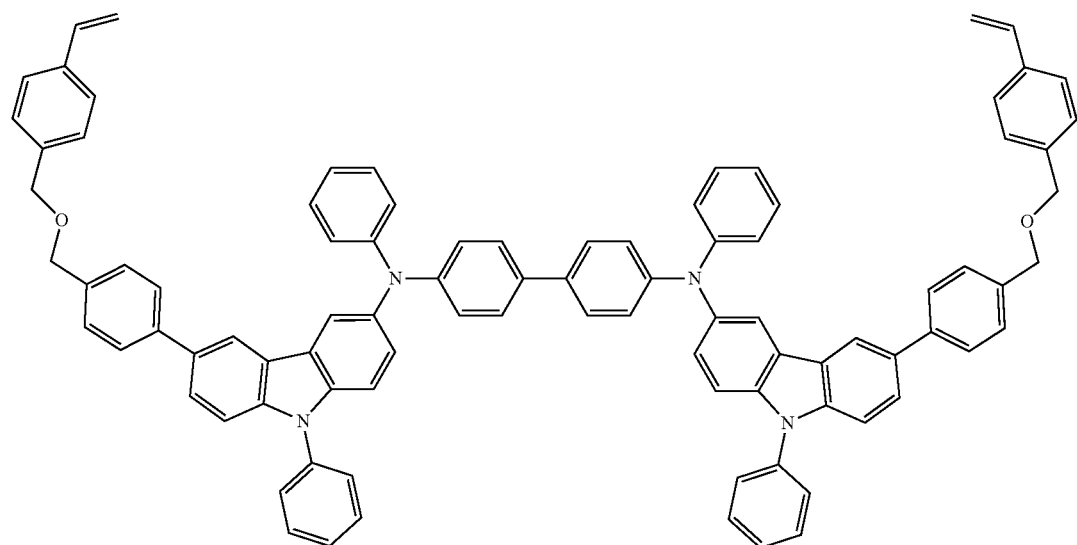

-continued
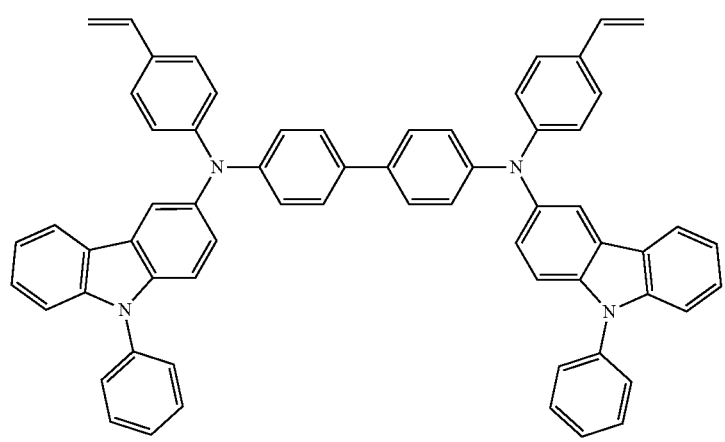
Chemical Formula 1-27
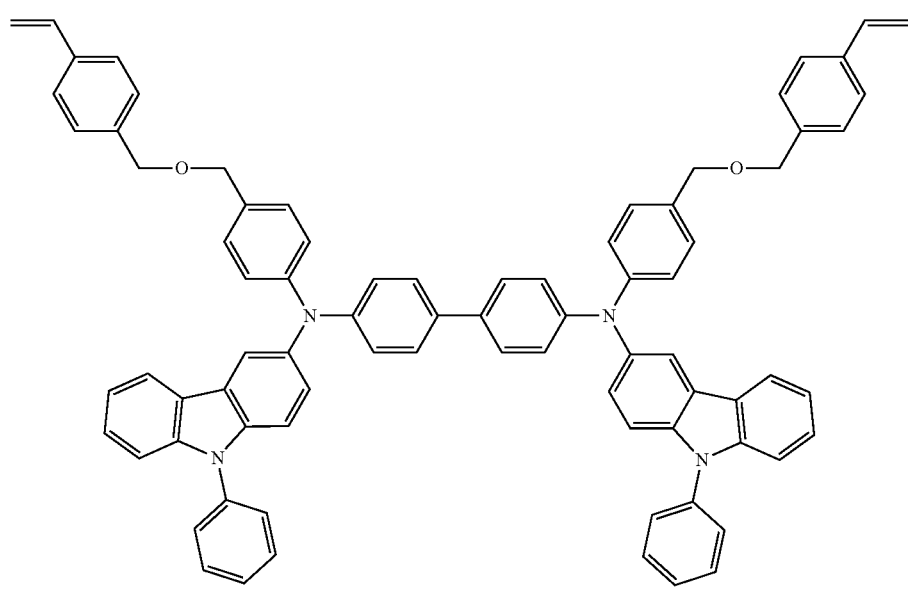
Chemical Formula 1-28
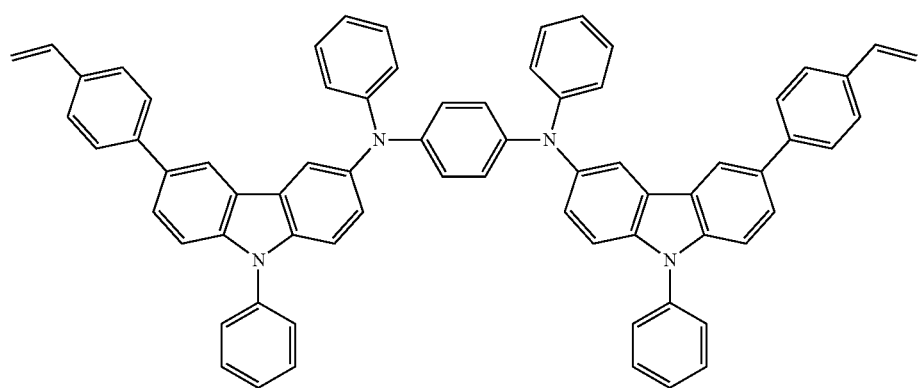
Chemical Formula 1-29

Chemical Formula 1-30
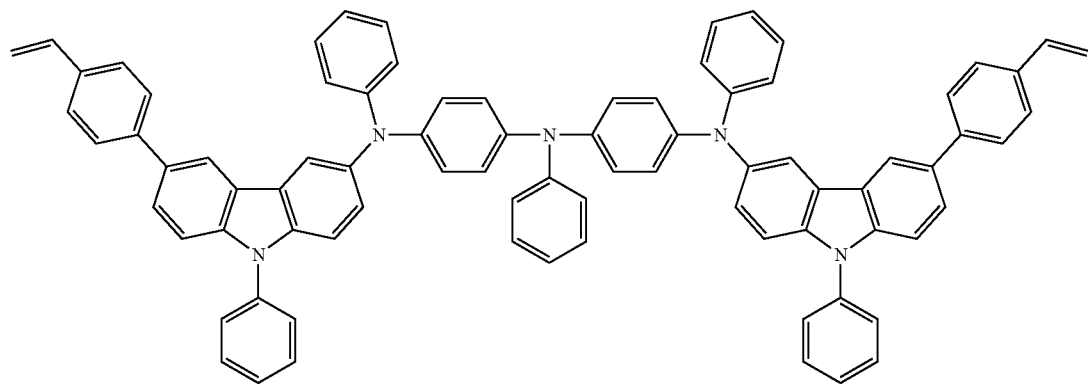
Chemical Formula 1-31
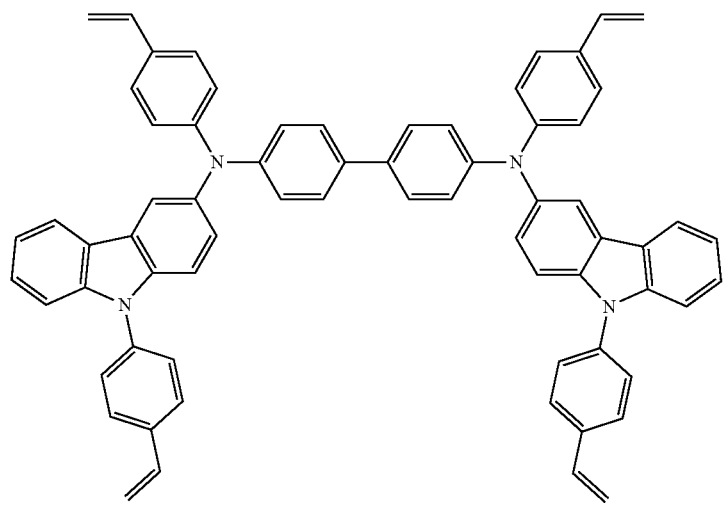
Chemical Formula 1-32
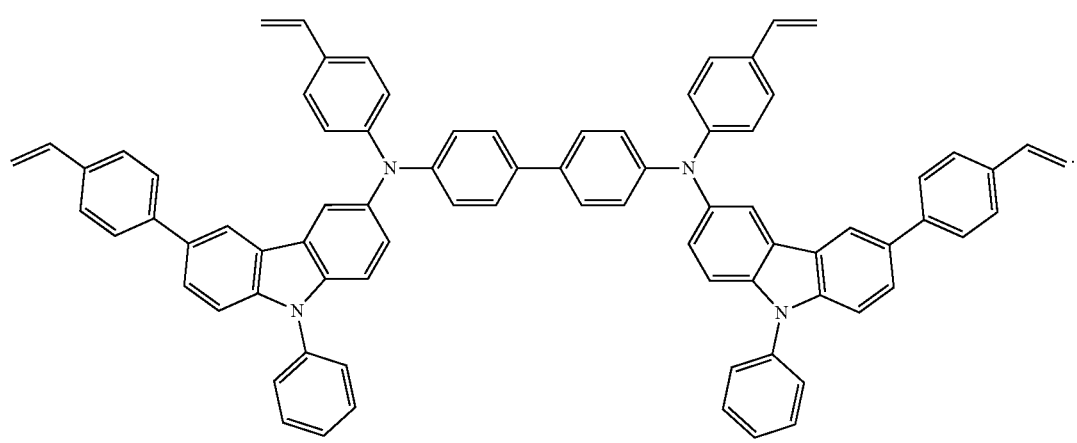

7. A coating composition comprising the carbazole derivative of claim 1.

8. The coating composition of claim 7, further comprising a p-doping material.

9. The coating composition of claim 8, wherein the p-doping material comprises a sulfonic acid compound or a boron anion as an ionic compound.

10. The coating composition of claim 7, which has viscosity of 2 cP to 15 cP.

11. An organic light emitting device comprising:

a cathode;

an anode; and one or more layers of an organic material layer provided between the cathode and the anode, wherein the one or more layers of the organic material layer are formed using the coating composition of claim 7.

12. The organic light emitting device of claim 11, wherein the organic material layer comprises a hole transfer layer, a hole injection layer, or a layer carrying out hole transfer and hole injection at the same time, and at least one of the hole transfer layer, the hole injection layer, or the layer carrying out hole transfer and hole injection at the same time comprises the coating composition.

13. The organic light emitting device of claim 11, wherein the organic material layer comprises a light emitting layer, and the light emitting layer comprises the coating composition.

14. A method for manufacturing an organic light emitting device comprising:

preparing a substrate;

forming a cathode or an anode on the substrate;

forming one or more layers of an organic material layer on the cathode or the anode; and forming an anode or a cathode on the organic material layer, wherein the one or more layers of the organic material layer are formed using the coating composition of claim 7.

15. The method for manufacturing an organic light emitting device of claim 14, wherein the one or more layers of the organic material layer are formed using the coating composition by using spin coating.

16. The method for manufacturing an organic light emitting device of claim 14, wherein the one or more layers of the organic material layer are formed using the coating composition by using a printing method.

17. The method for manufacturing an organic light emitting device of claim 14, wherein the one or more layers of the organic material layer are formed using the coating composition by using an inkjet method.

18. The method for manufacturing an organic light emitting device of claim 14, wherein the one or more layers of the organic material layer are formed by coating the coating composition on the cathode or the anode; and heat treating or light treating of the coated coating composition.

19. The method for manufacturing an organic light emitting device of claim 18, wherein a heat treatment temperature in the heat treating of the coated coating composition is 230° C. or lower.

* * * * *